US010765345B2

(12) United States Patent
Kang et al.

(10) Patent No.: US 10,765,345 B2
(45) Date of Patent: Sep. 8, 2020

(54) METHOD AND SYSTEM FOR DETERMINING A LENGTH OF AN OBJECT USING AN ELECTRONIC DEVICE

(71) Applicant: SAMSUNG ELECTRONICS CO., LTD., Suwon-si (KR)

(72) Inventors: Sung-ji Kang, Seoul (KR); Hye-kang Roh, Seoul (KR); Kun-kook Park, Suwon-si (KR); Jong-sung Dong, Suwon-si (KR); Young-jun Seo, Yongin-si (KR); Jin-sung Kim, Seoul (KR); Hwa-kyung Kim, Seoul (KR); Ju-hee Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 424 days.

(21) Appl. No.: 15/228,102

(22) Filed: Aug. 4, 2016

(65) Prior Publication Data

US 2017/0055881 A1 Mar. 2, 2017

(30) Foreign Application Priority Data

Aug. 24, 2015 (KR) .......................... 10-2015-0119110
Dec. 23, 2015 (KR) .......................... 10-2015-0185173

(51) Int. Cl.
*A61B 5/107* (2006.01)
*A61B 5/00* (2006.01)
(Continued)

(52) U.S. Cl.
CPC ............ *A61B 5/1072* (2013.01); *A61B 5/002* (2013.01); *A61B 5/4872* (2013.01);
(Continued)

(58) Field of Classification Search
CPC ... A61B 5/1072; A61B 5/4872; A61B 5/6804; A61B 5/6823; A61B 5/4866;
(Continued)

(56) References Cited

U.S. PATENT DOCUMENTS 6,146,312 A 11/2000 Sclichter
7,172,560 B2 * 2/2007 Uchida ................ A61B 5/0059
600/587
(Continued)

FOREIGN PATENT DOCUMENTS

CN 203849843 U 9/2014
CN 205214311 U 5/2016
(Continued)

OTHER PUBLICATIONS

Reilly et al., "A device for 24 hour ambulatory monitoring of abdominal girth using inductive plethysmography", Physiological Measurement, vol. 23, No. 4, pp. 661-670 (Year: 2002).*
(Continued)

*Primary Examiner* — Devin B Henson
(74) *Attorney, Agent, or Firm* — Sughrue Mion, PLLC

(57) ABSTRACT

A method of determining a length of an object by using an electronic device includes obtaining, by the electronic device, a length, of the electronic device, between a first point and a second point on the electronic device; obtaining, by the electronic device, a tension applied to a third point on the electronic device, the third point being located between the first point and the second point; and correcting the obtained length by using the obtained tension and prestored reference tension information, the prestored reference tension information indicating a relationship of the tension applied to the third point with respect to the length of the object, and determining the corrected length as a final length of the object.

17 Claims, 50 Drawing Sheets

(51) Int. Cl.
   *A61B 5/08* (2006.01)
   *A61B 5/11* (2006.01)
   *A61B 5/16* (2006.01)
   *A61B 5/113* (2006.01)

(52) U.S. Cl.
   CPC .......... *A61B 5/6804* (2013.01); *A61B 5/6823* (2013.01); *A61B 5/0022* (2013.01); *A61B 5/08* (2013.01); *A61B 5/1116* (2013.01); *A61B 5/1117* (2013.01); *A61B 5/1118* (2013.01); *A61B 5/1135* (2013.01); *A61B 5/165* (2013.01); *A61B 5/4094* (2013.01); *A61B 5/4255* (2013.01); *A61B 5/4866* (2013.01); *A61B 5/7275* (2013.01); *A61B 2562/0219* (2013.01); *A61B 2562/0257* (2013.01); *A61B 2562/0261* (2013.01)

(58) Field of Classification Search
   CPC .......... A61B 5/7275; A61B 2562/0219; A61B 2562/0257; A61B 2562/0261; A61B 2562/0266; A61B 5/1116; A61B 5/1118
   See application file for complete search history.

(56) References Cited

U.S. PATENT DOCUMENTS

| | | | |
|---|---|---|---|
| 7,828,742 | B2 | 11/2010 | Lee et al. |
| 8,585,615 | B2* | 11/2013 | Kasahara ............ A61B 5/0537 600/547 |
| 9,167,857 | B2 | 10/2015 | Jang et al. |
| 2009/0099472 | A1 | 4/2009 | Remmert et al. |
| 2011/0106492 | A1 | 5/2011 | Jang et al. |
| 2013/0345612 | A1* | 12/2013 | Bannister ............ A61B 5/1116 602/19 |
| 2014/0088461 | A1* | 3/2014 | Mack ................... A43D 1/025 600/595 |
| 2014/0142485 | A1* | 5/2014 | Berry ................... A61F 5/028 602/19 |
| 2016/0153853 | A1* | 6/2016 | Brenner .................. G01L 5/047 702/155 |
| 2016/0242695 | A1* | 8/2016 | Ajima .................... G01B 21/20 |
| 2016/0324487 | A1* | 11/2016 | Guo ................... G08B 21/0269 |

FOREIGN PATENT DOCUMENTS

| | | | |
|---|---|---|---|
| KR | 1020070075976 | A | 7/2007 |
| KR | 100815268 | B1 | 3/2008 |
| KR | 10-2008-0106669 | A | 12/2008 |
| KR | 1020080109371 | A | 12/2008 |
| KR | 1020090089741 | A | 8/2009 |
| KR | 10-2010-0021854 | A | 2/2010 |
| KR | 1020130074653 | A | 7/2013 |
| KR | 1020130083013 | A | 7/2013 |
| WO | 2012154687 | A2 | 11/2012 |

OTHER PUBLICATIONS

Joonhoo Jung et al., "Rubber Composites with Piezoresistive Effects", Elastomers and Composites, vol. 48, No. 1, Mar. 2013, doi: http://dx.doi.org/10.7473/EC.2013.48.1.76, pp. 76-84.

Se-Dong Min et al., "Respiration Measurement System using Textile Capacitive Pressure Sensor", Trans. KIEE. vol. 59P, No. 1. Mar. 2010, pp. 58-63.

"Measuring Nanometers Capacitive Sensors for Nano-Measuring Nanometrology", Physik Instrumente, Web based Document, Publication date Unknown but Published before Jul. 13, 2016, Total 9 pages.

"Total solution of power transmission", http://www.jkop.co.krnewproduct1tools.phpsubmenu_code=1, Web based Document, Publication date Unknown but Published before Jul. 13, 2016, Total 7 pages.

"Samsung Electronics, Co., Ltd. Developed a "Smart Belt" That Automatically Measures Waist", Article from ChosunBiz on Aug. 24, 2015, Total 2 pages.

Communication dated Sep. 28, 2017, issued by the Korean Intellectual Property Office in counterpart Korean Application No. 10-2015-0185173.

International Search Report and Written Opinion dated Oct. 7, 2016 issued by the International Searching Authority in counterpart International Application No. PCT/KR2016/006893. (PCT/ISA/210, PCT/ISA/220, and PCT/ISA/237).

Communication dated May 12, 2017, issued by the Korean Intellectual Property Office in counterpart Korean Patent Application No. 10-2015-0185173.

* cited by examiner

FIG. 5

MOTION DETECTION MODULE (510)

WHEN NUMBER OF STEPS IS 0, WAIST SIZE IS DETECTED

| ACCELERATION SENSOR | DETERMINATION OF WALKING | DETERMINATION OF MOVEMENT |
|---|---|---|
| $0 \leq (A1 - A0) < Th$ | STEPS = 0 | A SMALL NUMBER OF MOVEMENTS (LITTLE MOVEMENT) |
| $(A1 - A0) \geq Th$ | STEPS = 1 | A LOT OF MOVEMENTS |

A1 : CURRENT VALUE OF ACCELERATION ENERGY
A0 : PREVIOUS VALUE OF ACCELERATION ENERGY
Th : THRESHOLD VALUE
* ACCELERATION ENERGY = ( (X-AXIS VALUE^2) + (Y-AXIS VALUE^2) + (Z-AXIS VALUE^2) ) ^ (1/2)

POSTURE DETECTION MODULE (520)

WHEN ACCELERATION VARIATION IS GREATER THAN MINIMUM THRESHOLD VALUE, TENSION SENSOR VALUE IS LESS THAN TENSION THRESHOLD VALUE, AND ANGLE VALUE CHANGES WITHIN THRESHOLD RANGE, WAIST SIZE IS DETECTED

| ACCELERATION SENSOR | TENSION SENSOR | PRIMARY POSTURE DETERMINATION | GYROSCOPE SENSOR | SECONDARY POSTURE DETERMINATION |
|---|---|---|---|---|
| $TAmin \leq (A1 - A0)$ | $Tn < Tmin$ | Sit-to-Stand or Stand | $Th0 \leq G \leq Th1$ | ADEQUATE FOR MEASUREMENT |
| $(A1 - A0) < TAmin$ | $Tmin \leq Tn$ | Stand-to-Sit or Sit | else | INADEQUATE FOR MEASUREMENT |

A1 : CURRENT VALUE OF ACCELERATION ENERGY      Tn : TENSION SENSOR VALUE      G : GYROSCOPE SENSOR VALUE
A0 : PREVIOUS VALUE OF ACCELERATION ENERGY     Tmin : TENSION THRESHOLD VALUE   Th0 : MINIMUM THRESHOLD VALUE
TAmin : ACCELERATION THRESHOLD VALUE                                            Th1 : MAXIMUM THRESHOLD VALUE

FIG. 11

| RESPIRATION DETECTION MODULE | | ,1100 |
|---|---|---|
| BREATHING CYCLE IS DETECTED BASED ON VARIATION OF TENSION VALUE → WHETHER DETECTED BREATHING CYCLE IS STABLE IS DETECTED | | |
| DETECTED BREATHING CYCLE | BREATHING RATE | DETERMINATION OF BREATHING |
| 3 TO 5 SECONDS | 12 TO 20 TIMES PER MINUTE | STABLE |
| LESS THAN 3 SECONDS | MORE THAN 20 TIMES PER MINUTE | UNSTABLE |

FIG. 19
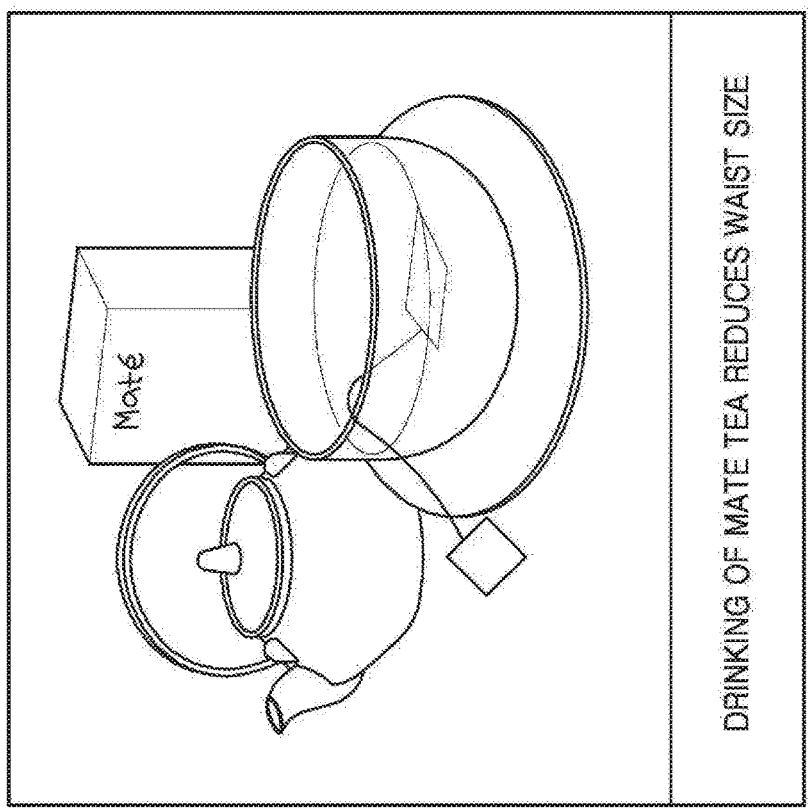
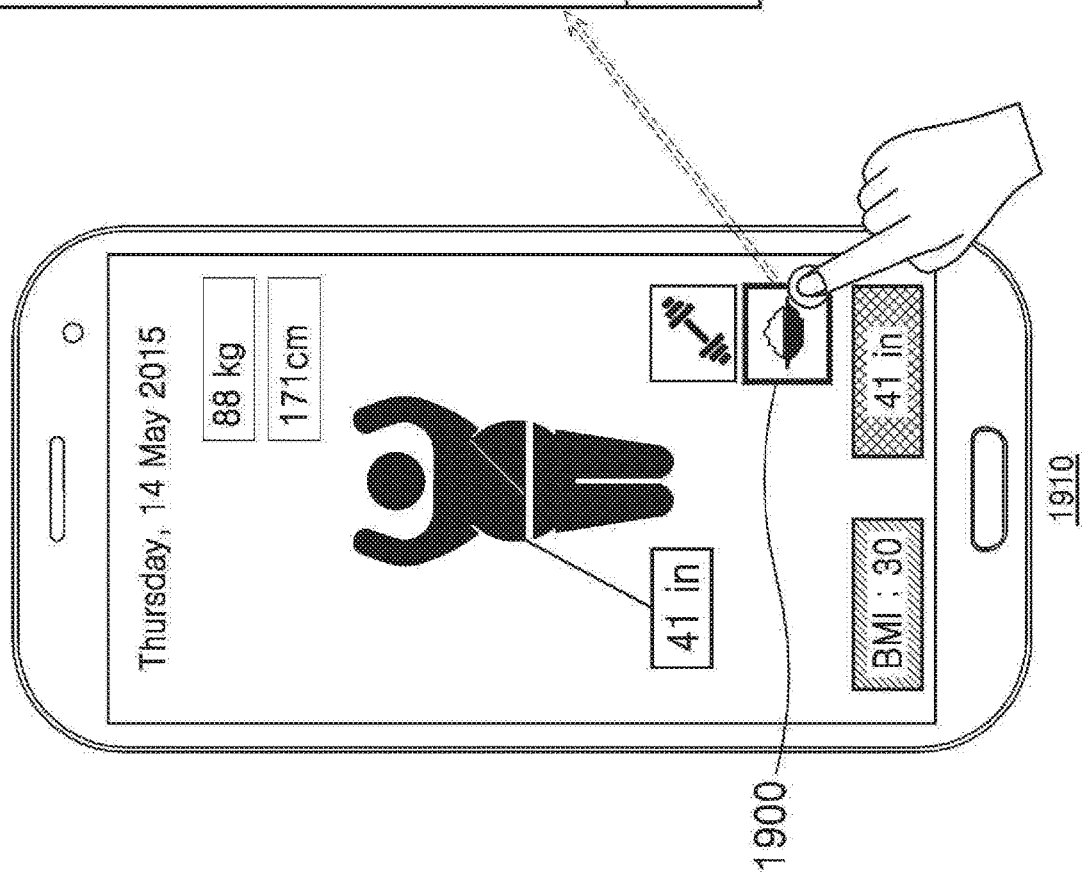

METHOD AND SYSTEM FOR DETERMINING A LENGTH OF AN OBJECT USING AN ELECTRONIC DEVICE

CROSS-REFERENCE TO RELATED PATENT APPLICATION

This application claims priority from Korean Patent Application No. 10-2015-0119110, filed on Aug. 24, 2015, in the Korean Intellectual Property Office, and Korean Patent Application No. 10-2015-0185173, filed on Dec. 23, 2015, in the Korean Intellectual Property Office, the disclosures of which are incorporated herein in their entireties by reference.

BACKGROUND

1. Field

Methods, apparatuses, and systems consistent with exemplary embodiments relate to determining a length of an object using an electronic device, more particularly to, a smart belt including at least one sensor and a waist size management system using the smart belt.

2. Description of the Related Art

As research on wearable devices is being actively conducted, various types of wearable devices have been available. Examples of wearable devices include glasses, bands, watches, and shoes. Wearable devices are widely applied to a health care field because of wearability on human bodies. For example, a wearable band may be used to check and record an exercise quantity, a sleeping time, a sleeping quality, and the like of a user.

According to recent research, when a waist size increases, a thickness of a cerebral cortex decreases, which may increase the probability of developing dementia. Also, it has been found that the risk of a man having a colon cancer is 33% if a waist size of the man increases from 35 inches by 3.3 inches. Thus, developing wearable devices capable of accurately measuring a waist size is desirable.

SUMMARY

One or more exemplary embodiments provide methods and systems for accurately measuring and managing a waist size of a user by using a smart belt including at least one sensor.

One or more exemplary embodiments also provide methods and systems for providing activity information of a user by using a smart belt.

Additional aspects will be set forth in part in the description which follows and, in part, will be apparent from the description, or may be learned by practice of exemplary embodiments.

According to an aspect of an exemplary embodiment, a smart belt includes an inertia sensor configured to acquire motion information of a user who wears the smart belt; a waist size sensor configured to measure the waist size of the user who wears the smart belt; a tension sensor configured to acquire tension information of the smart belt; and a controller configured to determine a motion state of the user by using the motion information of the user, to control the waist size sensor to measure the waist size of the user according to the motion state of the user, and to correct the waist size of the user measured by the waist size sensor, based on the tension information of the smart belt.

According to an aspect of another exemplary embodiment, a waist size managing method of a smart belt includes acquiring motion information of a user who wears the smart belt; determining a motion state of the user by using the motion information of the user; measuring the waist size of the user according to the motion state of the user; acquiring tension information of the smart belt; and correcting the measured waist size of the user, based on the tension information of the smart belt.

According to an aspect of still another exemplary embodiment, a host terminal includes a communicator configured to receive information about the waist size of a user measured by a smart belt, motion information of the user, and tension information of the smart belt from the smart belt; a controller configured to determine a motion state of the user by using the motion information of the user and to correct the waist size of the user measured by the smart belt, based on at least one of the motion state of the user and the tension information of the smart belt; and an output interface configured to output information about the corrected waist size.

According to an aspect of still another exemplary embodiment, a method of determining a length of an object by using an electronic device includes obtaining, by the electronic device, a length, of the electronic device, between a first point and a second point on the electronic device; obtaining, by the electronic device, a tension applied to a third point on the electronic device, the third point being located between the first point and the second point; and correcting the obtained length by using the obtained tension and prestored reference tension information, the prestored reference tension information indicating a relationship of the tension applied to the third point with respect to the length of the object, and determining the corrected length as a final length of the object.

According to an aspect of still another exemplary embodiment, an electronic device for determining a length of an object includes a sensor configured to obtain a length between a first point and a second point on the electronic device; a tension sensor configured to obtain a tension applied to a third point on the electronic device, the third point being located between the first point and the second point; and a controller configured to correct the length between the first and second points by using the tension applied to the third point and prestored reference tension information, which indicates a relationship of the tension applied to the third point with respect to the length of the object, and determine the corrected length as a final length of the object.

According to an aspect of still another exemplary embodiment, a method of providing defecation information of a user who wears a smart belt includes sensing, by the smart belt, whether the user is wears the smart belt; generating, by the smart belt, information about defecation of the user, based on at least one of information about whether the user takes off the smart belt and information about whether the user unties the smart belt; and providing, by the smart belt, the information about the defecation of the user to an external apparatus connected to the electronic device.

According to an aspect of still another exemplary embodiment, a wearable smart belt includes a magnetic portion, including a magnet, disposed at a first portion of the smart belt; a magnetic sensor disposed at a second portion of the smart belt, the magnetic sensor configured to detect the magnet and output a sensing value based on a position of the detect magnet; at least one of a motion sensor and a tension sensor, the motion sensor configured to detect a motion of a user who wears the smart belt and the tension sensor configured to detect a tension applied to the smart belt; and a controller configured to obtain a size of a waist of the user based on the position of the detect magnet and at least one of the detected motion and the detected tension.

BRIEF DESCRIPTION OF THE DRAWINGS

The above and/or other aspects will be more apparent by describing certain example embodiments with reference to the accompanying drawings in which:

FIG. 5 is a view for explaining operations of a motion detection module and a posture detection module according to an exemplary embodiment;

FIG. 11 is a view for explaining a respiration detection module according to an exemplary embodiment;

FIG. 19 is a view for explaining an operation, performed by a host terminal, of recommending food, according to an exemplary embodiment;

DETAILED DESCRIPTION

Figure 1:
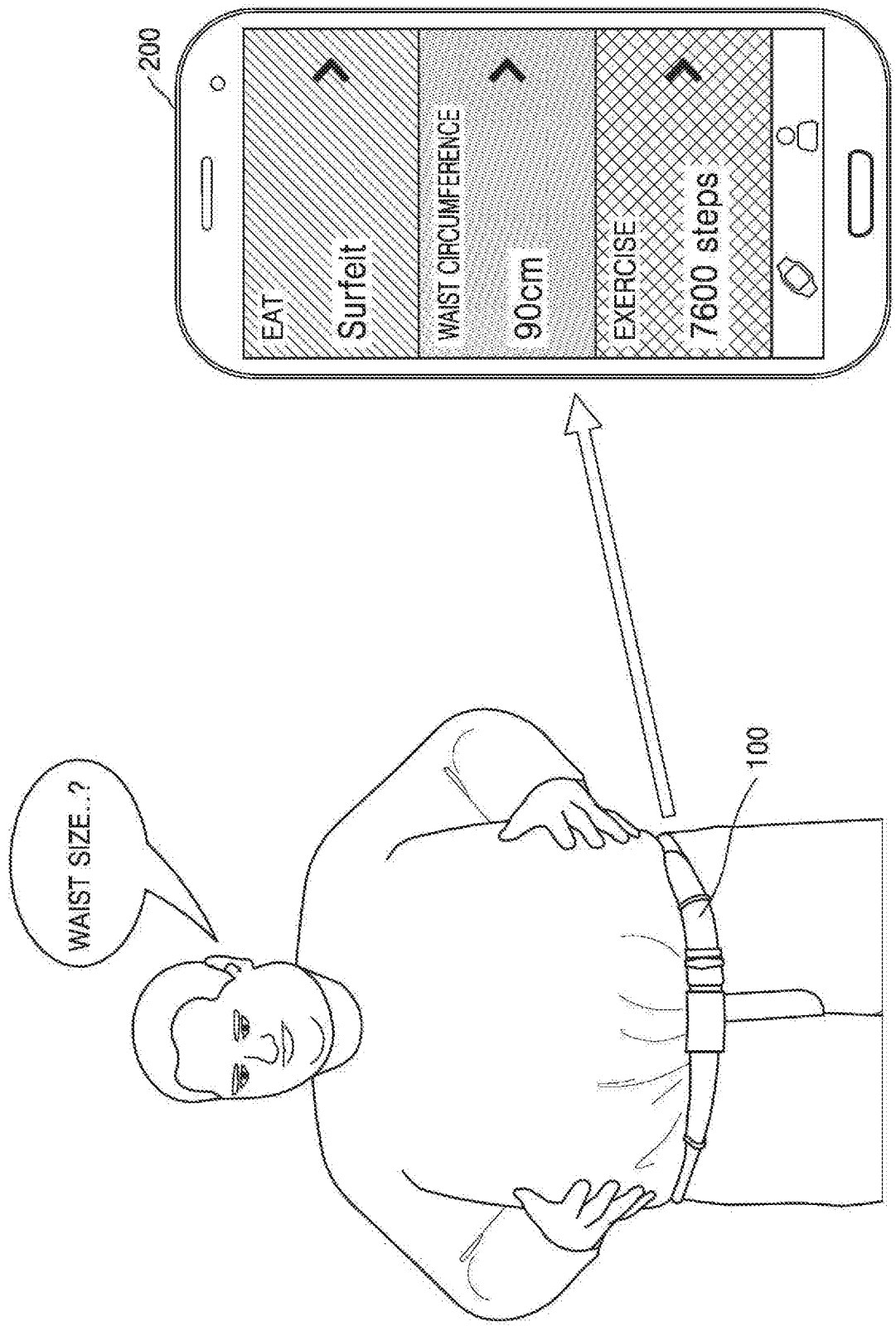
FIG. 1 is a view for explaining a waist size management system according to an exemplary embodiment.

Reference will now be made in detail to certain embodiments, examples of which are illustrated in the accompanying drawings, wherein like reference numerals refer to the like elements throughout. In this regard, the exemplary embodiments may have different forms and should not be construed as being limited to the descriptions set forth herein. Accordingly, exemplary embodiments are merely described below, by referring to the figures, to explain aspects of the description. As used herein, the term "and/or" includes any and all combinations of one or more of the associated listed items. Expressions such as "at least one of," when preceding a list of elements, modify the entire list of elements and do not modify the individual elements of the list.

Hereinafter, the terms used in the specification will be briefly described, and then the inventive concept will be described in detail.

Although general terms widely used in the disclosure are selected for describing the inventive concept in consideration of the functions thereof, these general terms may vary according to intentions of one of ordinary skill in the art, case precedents, the advent of new technologies, and the like. Terms arbitrarily selected by the applicant of the inventive concept may also be used in a specific case. In this case, their meanings need to be given in the detailed description of the inventive concept. Hence, the terms must be defined based on their meanings and the content of the entire specification, not by simply stating the terms.

Herein, an electronic device may be a wearable device including a sensor for measuring a length. For example, an electronic device may be a string-type device surrounding a waist, or a band- or watch-type device surrounding an arm or a wrist. For convenience of explanation, a case where an electronic device is a smart belt will now be illustrated and described, but the inventive concept is not limited thereto.

The terms "comprises" and/or "comprising" or "includes" and/or "including" when used in this specification, specify the presence of stated elements, but do not preclude the presence or addition of one or more other elements. The terms " . . . unit" and " . . . module" when used in this specification refers to a unit in which at least one function or In operation is performed, and may be implemented as hardware, software, or a combination of hardware and software.

Embodiments of the inventive concept are described in detail herein with reference to the accompanying drawings so that this disclosure may be easily performed by one of ordinary skill in the art to which the inventive concept pertains. The inventive concept may, however, be embodied in many different forms and should not be construed as being limited to the embodiments set forth herein. In the drawings, parts irrelevant to the description are omitted for simplicity of explanation, and like numbers refer to like elements throughout.

FIG. 1 is a view for explaining a waist size management system according to an exemplary embodiment.

Referring to FIG. 1, the waist size management system according to an exemplary embodiment may include a smart belt 100 and a host terminal 200. However, all of the illustrated components may not be essential. The waist size management system according to an exemplary embodiment may be implemented by more or less components than those illustrated in FIG. 1. For example, the waist size management system according to an exemplary embodiment may be implemented by including only the smart belt 100 or may be implemented by further including a server in addition to the smart belt 100 and the host terminal 200. An exemplary embodiment in which a waist size management system includes the smart belt 100, the host terminal 200, and a server will be described later in detail with reference to FIG. 23.

The smart belt 100 is a band that may be tied around a waist part of a user. For example, the smart belt 100 may be tied along a waist part of a trouser or skirt to prevent the trouser or skirt from slipping down. The smart belt 100 may be a device capable of automatically measuring the waist size of a user. According to an exemplary embodiment, the smart belt 100 may check the waist size of a user by measuring a length between a first point and a second point on the smart belt 100. In other words, the length between the first point and the second point may correspond to the waist size of the user. The smart belt 100 may have various shapes and comprise various materials.

According to an exemplary embodiment, the smart belt 100 may include at least one sensor. For example, the smart belt 100 may include, but is not limited to, at least one of a geomagnetic field sensor, an acceleration sensor, an inclination sensor, a gyroscope sensor, an optical sensor, an image sensor, a tension sensor, a proximity sensor, a magnetic sensor (hereinafter, also referred to a magnetic field sensor), and a temperature sensor.

The smart belt 100 may sense whether a user wears the smart belt 100, detect a motion of the user, measure the waist size of the user, or measure a tension of the smart belt 100, by using the at least one sensor. A tension may denote a force with which both arbitrary side portions of an object are pulled vertically. The smart belt 100 may correct a measured waist size according to the tension of the smart belt 100. Sensors included in the smart belt 100 will be described in detail later with reference to FIGS. 3A and 3B.

According to an exemplary embodiment, the smart belt 100 may automatically adjust the length of a portion of the smart belt 100 that surrounds the waist of the user. For example, the smart belt 100 may increase the length of the portion of the smart belt 100 surrounding the waist when the user is sitting down, and decrease the length of the portion of the smart belt 100 surrounding the waist when the user stands up. In this manner, the smart belt 100 may flexibly fit a body of the user.

The smart belt 100 may communicate with an external apparatus via a network. According to an exemplary embodiment, the network may be realized by wireless communication technology, such as wireless fidelity (Wi-Fi), home radio frequency (RF), Bluetooth, high rate wireless personal area network (HR WPAN), ultra wideband (UWB), low rate (LR) WPAN, or Institute of Electrical and Electronics Engineering (IEEE) 1394, but the inventive concept is not limited thereto.

For example, the smart belt 100 may transmit information related to a waist size to the host terminal 200. The smart belt 100 may also transmit information on a tension of the smart belt 100, information on respiration of the user, information on overeating of the user, information on a motion of the user, and the like to the host terminal 200. The smart belt 100 may transmit information on a commute, work overtime, defecation, a total period of sitting, seizure or falling, smoking, laugh, and the like of the user to the host terminal 200.

The host terminal 200 may include a display capable of outputting information. For example, the host terminal 200 may output information related to the health of the user (for example, information related to the waist size of the user), a notification message, and a warning message.

The host terminal 200 according to an exemplary embodiment may be realized in various types. Examples of the host terminal 200 may include, but are not limited to, a smartphone, a laptop computer, a tablet personal computer (PC), an electronic-book terminal, a digital broadcasting terminal, a personal digital assistant (PDA), a portable multimedia player (PMP), a navigation, and an MP3 player. The host terminal 200 described herein may be a wearable device that may be worn by users. The wearable device may include at least one of an accessory type device (for example, a watch, a ring, a bracelet, an anklet, a necklace, eyeglasses, or a contact lens), a head-mounted-device (HMD), a fabric or clothing integrated device (for example, electronic clothing), a body-attached device (for example, a skin pad), or a bio-implant device (for example, an implantable circuit).

The user may check his or her health state by checking information about a waist size (also referred to as waist size information) displayed on the host terminal 200. The waist size is an important factor used to determine a metabolic syndrome, and may be given more weight than a body mass index (BMI) to determine obesity. Thus, a system that provides accurate waist size information to users and manages the waist size information of the users is desirable.

Figure 2A:
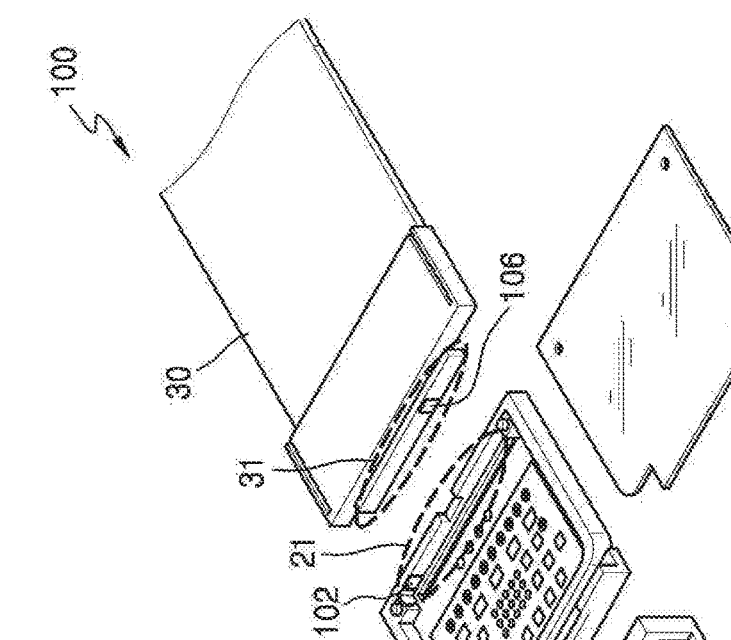
FIGS. 2A and 2B are respectively a perspective view and an exploded view for explaining a smart belt according to an exemplary embodiment.
Figure 2B:
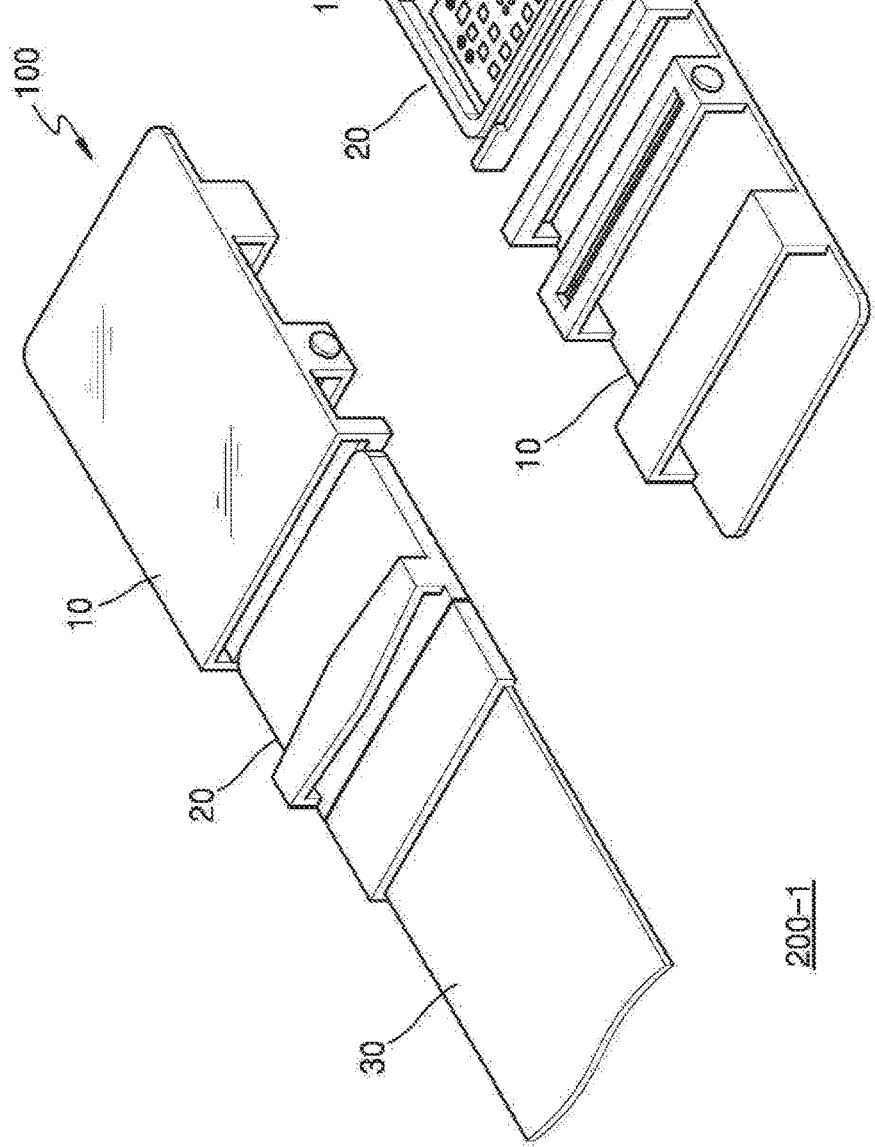

FIGS. 2A and 2B are respectively a perspective view and an exploded view for explaining a smart belt according to an exemplary embodiment.

Referring to FIGS. 2A and 2B, the smart belt 100 may have a structure 200-1 when assembled and have a structure 200-2 when disassembled. The smart belt 100 may include a buckle portion 10, a clip portion 20, and a belt portion 30. The buckle portion 10 may include a device capable of tightening and fixing the belt portion 30. The buckle portion 10 may be implemented as various types, for example but is not limited to, a cinch buckle, a ring buckle, a plate buckle, a rectangular buckle, a clasp buckle, a frame buckle, and a trench buckle.

The clip portion 20 connects the buckle portion 10 to the belt portion 30. According to an exemplary embodiment, the clip portion 20 may include a ring capable of fixing an end portion of the belt portion 30.

According to an exemplary embodiment, the clip portion 20 may include at least one sensor and at least one processor. For example, the clip portion 20 may include, but is not limited to, at least one of a geomagnetic field sensor, an acceleration sensor, an inclination sensor, a gyroscope sensor, an optical sensor, an image sensor, a proximity sensor, a temperature sensor, a magnetic sensor, at least one processor, a communication interface, and a memory.

According to an exemplary embodiment, the belt portion 30 may be implemented using any of various materials, such as leather or fabric. According to an exemplary embodiment, the belt portion 30 may be marked with an indication that represents an absolute location of the marking. For example, the belt portion 30 may be marked with a two-dimensional (2D) code, a color code, an absolute encoder code, or the like. Alternatively, the belt portion 30 may be marked with an indication that represents a relative location of the marking. For example, the belt portion 30 may be marked with an indication at regular intervals.

According to an exemplary embodiment, a waist size sensor (also referred to as a length measurement sensor) of the smart belt 100 may measure the waist size of the user by using an indication marked on the belt portion 30. The waist size sensor that measures the waist size of the user will be described in detail later with reference to FIGS. 3A and 3B.

According to an exemplary embodiment, a tension sensor may be positioned between the clip portion 20 and the belt portion 30. The tension sensor may measure, for example, a tension applied to the smart belt 100 or a variation of the applied tension. The tension sensor may include, but is not limited to, a force sensing resistor (FSR) sensor 102 and/or a strain gauge 106.

For example, the FSR sensor 102 may be located within the clip portion 20, e.g., a portion 21 of the clip portion 20. The FSR sensor 102 may measure a dynamic force (for example, a tension) applied to the smart belt 100 by sensing a resistance change due to a force or pressure applied to a surface of the FSR sensor 102. For example, when the waist size of the user increases, the FSR sensor 102 may sense a resistance change due to a pressure applied to the FSR sensor 102, and recognize that a tension of the smart belt 100 increases.

According to an exemplary embodiment, the strain gauge 106 may be attached to a connection surface 31 that connects the clip portion 20 to the belt portion 30. The strain gauge 106 may be a sensor that measures a change in a strain occurring on a surface of the strain gauge 106.

The strain denotes a ratio of an increased or decreased length of an object to an original length when a tensile force or a compression force is applied to the object. The strain gauge 106 may measure a strain based on a characteristic that an electrical resistance of an object changes when the object is deformed.

A case where a sensor and a processor are provided to the clip portion 20 is illustrated in FIGS. 2A and 2B, but the inventive concept is not limited thereto. For example, the buckle portion 10 may include a sensor and a processor.

Figure 3A:
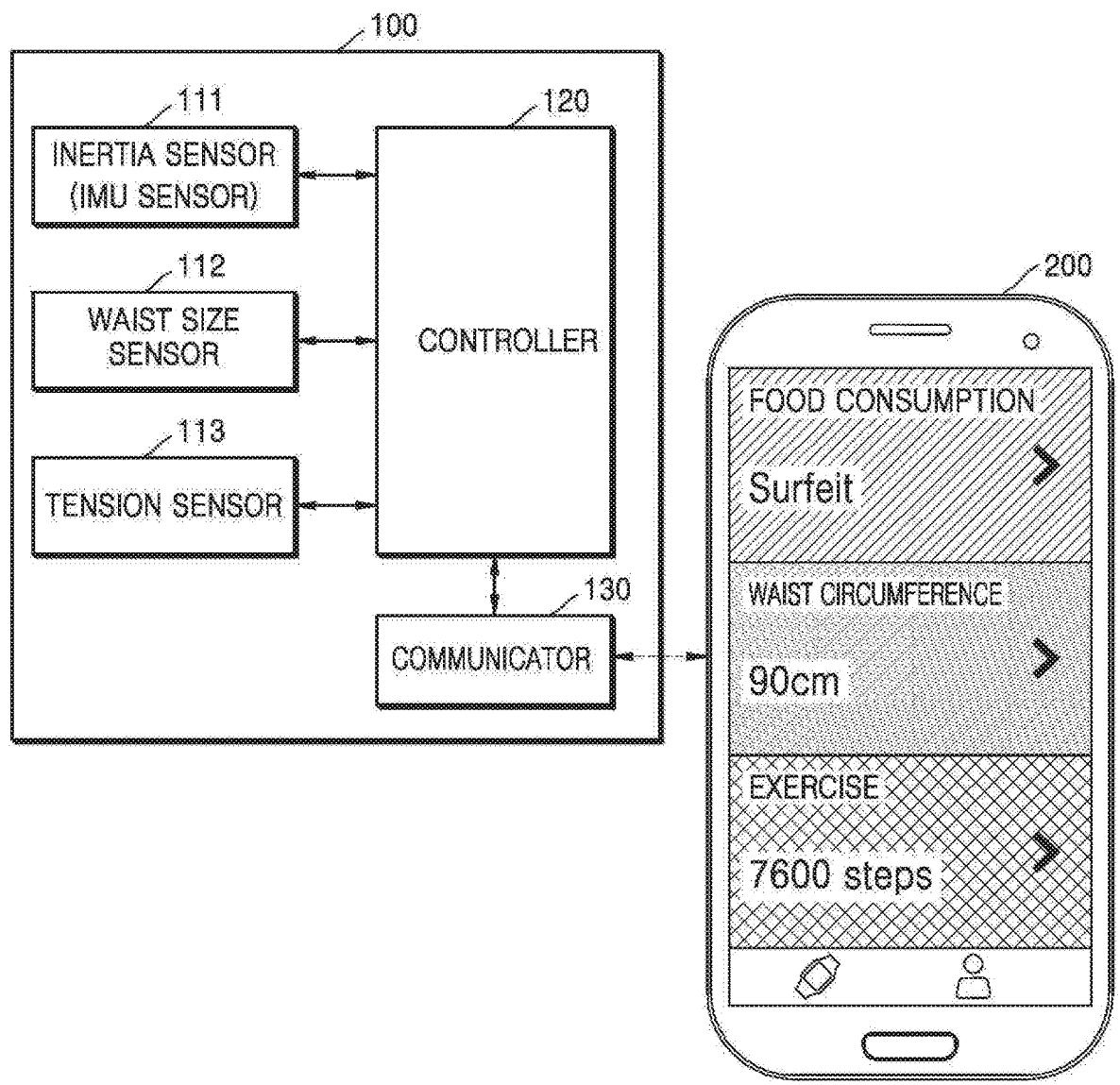
FIG. 3A is a block diagram of a structure of a smart belt according to an exemplary embodiment.
Figure 3B:
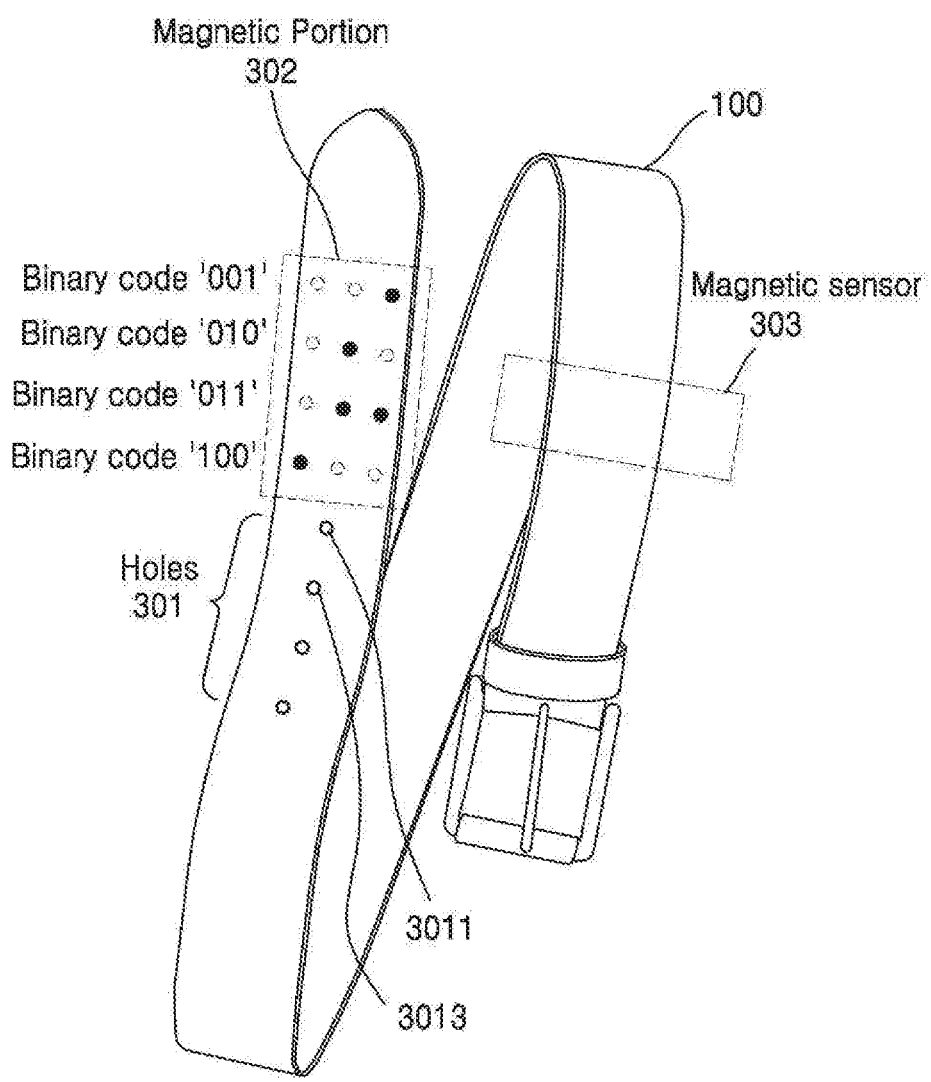
FIG. 3B is a view for explaining an operation, performed by a smart belt, of measuring a waist size of a user by using a magnetic sensor.

FIG. 3A is a block diagram of a structure of the smart belt 100 according to an exemplary embodiment.

Referring to FIG. 3A, the smart belt 100 may include an inertia sensor (or an inertial measurement unit (IMU) sensor) 111, a waist size sensor 112, a tension sensor 113, a controller 120, and a communicator 130. However, all of the illustrated components may not be essential. The smart belt 100 may be implemented by more or less components than those illustrated in FIG. 3A.

The inertia sensor (or IMU sensor) 111 may include an acceleration sensor that measures a gravitational force, and a gyroscope sensor that measures an angular acceleration. According to an exemplary embodiment, the inertia sensor (or IMU sensor) 111 may include a geomagnetic field sensor and a magnetic sensor.

According to an exemplary embodiment, the inertia sensor (or IMU sensor) 111 may acquire motion information of a user (or motion information of the smart belt 100). The motion information of a user may be information about a motion of a user who wears the smart belt 100. For example, the motion information of a user may include, but is not limited to, at least one of a motion of the user, a movement speed of the user, a movement direction of the user, an inclination of the user, and a height of the user. The motion information of a user may also include biometric information (for example, body temperature information, respiration information, and perspiration information) of the user and location information (for example, global positioning system (GPS) coordinate value information, region information, building information, or information about a location variation during a predetermined period of time) of the user. The biometric information of the user and the location information of the user may be measured by a sensor other than the inertia sensor 111.

When the inertia sensor 111 acquires the motion information of the user (for example, a movement speed and a movement direction), the inertia sensor 111 may transmit the motion information of the user to the controller 120.

The waist size sensor 112 may measure the waist size of the user who wears the smart belt 100. The waist size sensor 112 may measure the waist size according to various methods. The waist size sensor 112 may include, but is not limited to, an optical sensor, an image sensor, and a magnetic sensor.

According to an exemplary embodiment, the waist size sensor 112 may measure the waist size by using an optical sensor according to an incremental linear encoder method.

For example, when a mark is attached to the belt portion 30 at regular intervals, the optical sensor may convert, into a pulse signal, a physical signal representing light being transmitted or blocked when passing through the marks. At this time, the controller 120 may count the pulse signal to measure a linear displacement value, and may calculate the waist size by using the linear displacement value. For example, when an interval between marks is 1 cm and the optical sensor recognizes five marks that block light, the waist size sensor 112 may calculate the waist size by subtracting 5 cm (i.e., 1 cm×5) from an overall length of 90 cm of the belt portion 30. According to an exemplary embodiment, physical protrusions instead of slip marks may be used.

According to an exemplary embodiment, the waist size sensor 112 may measure the waist size by using an optical sensor according to an absolute linear encoder method.

For example, when barcodes including absolute location information and/or absolute length information are marked on the belt portion 30, the waist size sensor 112 may measure the waist size of the user by identifying a barcode value by using the optical sensor. For example, when a first barcode value recognized via the optical sensor represents 85 cm, the waist size sensor 112 may determine the waist size of the user to be 85 cm.

According to an exemplary embodiment, when the buckle portion 10 or the clip portion 20 includes a rotor, the waist size sensor 112 may measure the waist size of the user by using a rotary encoder. The rotary encoder may denote a device that converts a rotation angle of a rotational shaft into an electrical signal (or pulse) and outputs the electrical signal (or pulse).

According to an exemplary embodiment, the waist size sensor 112 may measure the waist size according to an incremental rotary encoder method. In this case, the rotor may have a black pattern.

For example, when a user wears the smart belt 100, while the rotor having the black pattern is rotating, light emitted from a light-emission device of the optical sensor may be transmitted or blocked. The transmitted light may be converted into a current by a light-receiving device of the optical sensor, and an electrical signal corresponding to the current may be output as a square wave pulse signal via a waveform shaping circuit and an output circuit. The waist size sensor 112 may calculate the waist size of the user by counting output pulse signals.

According to an exemplary embodiment, when the buckle portion 10 or the clip portion 20 includes a rotor, the waist size sensor 112 may measure the waist size of the user by using an absolute rotary encoder method.

The absolute rotary encoder method is a method of detecting an absolute rotating angle. For example, the method includes splitting 360° around a rotational shaft from a 0° point at a certain ratio, designating a recognizable electrical digital code (for example, a binary coded decimal (BCD) code, a binary code, or a gray code) for each split angle, and outputting the split angle based on the recognized digital code according to a rotation location of the rotating shaft.

According to an exemplary embodiment, the waist size sensor 112 may measure the waist size of the user by using an image sensor.

For example, the waist size sensor 112 may identify a location of the buckle portion 10 or the clip portion 20 on the belt portion 30 by comparing an image of the belt portion 30 acquired via the image sensor with a reference image.

According to an exemplary embodiment, when the waist size sensor 112 measures the waist size of the user who wears the smart belt 100, the waist size sensor 112 may transmit information about the measured waist size to the controller 120.

According to an exemplary embodiment, the waist size sensor 112 may measure the waist size of the user by using a magnetic sensor. For example, referring to FIG. 3B, when the smart belt 100 is a belt of which a length is adjustable by using a plurality of holes 301, the waist size sensor 112 may determine at least one of the plurality of holes 301 that is currently being used to adjust the length of the smart bel 100, by using a magnetic sensor 303.

For example, a magnetic portion 302 may be formed on an end portion of the smart belt 100 at regular intervals. In this case, magnets of the magnetic portion 302 may be located within the smart belt 100 such that the magnets are not prominent. The interval between rows on which magnets of the magnetic portion 302 are arranged may be identical or similar to an interval between the holes 301. The magnetic sensor 303 capable of detecting the magnets may be positioned at a certain distance from a ring 305 of the clip portion.

When a user wears the smart belt 100 by using a first hole 3011 among the holes 301, the magnetic sensor 303 may recognize a magnet on a first row. Since the magnet on the first row is positioned in the last column of the magnetic portion 302, the magnetic sensor 303 may recognize a magnet value as a binary code of '001'. Since the binary code of '001' is converted into a decimal code of '1', the waist size sensor 112 may recognize that the user is using the first hole 3011 that corresponds to the decimal code of '1'. The waist size sensor 112 may determine a length of 85 cm based on an overall length of the belt portion and a location of the first hole 3011 as the waist size of the user.

When the user wears the smart belt 100 by using a second hole 3013, the magnetic sensor 303 may recognize a magnet on a second row. Since the magnet on the second row is positioned in a middle column of the magnetic portion 302, the magnetic sensor 303 may recognize a magnet value as a binary code of '010'. Since the binary code of '010' is converted into a decimal code of '2', the waist size sensor 112 may recognize that the user is using the second hole 3013 that corresponds to the decimal code of '2'. The waist size sensor 112 may determine a length of 87 cm based on the overall length of the belt portion and a location of the second hole as the waist size of the user. In this case, an interval between the first and second holes 3011 and 3013 is 2 cm.

According to an exemplary embodiment, the magnetic sensor 303 may operate as a sensor that detects an attachment or detachment of the smart belt 100. For example, when the user takes off the smart belt 100, the magnetic sensor 303 no longer senses a magnet. When no magnet is sensed, the magnetic sensor 303 may recognize a magnet value as a binary code of '000' and transmit the binary code of '000' to the controller 120. When the controller 120 receives the binary code of '000' from the magnetic sensor 303, the controller 120 may determine that the user has taken off the smart belt 100.

The tension sensor 113 may measure, for example, a tension applied to the smart belt 100 or a variation of the applied tension. As described above with reference to FIGS. 2A and 2B, the tension sensor 113 may include, but is not limited to, the FSR sensor 102 and/or the strain gauge 106.

The tension sensor 113 may measure the tension of the smart belt 100 by measuring not only a resistance change of the smart belt 100 but also a change in an electrostatic capacity, a change in an intensity of magnetism, a change in a natural vibration frequency, a change in a restoration force, and the like of the smart belt 100. The tension sensor 113 has been described above with reference to FIGS. 2A and 2B, and thus a repeated description thereof will be omitted.

According to an exemplary embodiment, when the tension sensor 113 measures a tension of the smart belt 100 or a variation of the tension, the tension sensor 113 may transmit tension information (for example, a tension value and/or a variation of the tension) to the controller 120.

The controller 120 may drive an operating system (OS) or an application program to control a plurality of hardware and/or software components connected to the controller 120, and may perform various data processing and/or calculations.

For example, the controller 120 may control at least one of the inertia sensor 111, the waist size sensor 112, and the tension sensor 113 to acquire at least one of the motion information of the user, the waist size information of the user, and the tension information of the smart belt 100. The controller 120 may also control the communicator 130 to receive or transmit data from or to the external host terminal 200.

When the user who wears the smart belt 100 adopts a certain posture, for example, sitting or lying or stretching the user's abdominal muscle during when the waist size sensor 112 measures the waist size of the user, the measured waist size may not be accurate. Thus, the controller 120 of the smart belt 100 may control the waist size sensor 112 to measure a waist size when the user stands upright without recognizing that the waist size is being measured. The controller 120 may correct the waist size of the user measured by the waist size sensor 112, based on the tension information of the smart belt 100.

An operation, performed by the smart belt 100, of measuring a waist size of a user in consideration of a motion of the user and correcting the measured waist size by using the tension information of the smart belt 100 will now be described in detail with reference to FIG. 4.

Figure 4:
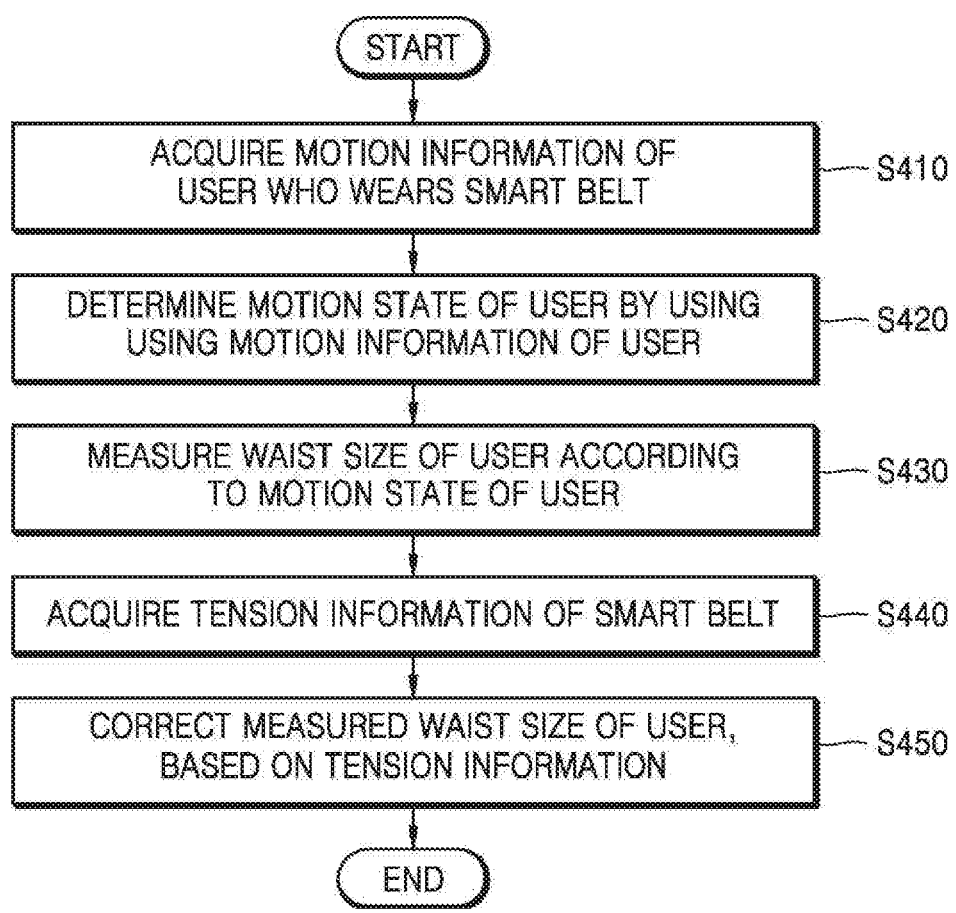
FIG. 4 is a flowchart of a waist size measuring and correcting method according to an exemplary embodiment.

FIG. 4 is a flowchart of a waist size measuring and correcting method according to an exemplary embodiment.

In operation S410, the smart belt 100 may acquire motion information of a user who wears the smart belt 100.

According to an exemplary embodiment, the smart belt 100 may determine whether a user is wearing the smart belt 100, by using at least one sensor. For example, the smart belt 100 may determine whether the user has worn or taken off the smart belt 100, by using the optical sensor, the proximity sensor, the pressure sensor, the tension sensor 113, an illuminance sensor, the magnetic sensor, or the like. For example, when a tension value measured by the tension sensor 113 is equal to or greater than a certain value, the smart belt 100 may determine that the user is wearing the smart belt 100.

According to an exemplary embodiment, the smart belt 100 may more accurately determine whether the user wears the smart belt 100, by combining pieces of information obtained by using a plurality of sensors.

According to an exemplary embodiment, when it is determined that the user is wearing the smart belt 100, the smart belt 100 may sense a motion of the user by using the inertia sensor 111. For example, the smart belt 100 may acquire a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor.

According to an exemplary embodiment, the smart belt 100 may acquire motion information of the user at certain intervals. For example, the smart belt 100 may acquire the motion information of the user at intervals of 10 minutes.

Alternatively, the smart belt 100 may acquire the motion information of the user at a predefined time. For example, the smart belt 100 may acquire the motion information of the user between 7:00 A.M. and 8:00 A.M. during which the user usually goes to work, between 12:00 P.M. and 1:00 P.M. during which the user usually has lunch, or between 7 P.M. and 8:00 P.M. during which the user usually gets off work. According to an exemplary embodiment, the predefined time may be changed according to a user input or user profile information of the user, which will be described in detail later.

In operation S420, the smart belt 100 may determine a motion state of the user by using the motion information of the user.

The motion state of the user may include, but is not limited to, a walking state, a standing state (an upright-standing state or an a slant-standing state), a stair-ascending or descending state, a running state, a sleeping state, a driving state, a commuting state, a speaking state (or a state in conversation), a workout (for example, jogging, swimming, tennis, baseball, and hiking) state, a drinking state, a sitting state, and a lying state.

The smart belt 100 may determine whether the user is in a stopped state, a walking state, or a running state, by using at least one of an acceleration value, an inclination value, a position value, and a pressure value. For example, by using acceleration information measured by the acceleration sensor, the smart belt 100 may determine that the user is in a stopped state, when the user has moved at an average speed of 0.001 km/h for a certain period of time, may determine that the user is walking, when the user moves at an average speed of 4 km/h for a certain period of time, and may determine that the user is running, when the user moves at an average speed of 15 km/h for a certain period of time.

The smart belt 100 may also determine, by using location variation information measured by the position sensor, whether the user is in a stopped state (for example, a location variation<a first threshold value), in a walking state (for example, the first threshold value≤the location variation<a second threshold value), or in a running state (for example, the second threshold value≤the location variation).

According to an exemplary embodiment, the smart belt 100 may determine the motion state of the user by using the user profile information of the user. The user profile information may be stored in a personal server of the user, the host terminal 200, or the smart belt 100.

For example, the smart belt 100 may determine the motion state of the user by using schedule information or lifestyle information of the user. If the user moves a certain distance or greater from home to a specific location (for example, the user's workplace) at 8 A.M. on weekdays, the smart belt 100 may manage information on a commute time of the user, information on a commute distance of the user, and information on a location of the user's workplace as the user profile information. For example, when a current time is 8:20 A.M. on Monday and a current location is near a subway station, the smart belt 100 may determine that the user is on his or her way to work.

When an average moving speed of the user is below a certain threshold (e.g., 0.0001 km/h) for a certain period of time and the user is located in an office for a certain period of time, the smart belt 100 may determine that the user is working.

According to an exemplary embodiment, the smart belt 100 may analyze the motion state of the user by using biometric information measured by an external wearable device. A wearable device according to an exemplary embodiment may be, but is not limited to, a ring, a necklace, a band, a watch, shoes, an ear ring, a hair band, clothing, gloves, or a thimble.

For example, the smart belt 100 may receive pulse rate information, blood pressure information, heart rate information, body temperature information, and the like measured by the external wearable device. At this time, the smart belt 100 may receive the biometric information from the external wearable device via the host terminal 200, or receive the biometric information directly from the external wearable device. When an average pulse rate of the user is equal to or greater than a certain frequency for a certain period of time, the smart belt 100 may determine that the user is exercising.

According to an exemplary embodiment, the smart belt 100 may determine whether the user is in a stopped state, a walking state, a running state, a hiking state, or the like, by using acceleration information, pressure information, height information, or the like measured by a sneaker or a shoe insert. For example, when a moving speed of the user is equal to or greater than a certain value and a pressure pattern of a sole measured by a pressure sensor attached to a sneaker is similar to a pattern corresponding to hiking, the smart belt 100 may determine that the user is hiking.

The smart belt 100 may identify a state when a user stands up from a sitting position or a state when a user sits down from a standing position, by using tension information. For example, when a tension of the smart belt 100 increases, the smart belt 100 may determine that the user sits down from a standing position. When a tension of the smart belt 100 decreases, the smart belt 100 may determine that the user stands up from a sitting position.

In operation S430, the smart belt 100 may measure the waist size of the user according to the motion state of the user. For example, when a measurement value of at least one of the acceleration sensor, the tension sensor, the respiration sensor, and the gyroscope sensor corresponds to a certain range, the smart belt 100 may measure the waist size of the user by measuring the length between first and second points of the smart belt 100.

According to an exemplary embodiment, the smart belt 100 may determine a time to measure the waist size of the user (or waist size measurement time), based on the motion state of the user. For example, since a waist size is generally measured when a user is stably standing, the smart belt 100 may determine, as the waist size measurement time, a time point when the moving speed of the user is less than a certain speed (for example, 0.1 km/h). Alternatively, the smart belt 100 may determine, as the waist size measurement time, a time point when it is determined that the user is at an upright-standing posture (or in an upright-standing quiver state).

According to an exemplary embodiment, when arrival of the time to measure the waist size of the user is determined, the smart belt 100 may activate the waist size sensor 112 to measure the waist size of the user.

On the other hand, when the moving speed of the user is equal to or greater than the certain speed or it is determined that the user is in a sitting state, the smart belt 100 may determine not to measure the waist size. The smart belt 100 may maintain the waist size sensor 112 in a non-active state.

The waist size sensor 112 of the smart belt 100 may measure the waist size of the user who wears the smart belt 100. For example, the waist size sensor 112 of the smart belt 100 may measure the waist size of a user by using the optical sensor, according to an incremental linear encoder method, an absolute linear encoder method, an incremental rotary encoder method, or an absolute rotary encoder method. The waist size sensor 112 of the smart belt 100 may measure the waist size of the user by using the image sensor or the magnetic field sensor. A method in which the waist size sensor 112 of the smart belt 100 measures the waist size of the user has been described above with reference to FIGS. 3A and 3B, and thus a detailed description thereof will be omitted.

According to an exemplary embodiment, the smart belt 100 may acquire a first waist size value corresponding to a first motion state of the user by measuring a waist size of the user in the first motion state. When the first motion state is not a predefined reference state for measuring the waist size, the smart belt 100 may convert the first waist size value corresponding to the first motion state into a second waist size value corresponding to the predefined reference state. The predefined reference state may be, but is not limited to, an upright-standing quiver state.

For example, when the smart belt 100 acquires the first waist size value of the user by measuring a waist size of the user in a slantingly-standing state, the first waist size value may be different from an actual waist size of the user. Accordingly, the smart belt 100 may convert the first waist size value into a second waist size value corresponding to the upright-standing quiver state, by using human body modeling information of the user.

The human body modeling information of the user may be information representing a result of analyzing a relationship between the posture and the waist size of the user by using a machine learning technique. For example, the human body modeling information of the user may include, but is not limited to, a difference between waist sizes in a sitting state and in a standing state, a difference between waist sizes in an upright-standing state and in a slantingly-standing state, a difference between waist sizes in a standing state and in a walking state, and a difference between waist sizes before and after eating. In operation S440, the smart belt 100 may acquire the tension information of the smart belt 100 by using the tension sensor 113.

For example, the smart belt 100 may measure the tension of the smart belt 100 by using the FSR sensor 102 or the strain gauge 106, but the inventive concept is not limited thereto. A method in which the smart belt 100 measures a tension has been described above with reference to FIGS. 2A and 2B, and thus a repeated description thereof will be omitted.

According to an exemplary embodiment, the smart belt 100 may periodically acquire the tension information of the smart belt 100 by using the tension sensor 113. For example, the smart belt 100 may acquire the tension information at intervals of 10 minutes.

The smart belt 100 may acquire the tension information at a predefined time. For example, the smart belt 100 may acquire the tension information of the smart belt 100 between 7 A.M. and 8 A.M. during which the user goes to work, between 12:00 P.M. and 1:00 P.M. during which the user has lunch, or between 7:00 P.M. and 8:00 P.M. during which the user has dinner. The predefined time may be changed according to a user input or user profile information of the user.

According to an exemplary embodiment, the smart belt 100 may acquire the tension information when a specific event occurs. For example, when an event in which the waist size sensor 112 measures the waist size of the user occurs, the smart belt 100 may activate the tension sensor 113 to measure a tension value of the smart belt 100.

According to an exemplary embodiment, the smart belt 100 may correct the tension value measured by the tension sensor 113, according to the motion state of the user. For example, when the first tension value is measured when the user is standing slantingly, the smart belt 100 may correct the measured first tension value to a tension value when the user is in an upright-standing quiver state. An operation, performed by the smart belt 100, of correcting a tension value will be described in detail later with reference to FIG. 8.

In operation S450, the smart belt 100 may correct the measured waist size of the user, based on the tension information. For example, the smart belt 100 may correct the measured waist size (or length) by using the measured tension and stored reference tension information. The reference tension information may include a tension-based standard table.

In the tension-based standard table, a tension is matched with a waist size correction value. According to an exemplary embodiment, the waist size correction value included in the tension-based standard table may be calculated by taking into account body information (for example, a gender, an age, a height, and a weight) of the user.

For example, according to the tension-based standard table, when a tension is 100 g, a waist size correction value is '0', and, as the tension increases from 100 g, the waist size correction value may increase. For example, when the tension is 400 g, the waist size correction value may be '+2 cm', and, when the tension is 700 g, the waist size correction value may be '+4 cm'.

An increase in a tension denotes an increase in a waist tightening force of the smart belt 100, and thus an increased tension causes a measured waist size to be smaller than the actual waist size.

For example, when the length of the smart belt 100 is not adjusted although the belly of the user further protrudes due to overeating than before eating, the waist size of the user measured by the smart belt 100 may remain the same before and after eating. However, in reality, the waist size after eating may be greater than the waist size before eating. Accordingly, the smart belt 100 may accurately predict a current waist size of the user by adding a waist size correction value corresponding to an increased tension value to an actually-measured waist size value, by using the tension-based standard table.

According to an exemplary embodiment, some of operations S410-S450 may be omitted, some of additional operations may be further included, or the order of some of operations S410-S450 may be changed.

An operation, performed by the smart belt 100, of providing accurate waist size information to a user by taking into account a tension of the smart belt 100 will now be described in more detail with reference to FIGS. 5, 6, 7A and 7B.

FIG. 5 is a view for explaining operations of a motion detection module 510 and a posture detection module 520 according to an exemplary embodiment.

Referring to FIG. 5, the controller 120 of the smart belt 100 may determine a waist size measurement time by using the motion detection module 510 and the posture detection module 520.

For example, when an acceleration variation between a current acceleration value A1 and a previous acceleration value A0 (i.e., a difference (A1−A0) between the acceleration variations A1 and A0) is no less than 0 and no more than a threshold value, the motion detection module 510 may determine that the user is in a non-moving state (e.g., substantial number of steps==0). The motion detection module 510 may transmit to the controller 120 information representing that the user is in a non-moving state. Since the user is in a not-moving state, the controller 120 may control the waist size sensor 112 to measure the waist size of the user. On the other hand, when the motion detection module 510 determines that the user is moving (e.g., substantial number of steps≥1), the controller 120 may deactivate the waist size sensor 112 not to measure the waist size of the user.

The posture detection module 520 may determine the posture of the user by using, for example, an acceleration variation measured by the acceleration sensor and/or a tension sensor value measured by the tension sensor 113. For example, when the acceleration variation is greater than a minimum threshold value and the tension sensor value is less than a tension threshold value, the posture detection module 520 may determine that the user is at a standing posture.

When it is determined that the user is at a standing posture, the posture detection module 520 may determine whether it is appropriate to currently measure the waist size of the user, by using a gyroscope sensor value measured by the gyroscope sensor. For example, when the user is in a standing state and the gyroscope sensor value is within a threshold range (Th0≤G≤Th1), the posture detection module 520 may determine that the current state of the user allows accurate measurement of the waist size. A state of a user that allows accurate measurement of the waist size of the user will now be described in more detail with reference to FIG. 6.

Figure 6:
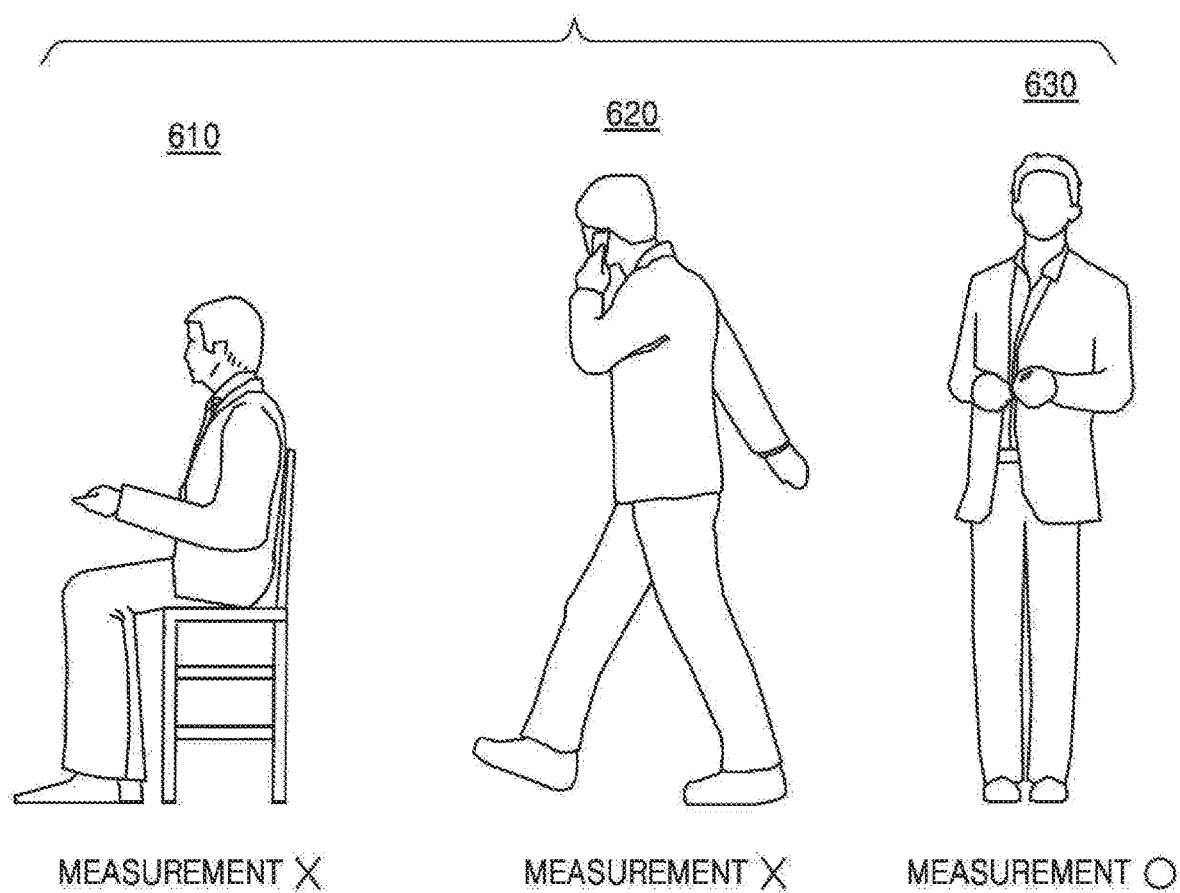
FIG. 6 is a view for explaining an operation of measuring a waist size of a user according to a motion state of a user.

FIG. 6 is a view for explaining an operation of measuring the waist size of a user according to a motion state of the user.

According to an exemplary embodiment, the smart belt 100 may determine the motion state of the user, based on information acquired by the inertia sensor 111 or the tension sensor 113. For example, the smart belt 100 may determine whether the user is in a sitting state 610, a walking state 620, or a standing state 630, by using acceleration information, inclination information, tension information, or the like.

According to an exemplary embodiment, when the smart belt 100 determines that the user is in the sitting state 610 or the walking state 620, the smart belt 100 may determine that the current state of the user is inadequate to measure the waist size of the user, and may not measure the waist size of the user.

In general, the waist size of a user increases when the user is sitting, compared with when the user is standing. Thus, it is difficult to accurately measure the waist size of the user when the user is in the sitting state 610. When a user is moving, the waist size of the user continuously changes. Thus, it is difficult to accurately measure the waist size of the user when the user is in the walking state 620.

On the other hand, when the smart belt 100 determines that the user is in the stably-standing state 630 without substantial movement, the smart belt 100 may measure the waist size of the user by using the waist size sensor 112.

Figure 7A:
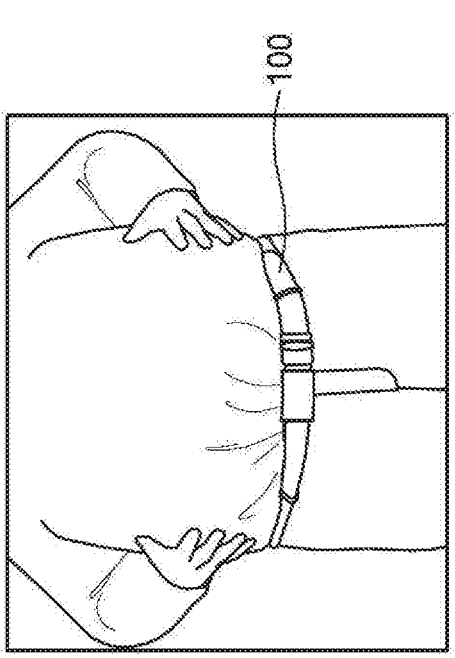
FIG. 7A is a view for explaining a size correction algorithm according to an exemplary embodiment.

FIG. 7A is a diagram for explaining a size correction algorithm 700 according to an exemplary embodiment.

Referring to FIG. 7A, the smart belt 100 may correct a waist size value measured by the waist size sensor 112, by using the size correction algorithm 700. The size correction algorithm 700 may correct an error of an actually measured waist size, based on a tension-based standard table or body modeling information. In an exemplary embodiment, according to the tension-based standard table, when a tension is 100 g, a waist size correction value is '0', and, as the tension increases from 100 g, the waist size correction value may also increase.

For example, when the waist size value measured by the waist size sensor 112 is 81.5 cm and a tension value measured by the tension sensor 113 is 720 g, the smart belt 100 may correct the measured waist size of 81.5 cm to 85 cm by using the tension-based standard table. The corrected waist size of 85 cm may more accurately represent the actual waist size of the user.

Figure 7B:
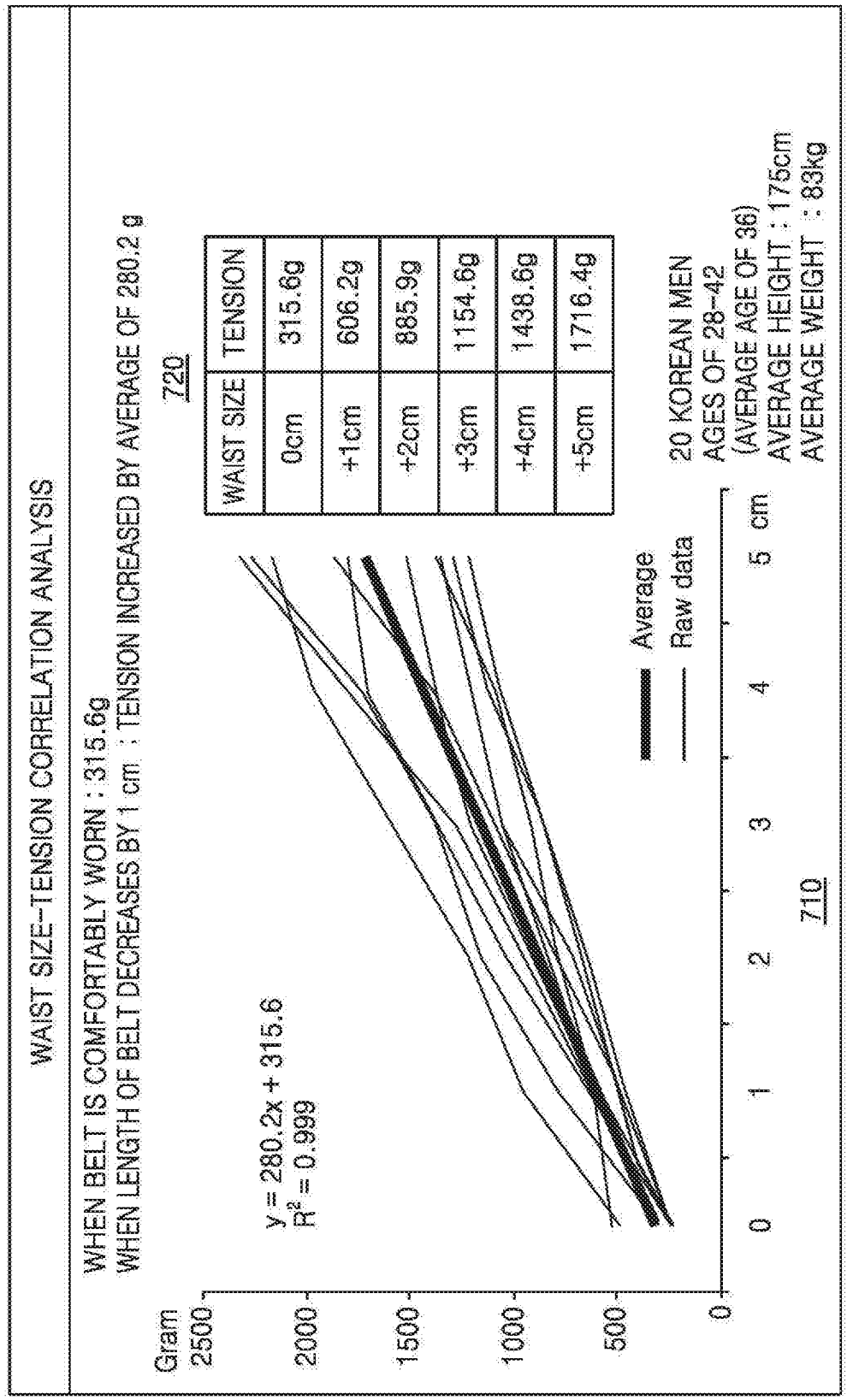
FIG. 7B is a view for explaining a tension-based standard table according to an exemplary embodiment.

The tension-based standard table will now be described in more detail with reference to FIG. 7B. FIG. 7B illustrates experimental data representing a result of analyzing a correlation between a waist size and a tension. Referring to a waist size-tension graph 710, a tension increase rate (or a rate at which tension of a belt increases) when the belt is tightened to decrease the length of a belt by 1 cm was tested on 20 Korean men having an average height of 175 cm, an average weight of 83 kg, and an average age of 36. As a result, it was found that a tension increases by an average of 280.2 g when the length of the belt decreases by 1 cm.

A tension-based standard table 720 may be generated using the experimental data (or the waist size-tension graph 710), as shown in FIG. 7B. According to the tension-based standard table 720, when a tension is 315.6 g, a waist size correction value may be '0'. When the tension is 606.2 g, the waist size correction value may be '+2 cm'. When the tension is 1154.6 g, the waist size correction value may be '+3'.

Since the waist size-tension graph 710 and the tension-based standard table 720 of FIG. 7B are experimental data obtained under a specific condition, when a body condition, an age, and the like of a test object are changed, the waist size-tension graph 710 and the tension-based standard table 720 may also be changed. According to an exemplary embodiment, a plurality of tension-based standard tables 720 may be generated based on experimental data respectively obtained according to different conditions, and a tension-based standard table 720, among the plurality of tension-based standard tables 720, corresponding to a user's condition may be used.

According to an exemplary embodiment, the smart belt 100 may correct the waist size measured by the waist size sensor 112, by using human body modeling information. For example, the smart belt 100 may correct the waist size measured by the waist size sensor 112, by further taking into account at least one of body information (for example, a height and a weight), gender information (for example, a male), and age information (for example, an age of 46) of the user.

According to an exemplary embodiment, the human body modeling information may include information representing a result of analyzing a relationship between at least one of the body information, gender, and age of the user and the waist size of the user by using a machine learning technique. For example, the human body modeling information may include, but is not limited to, a waist size correction value according to the body information, a waist size correction value according to the age, a waist size correction value according to the gender, a waist size correction value according to the body information and a tension, a waist size correction value according to the age and the tension, and a waist size correction value according to the gender and the tension.

The smart belt 100 may correct the tension value measured by the tension sensor 113 by using the human body modeling information, and may correct the waist size measured by the waist size sensor 112 by using the corrected tension value. An operation, performed by the smart belt 100, of correcting a tension value according to the human body modeling information will now be described in more detail with reference to FIG. 8.

Figure 8:
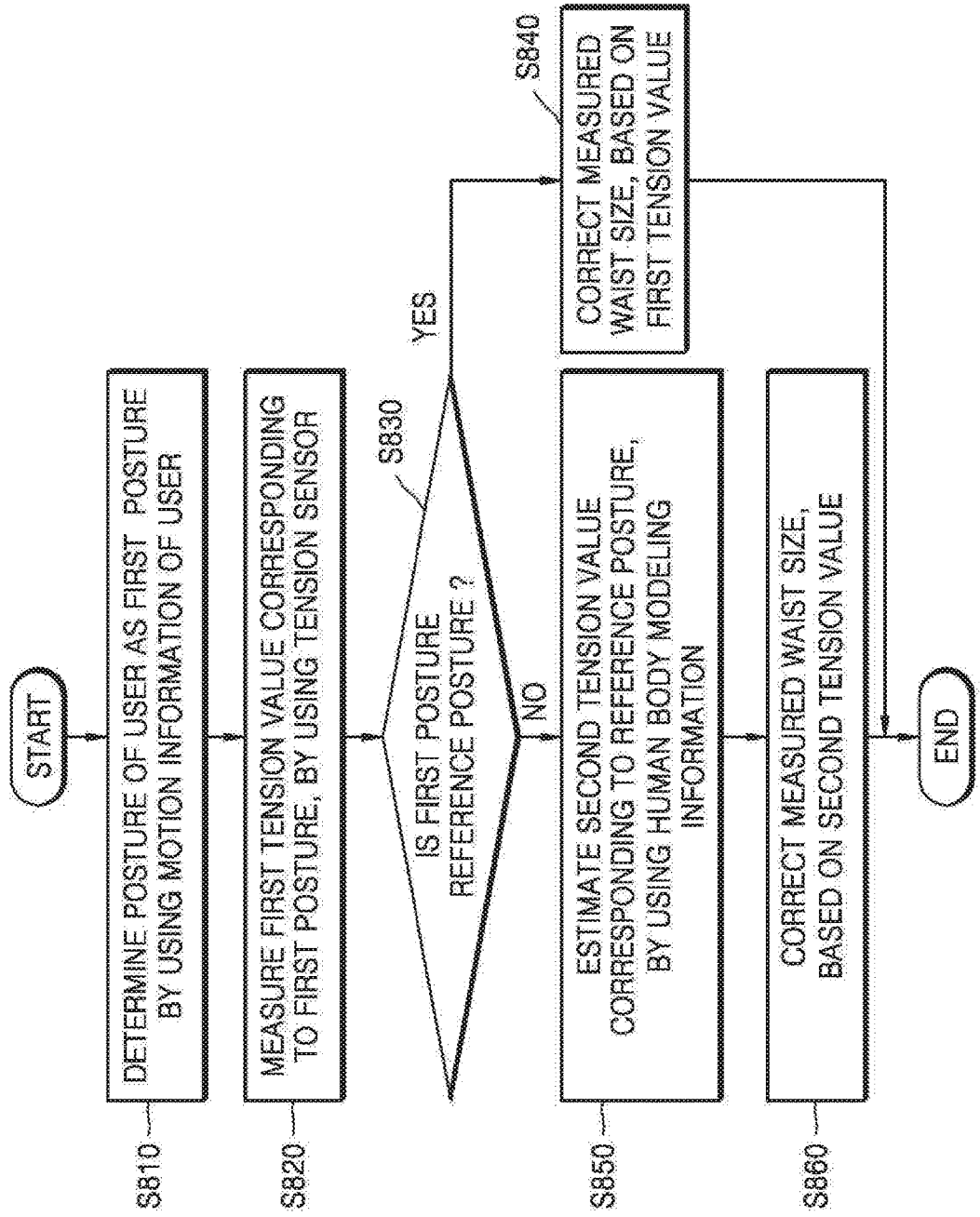
FIG. 8 is a flowchart of a method of correcting a tension value according to a posture of a user, according to an exemplary embodiment.

FIG. 8 is a flowchart of a method of correcting a tension value according to the posture of a user, according to an exemplary embodiment.

In operation S810, the smart belt 100 may determine a posture of the user as a first posture by using motion information of the user.

The posture of the user may include, but is not limited to, a walking posture, a standing posture (e.g., an upright-standing posture or an a slant-standing posture), a stair-ascending or descending posture, a running posture, a driving posture, a speaking posture, a workout (for example, jogging, swimming, tennis, baseball, and hiking) posture, a sitting posture, and a lying posture.

The smart belt 100 may determine whether the user is standing, walking, or running, by using at least one of an acceleration value, an inclination value, a position value, and a pressure value. For example, by using acceleration information measured by the acceleration sensor, the smart belt 100 may determine that the user is in a standing state when the user has moved at an average speed of 0.001 km/h for a certain period of time, may determine that the user is walking when the user moves at an average speed of 4 km/h for a certain period of time, and may determine that the user is running when the user moves at an average speed of 15 km/h for a certain period of time.

When the smart belt 100 determines that the user is standing, the smart belt 100 may also determine whether the user is standing at an angle or upright, by using the gyroscope sensor.

In operation S820, the smart belt 100 may measure a first tension value corresponding to the first posture, by using the tension sensor.

For example, the smart belt 100 may measure the first tension value of the smart belt 100 at the first posture, by using the FSR sensor 102 or the strain gauge 106. A method in which the smart belt 100 measures a tension has been described above with reference to FIGS. 2A and 2B, and thus a repeated description thereof will be omitted.

In operation S830, the smart belt 100 may determine whether the first posture is a reference posture. The reference posture is a posture that is pre-defined to be adequate to measure a waist size, and may be, for example, a standing-upright posture (e.g., a standing-upright quiver posture).

For example, when the first posture is a slantingly-standing posture, the smart belt 100 may determine that the first posture is not the reference posture. On the other hand, when the first posture is a standing-upright posture, the smart belt 100 may determine that the first posture is the reference posture.

In operation S840, when the first posture is the reference posture, the smart belt 100 may correct a measured waist size, based on the first tension value corresponding to the first posture.

For example, when the first posture is a standing-upright posture, the first tension value measured at the first posture may be a tension value adequate to be used to correct a waist size. Accordingly, the smart belt 100 may correct the waist size measured by the waist size sensor 112, by using the first tension value measured at the first posture.

In operation S850, when it is determined that the first posture is not the reference posture, the smart belt 100 may estimate a second tension value corresponding to the reference posture, by using the human body modeling information.

For example, when the first posture is a slantingly-standing posture, the first tension value measured at the first posture may not be an accurate tension value that may be used to correct the waist size. Accordingly, the smart belt 100 may convert the first tension value into the second tension value corresponding to the reference posture (e.g., standing-upright quiver posture). At this time, the smart belt 100 may convert the first tension value into the second tension value according to the human body modeling information.

The human body modeling information may include tension correction values according to postures of the user. For example, according to the human body modeling information, a tension correction value corresponding to the sitting posture may be '−100 g', and a tension correction value corresponding to the slantingly-standing posture may be '−10 g'.

In operation S860, the smart belt 100 may correct the measured waist size of the user, based on the second tension value. Since operation S860 corresponds to operation S450 of FIG. 4, a repeated description thereof will be omitted.

An operation, performed by the smart belt 100, of correcting a tension value according to postures of a user will now be described in more detail with reference to FIG. 9.

Figure 9:
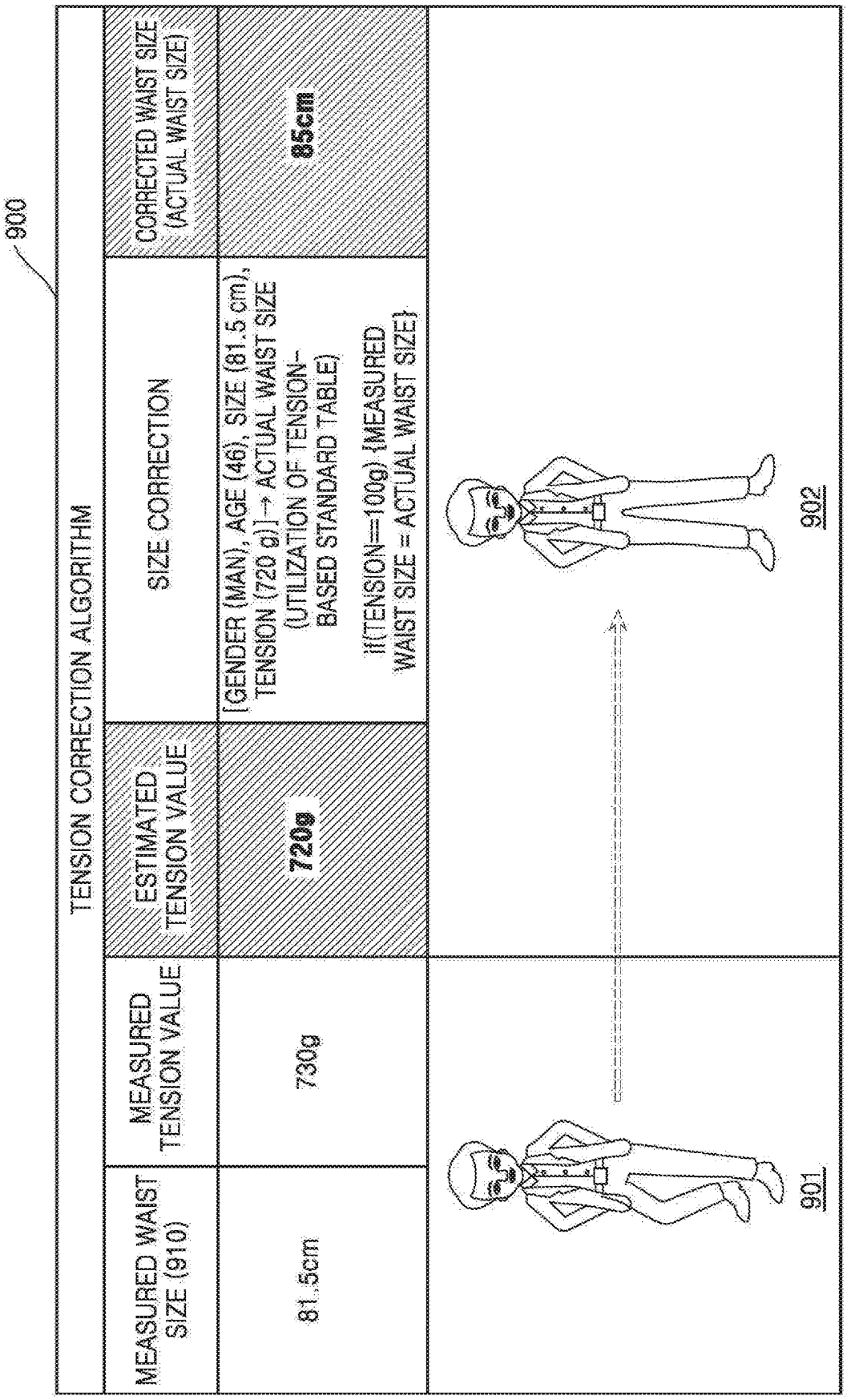
FIG. 9 is a view for explaining a tension correction algorithm according to an exemplary embodiment.

FIG. 9 is a view for explaining a tension correction algorithm 900 according to an exemplary embodiment.

Referring to FIG. 9, the smart belt 100 may correct the tension value measured by the tension sensor 113, by using the tension correction algorithm 900. The tension correction algorithm 900 may correct an error of a tension value according to postures of a user.

For example, when a tension value of the smart belt 100 measured in a state 901 where the user is standing slantingly is 730 g, the smart belt 100 may convert the measured tension value of 730 g into an estimated tension value of 720 g) corresponding to a standing-upright state 902 by using the human body modeling information.

The smart belt 100 may correct a waist size value measured in the state 901 where the user is standing slantingly, based on the corrected tension value (for example, 720 g). For example, when the waist size value measured by the waist size sensor 112 is 81.5 cm and the corrected tension value is 720 g, the smart belt 100 may correct the measured waist size of 81.5 cm to 85 cm by using the tension-based standard table. The corrected waist size value of 85 cm may be the same or similar to an actual waist size of the user measured in the standing-upright state 902.

According to an exemplary embodiment, the smart belt 100 may measure the waist size of the user, based on respiration information of the user. A method in which the smart belt 100 determines a waist size measurement time based on respiration information of a user will now be described with reference to FIG. 10.

Figure 10:
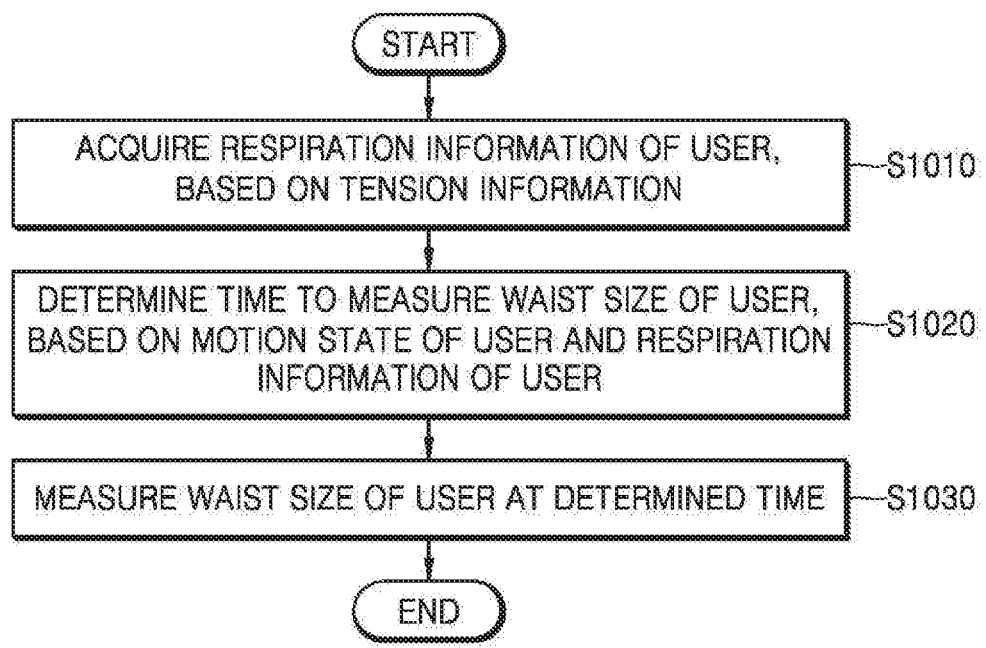
FIG. 10 is a flowchart of a method of determining a waist size measurement time based on respiration information of a user, according to an exemplary embodiment.

FIG. 10 is a flowchart of a method of determining a waist size measurement time based on the respiration information of a user, according to an exemplary embodiment.

In operation S1010, the smart belt 100 may acquire the respiration information of the user, based on tension information. For example, the smart belt 100 may sense a variation of a tension value, a change cycle of the tension value, a maximum tension value, a minimum tension value, and the like, by using the tension sensor 113.

The smart belt 100 may determine a breathing rate of the user per minute, based on, for example, the variation of the tension value and/or the change cycle of the tension value.

Referring to FIG. 11, a respiration detection module 1100 of the smart belt 100 may detect a breathing cycle, based on the variation of the tension value. The respiration detection module 1100 of the smart belt 100 may determine whether the detected breathing cycle is a stable breathing cycle. For example, when the breathing cycle is 3 to 5 seconds and the breathing rate per minute is 12 to 20 times, the smart belt 100 may determine that breathing of the user is stable.

On the other hand, when the breathing cycle is less than 3 seconds and the breathing rate per minute exceeds 20 times, the smart belt 100 may determine that breathing of the user is unstable.

Referring back to FIG. 10, in operation S1020, the smart belt 100 may determine a time to measure the waist size of the user, based on the motion state of the user and the respiration information of the user. In operation S1030, the smart belt 100 may measure the waist size of the user at the determined time.

According to an exemplary embodiment, the smart belt 100 may determine, as the waist size measuring time, a time point when the user is standing upright and respiration of the user is determined to be stable. Accordingly, when the user is standing upright and respiration of the user is determined to be stable, the smart belt 100 may activate the waist size sensor 112 to measure the waist size of the user.

On the other hand, when respiration of the user is determined to be unstable because the user is in a running state, the smart belt 100 may determine to measure the waist size of the user at a later time, and may not measure the waist size of the user at a current time point. Immediately after the user stopped running, the smart belt 100 may determine that respiration of the user is unstable even when the user is in a standing state, and may determine to measure the waist size of the user at a later time.

Exemplary embodiments of determining the waist size measuring time according to the motion state of the user and measuring the waist size at the determined waist size measuring time have been described above with reference to FIGS. 4-11. An exemplary embodiment of measuring the waist size of the user and correcting the measured waist size according to the motion state of the user will now be described with reference to FIG. 12.

Figure 12:
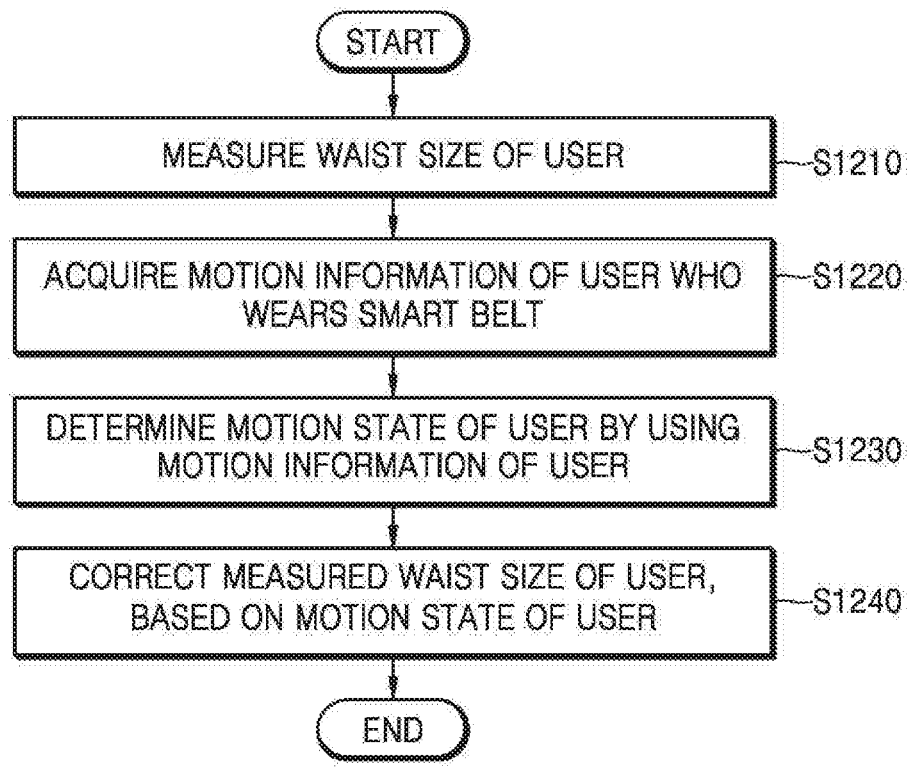
FIG. 12 is a flowchart of a method of correcting a waist size of a user based on a motion state of a user, according to an exemplary embodiment.

FIG. 12 is a flowchart of a method of correcting a waist size of a user based on a motion state of the user, according to an exemplary embodiment.

In operation S1210, the smart belt 100 may measure the waist size of the user.

According to an exemplary embodiment, the smart belt 100 may measure the waist size of a user who wears the smart belt 100, by using the waist size sensor 112. For example, the smart belt 100 may measure the waist size by using an optical sensor, according to at least one of an incremental linear encoder method, an absolute linear encoder method, an incremental rotary encoder method, and an absolute rotary encoder method. The smart belt 100 may measure the waist size of the user by using the image sensor or the magnetic field sensor. A method in which the waist size sensor 112 of the smart belt 100 measures the waist size of the user has been described above with reference to FIGS. 3A and 3B, and thus a detailed description thereof will be omitted.

In operation S1220, the smart belt 100 may acquire motion information of the user who wears the smart belt 100. For example, the smart belt 100 may acquire the motion information of the user at a time point when the waist size of the user is measured.

According to an exemplary embodiment, the smart belt 100 may sense a motion of the user by using the inertia sensor 111. For example, the smart belt 100 may acquire a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor. The smart belt 100 may acquire the tension information of the smart belt 100 by using the tension sensor 113.

In operation S1230, the smart belt 100 may determine a motion state of the user by using the motion information of the user.

According to an exemplary embodiment, the smart belt 100 may determine whether the user is in a stopped state, a walking state, or a running state, by using at least one of an acceleration value, an inclination value, a position value, and a pressure value. For example, by using acceleration information measured by the acceleration sensor, the smart belt 100 may determine that the user is in a stopped state when the user has moved at an average speed of 0.001 km/h for a certain period of time, may determine that the user is walking when the user moves at an average speed of 4 km/h for a certain period of time, and may determine that the user is running when the user moves at an average speed of 15 km/h for a certain period of time. Even when the smart belt 100 determines that the user is standing, the smart belt 100 may also determine whether the user is standing at an angle or upright, by using the gyroscope sensor.

According to an exemplary embodiment, the smart belt 100 may determine whether the user is sitting, standing, or lying, by using the tension information acquired by the tension sensor 113. A tension value may be greater when the user is sitting than when the user is standing, and a respiration signal may be more smoothly detected when the user is sitting than when the user is standing.

In operation S1240, the smart belt 100 may correct the measured waist size of the user, based on the motion state of the user. For example, when the motion state of the user at a time of measuring the waist size is not a predefined reference state, the smart belt 100 may correct the measured waist size. The predefined reference state may be, but is not limited to, an upright-standing quiver state.

According to an exemplary embodiment, the smart belt 100 may acquire a first waist size value corresponding to a first motion state of the user by measuring a waist size of the user in the first motion state, and may convert the first waist size value corresponding to the first motion state into a second waist size value corresponding to the predefined reference state.

For example, when a waist size in a sitting state is measured, the smart belt 100 may convert the waist size measured in the sitting state into a waist size in the reference state, by using the human body modeling information. The human body modeling information may include information representing a result of analyzing waist size values respectively corresponding to motion states of the user. If the waist size value measured in a sitting state is 82 cm, the smart belt 100 may convert the measured waist size value of 82 cm into a waist size value 77 cm corresponding to the reference state by using the human body modeling information.

Figure 13:
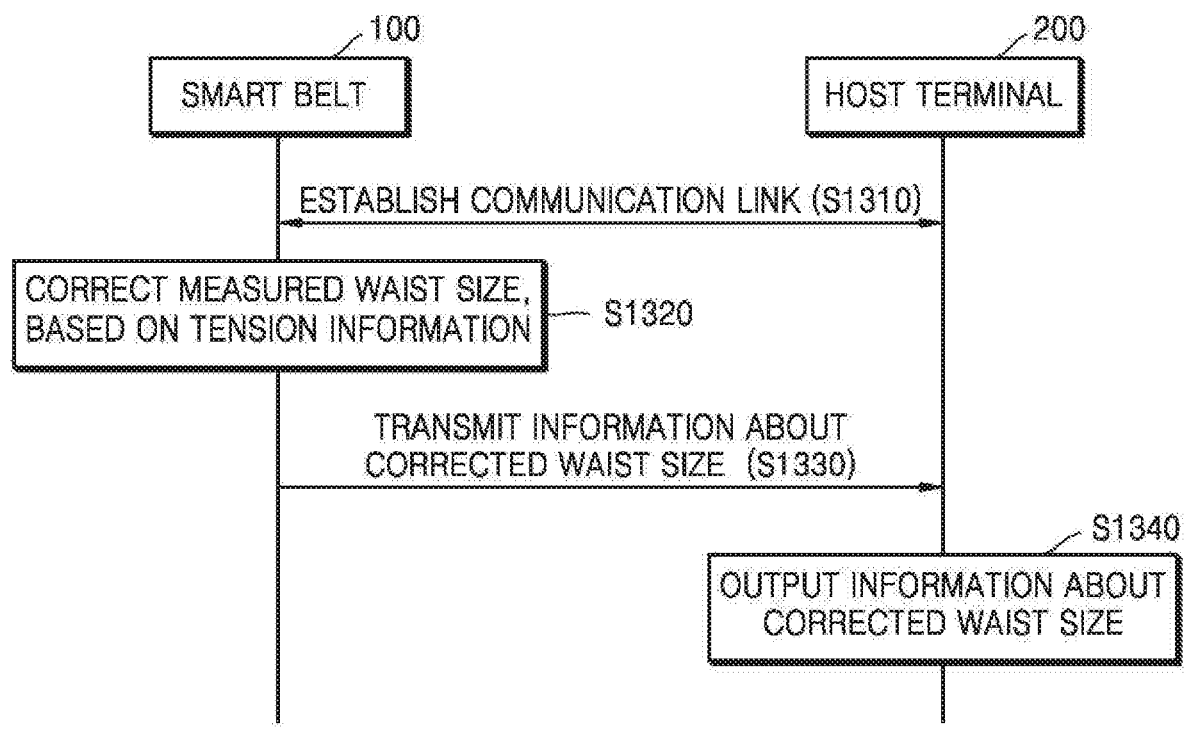
FIG. 13 is a flowchart of a method in which a smart belt transmits information about a corrected waist size to a host terminal, according to an exemplary embodiment.

FIG. 13 is a flowchart of a method in which a smart belt transmits information about a corrected waist size to a host terminal, according to an exemplary embodiment.

In operation S1310, the smart belt 100 and the host terminal 200 may establish a communication link.

For example, the smart belt 100 may establish a local area communication link and/or may establish a mobile communication link (for example, third generation (3G), fourth generation (4G), or fifth generation (5G) with the host terminal 200. Examples of the local area communication may include, but is not limited to, Bluetooth, Bluetooth Low Energy (BLE), Wi-Fi Direct, ultra wideband (UWB), Zigbee, Near Field Communication (NFC), and Ant+.

In operation S1320, the smart belt 100 may measure the waist size of a user, and correct the measured waist size, based on tension information. Since operation S1320 corresponds to operations S410-S450 of FIG. 4, a repeated description thereof will be omitted.

In operation S1330, the smart belt 100 may transmit information about a corrected waist size to the host terminal 200. The information about the corrected waist size may include, but is not limited to, a waist size value and a waist size variation.

According to an exemplary embodiment, the smart belt 100 may periodically transmit the information about the corrected waist size to the host terminal 200. For example, the smart belt 100 may transmit the information about the corrected waist size to the host terminal 200 once an hour.

According to an exemplary embodiment, when the smart belt 100 receives a request from the host terminal 200, the smart belt 100 may periodically transmit the information about the corrected waist size to the host terminal 200. For example, when the host terminal 200 receives from the user an input of executing a health care application, the host terminal 200 may request the smart belt 100 to transmit the information about the waist size. In this case, the smart belt 100 may transmit the information about the corrected waist size to the host terminal 200.

According to an exemplary embodiment, the smart belt 100 may transmit the information about the corrected waist size to the host terminal 200 when a preset event occurs. For example, every time an event where the waist size of the user increases by 1 cm occurs, the smart belt 100 may transmit the information about the waist size to the host terminal 200. Alternatively, when an event where the user arrives at home occurs, the smart belt 100 may transmit the information about the waist size to the host terminal 200. At this time, the smart belt 100 may transmit most-recently acquired information about a waist size to the host terminal 200, or may transmit, to the host terminal 200, information about a waist size that has been acquired for a predetermined period of time.

According to an exemplary embodiment, the smart belt 100 may determine whether a user who wears the smart belt 100 has an abdominal obesity, based on the information about the corrected waist size. When it is determined that the user who wears the smart belt 100 has abdominal obesity, the smart belt 100 may transmit information about the abdominal obesity to the host terminal 200.

The abdominal obesity is a body state in which excessive fat is accumulated in the abdomen, and a case where a Korean men' waist size is 90 cm (or 35.4 inches) or greater and a Korean women' waist size is 85 cm (or 33.5 inches) or greater may indicate the abdominal obesity.

In operation S1340, the host terminal 200 may output the information about the corrected waist size.

According to an exemplary embodiment, the host terminal 200 may output the information about the corrected waist size in the form of a voice, a text, a still image, or a moving picture, but the inventive concept is not limited thereto.

According to an exemplary embodiment, the host terminal 200 may output the information about the corrected waist size every time the information about the corrected waist size is received from the smart belt 100. Alternatively, when the host terminal 200 receives from the user an input of requesting a health care application to be executed, the host terminal 200 may output the information about the corrected waist size via an execution window of the health care application.

According to an exemplary embodiment, the host terminal 200 may display information about a current waist size and further display a waist size variation during a predetermined period of time, a target waist size, and the like. The host terminal 200 may also output the information about the abdominal obesity.

An operation, performed by the host terminal 200, of outputting the information about the abdominal obesity will now be described in more detail with reference to FIG. 14.

Figure 14:
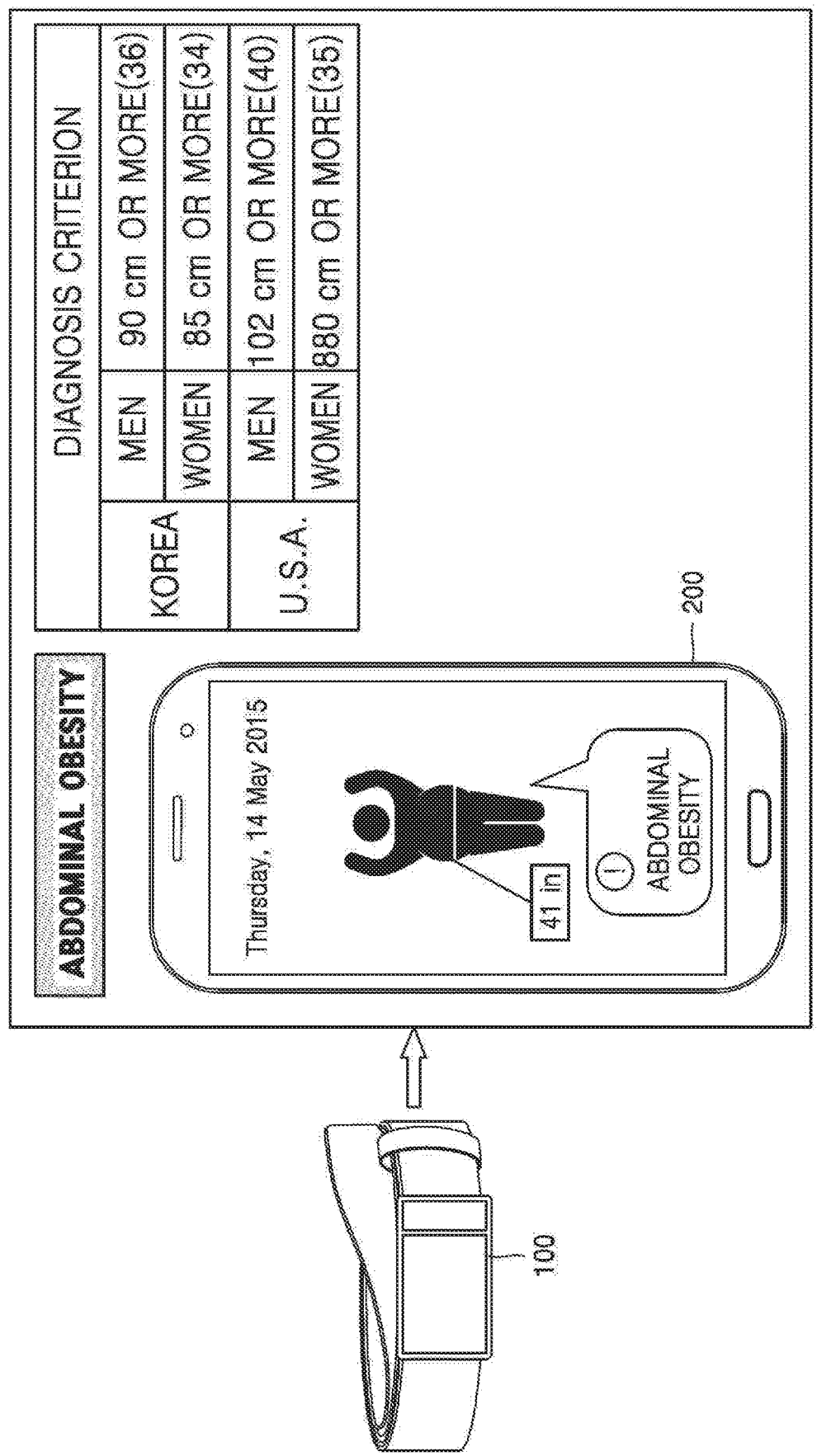
FIG. 14 is a view for explaining an operation, performed by a host terminal, of outputting information about abdominal obesity, according to an exemplary embodiment.

FIG. 14 is a view for explaining an operation, performed by a host terminal, of outputting information about abdominal obesity, according to an exemplary embodiment.

Referring to FIG. 14, the host terminal 200 may receive from the smart belt 100 information about the waist size of a user who wears the smart belt 100. For example, the host terminal 200 may receive information indicating that the waist size of the user who wears the smart belt 100 is '41 inches'.

At this time, the host terminal 200 may determine that the user has abdominal obesity, based on the information about the waist size (for example, 41 inches) received from the smart belt 100. The host terminal 200 may output to the screen thereof a warning message indicating the information about the waist size of the user (for example, 41 inches) and abdominal obesity. In this case, the user may check his or her current waist size and/or whether the user has abdominal obesity, via the host terminal 200.

Although FIG. 14 illustrates a case where the host terminal 200 determines whether a user has abdominal obesity, the inventive concept is not limited thereto. For example, the smart belt 100 may determine whether a user has abdominal obesity, and transmit information about abdominal obesity to the host terminal 200.

Figure 15:
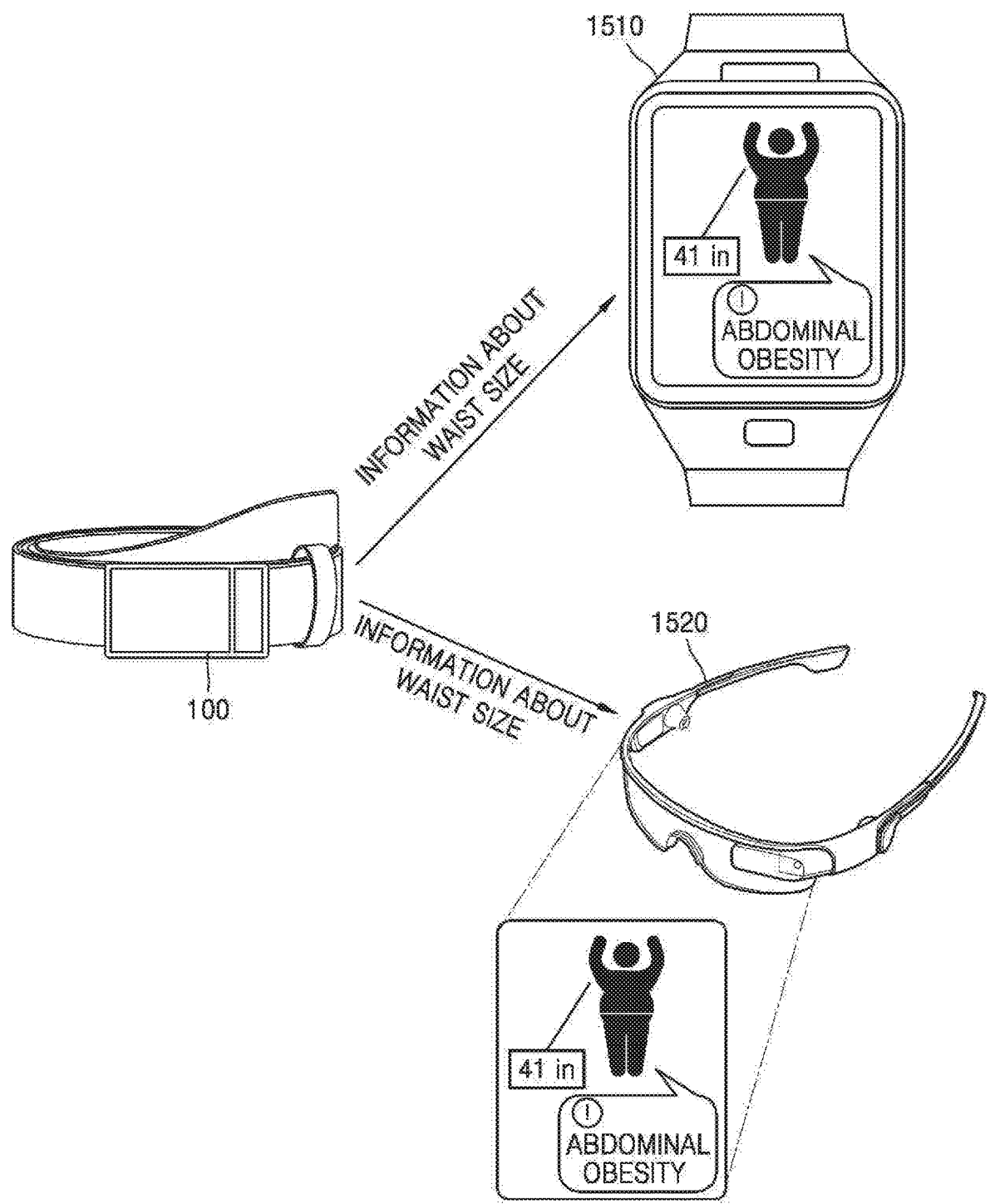
FIG. 15 is a view for explaining an operation, performed by a smart belt, of transmitting information about a waist size to an external wearable device, according to an exemplary embodiment.

FIG. 15 is a view for explaining an operation, performed by a smart belt, of transmitting information about a waist size to an external wearable device, according to an exemplary embodiment.

Referring to FIG. 15, the smart belt 100 may transmit information about a waist size to an external wearable device connected to the smart belt 100. For example, the smart belt 100 may transmit the information about the waist size to a smart watch 1510. At this time, the smart watch 1510 may output to the screen thereof a warning message indicating the information about the waist size of the user (for example, 41 inches) and/or abdominal obesity.

The smart belt 100 may also transmit the information about the waist size to wearable glasses 1520 worn by the user. At this time, the wearable glasses 1520 may output a warning message indicating the information about the waist size of the user (for example, 41 inches) and/or abdominal obesity, within a viewing angle of the user.

According to an exemplary embodiment, the smart belt 100 may transmit the information about the waist size directly to the external wearable devices 1510 and 1520, or may transmit the information about the waist size to the external wearable devices 1510 and 1520 via the host terminal 200 or a server.

Figure 16:
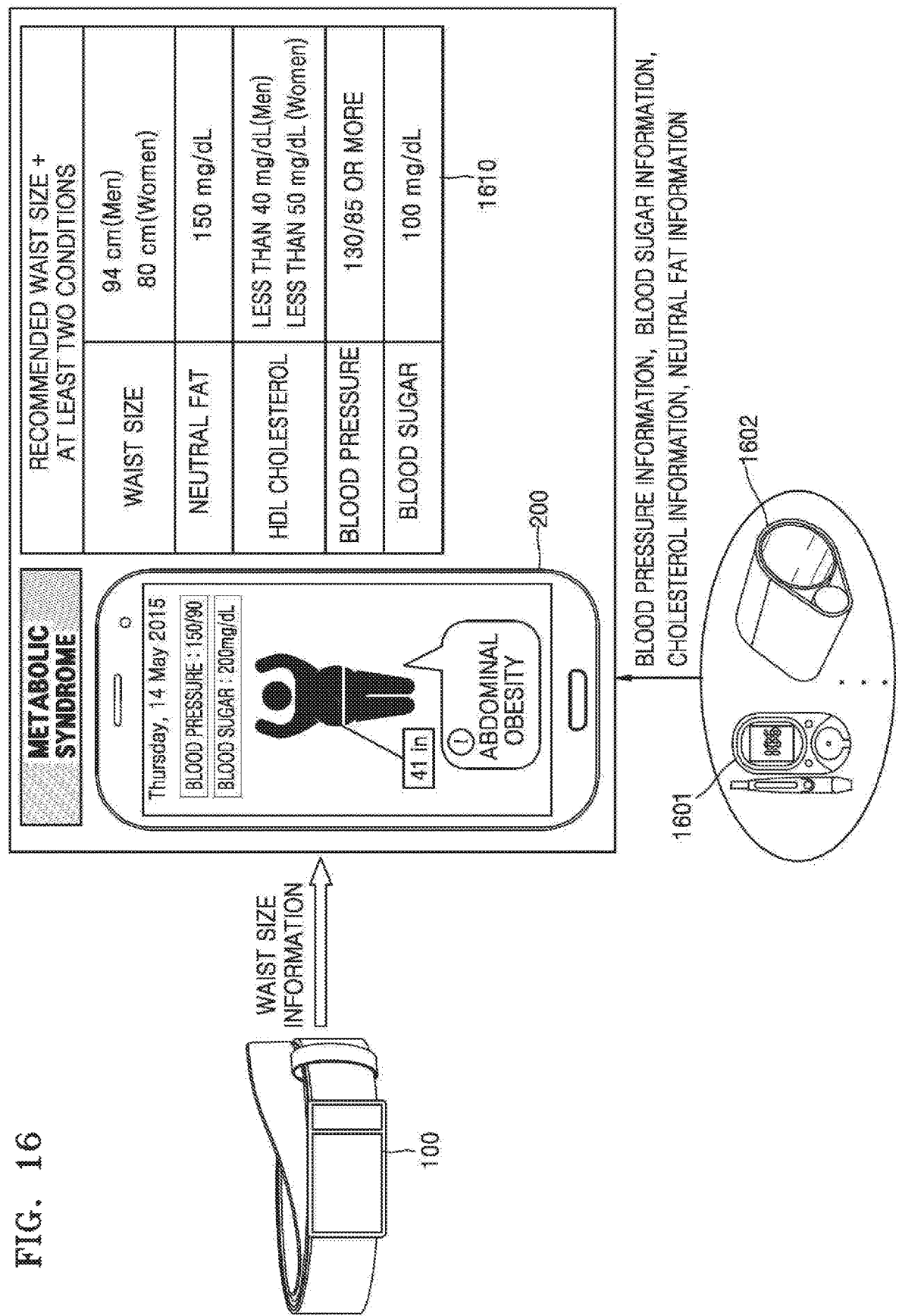
FIG. 16 is a view for explaining an operation, performed by a host terminal, of outputting information about a metabolic syndrome, according to an exemplary embodiment.

FIG. 16 is a view for explaining an operation, performed by a host terminal, of outputting information about a metabolic syndrome, according to an exemplary embodiment.

The host terminal 200 may receive information about a waist size (for example, 41 inches) from the smart belt 100. The host terminal 200 may also receive at least one of blood pressure information, blood sugar information, cholesterol information, and neutral fat information from at least one external apparatus, for example, external apparatuses 1601 and 1602. At this time, the host terminal 200 may receive at least one of the blood pressure information, the blood sugar information, the cholesterol information, and the neutral fat information via a server connected to the external apparatuses 1601 and 1602. According to an exemplary embodiment, the host terminal 200 may receive the blood sugar information, the cholesterol information, the blood pressure information, and the neutral fat information of the user from the user.

The host terminal 200 may diagnose a metabolic syndrome, based on the information about the waist size and at least one of the blood sugar information, the cholesterol information, the blood pressure information, and the neutral fat information of the user. In an exemplary embodiment of FIG. 16, when the waist size of a user who wears the smart belt 100 is 41 inches, the blood pressure thereof is 150/90, and the blood sugar thereof is 200 mg/dL, the host terminal 200 may determine that the user has a metabolic syndrome.

The host terminal 200 may output to the screen thereof a warning message indicating the information about the waist size of the user (for example, 41 inches) and/or a metabolic syndrome. In this case, the user may check his or her current waist size and/or whether the user has a metabolic syndrome, via the host terminal 200. Also, the host terminal 200 may output information 1610 indicating recommended waist size and recommended conditions for at least two of the blood sugar information, the cholesterol information, the blood pressure information, and the neutral fat information of the user.

Although FIG. 16 illustrates a case where the host terminal 200 determines whether a user has a metabolic syndrome, the inventive concept is not limited thereto. For example, the smart belt 100 may diagnose a metabolic syndrome, and transmit information about a metabolic syndrome to the host terminal 200.

Figure 17:
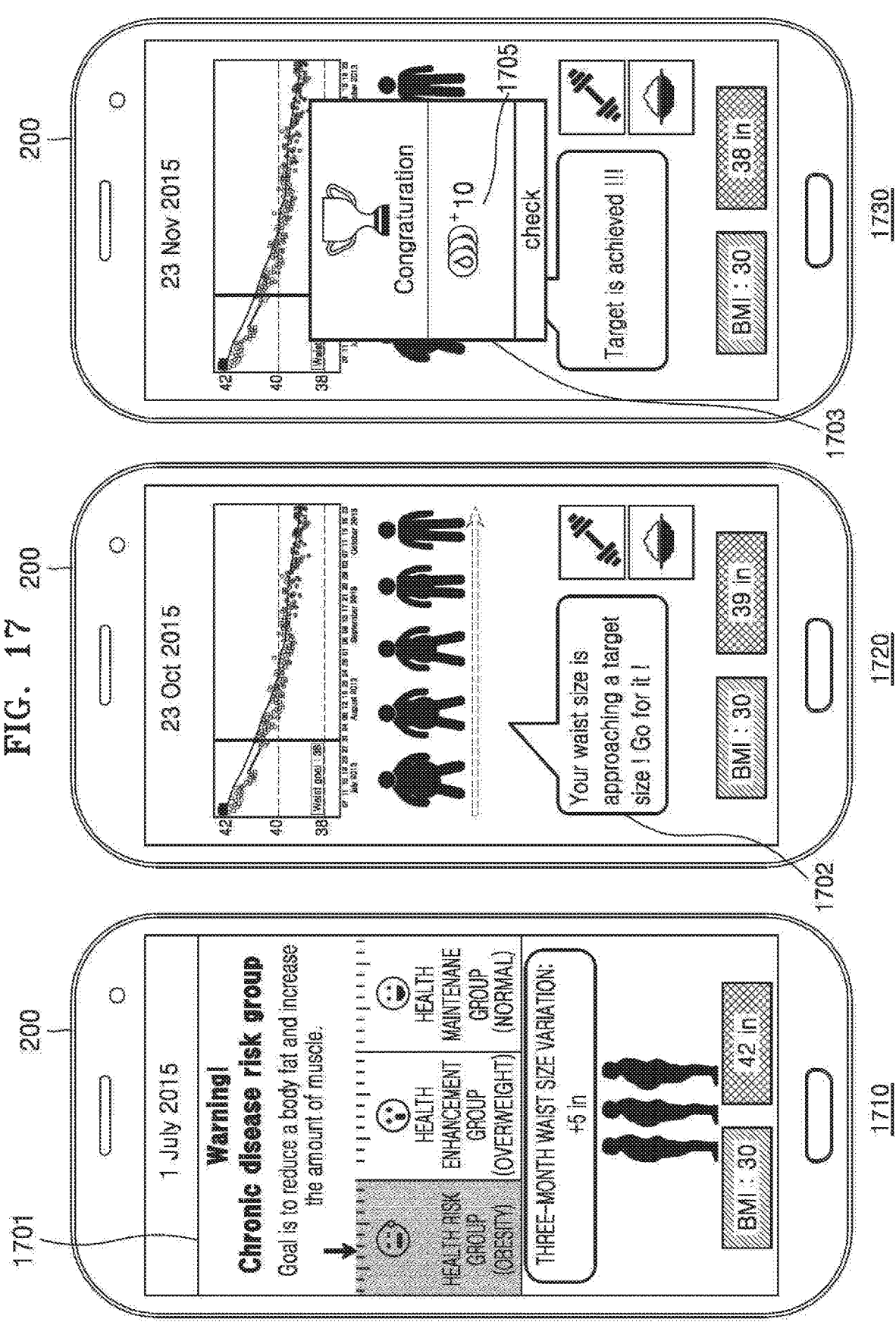
FIG. 17 is a view for explaining an operation, performed by a host terminal, of outputting a warning message, according to an exemplary embodiment.

FIG. 17 is a view for explaining an operation, performed by a host terminal, of outputting a notification message, according to an exemplary embodiment.

Referring to an example screen 1710 of FIG. 17, the host terminal 200 may output a warning message 1701 informing about a health risk, based on information about a waist size received from the smart belt 100. For example, when the waist size of the user has increased by 5 inches over three months and reaches 42 inches, the host terminal 200 may output a warning message (for example, 'Warning! Chronic disease risk group') together with information about a waist size variation (for example, 'three-month waist size variation: +5 in'). According to an exemplary embodiment, the host terminal 200 may display the information about the waist size variation as an image.

Referring to an example screen 1720 of FIG. 17, the host terminal 200 may output a message 1702 encouraging a health care, based on the information about the waist size received from the smart belt 100. For example, when a target waist size of a user is 38 inches and a waist size measured by the smart belt 100 is 39 inches, the host terminal 200 may output a message that the user's waist size is approaching the target size (for example, 'Your waist size is approaching a target size ! Go for it!') via a text or a voice.

According to an exemplary embodiment, the host terminal 200 may display a change in the waist size as a graph or as an icon image.

Referring to an example screen 1730 of FIG. 17, the host terminal 200 may output a message 1703 indicating that the target waist size has been achieved, based on information about the waist size received from the smart belt 100. For example, when the target waist size of the user is 38 inches, the host terminal 200 may output a congratulation message (for example, 'Congratulation, Target is achieved!!!') at the moment when the waist size measured by the smart belt 100 reaches 38 inches.

According to an exemplary embodiment, when the waist size of the user has reached the target waist size, the host terminal 200 may provide a reward 1705 to the user. The reward may be provided to the user in various forms, e.g., a point that can be cashed at a certain store or an application.

According to an exemplary embodiment, the host terminal 200 may provide information related to a health care to the user. An exemplary operation, performed by the host terminal 200, of providing information related to a health care will be described with reference to FIGS. 18-20.

Figure 18:
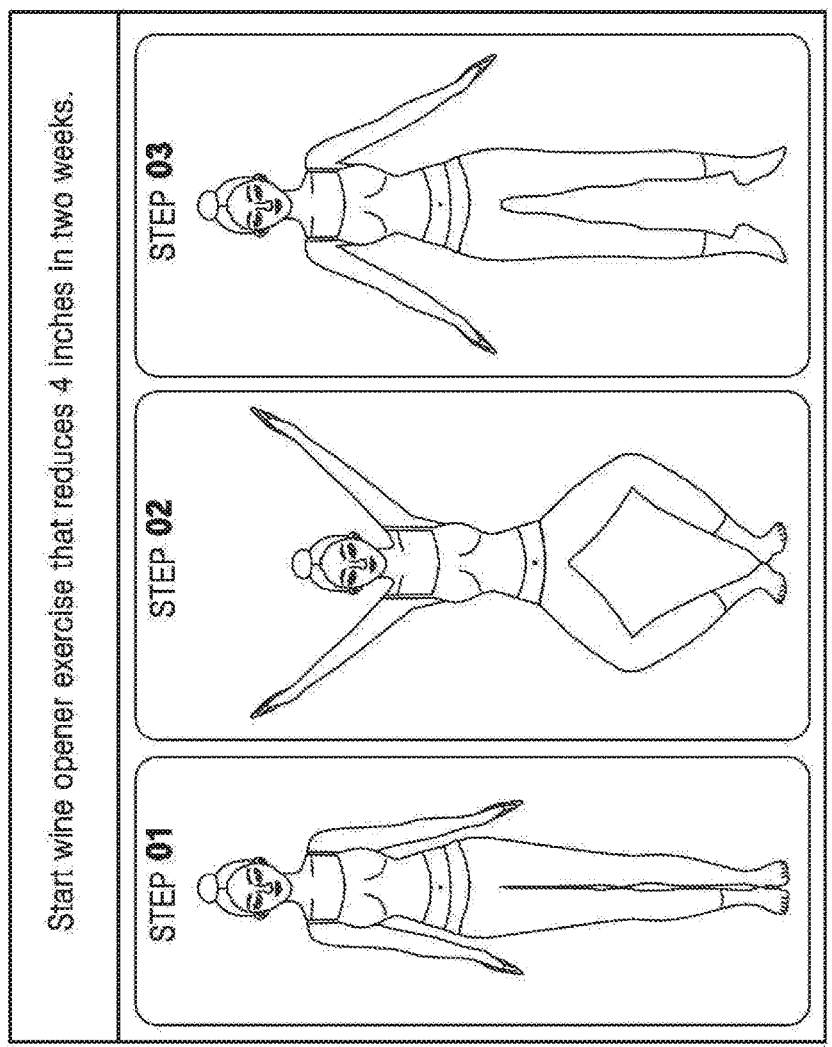
FIG. 18 is a view for explaining an operation, performed by a host terminal, of recommending an exercise, according to an exemplary embodiment.

FIG. 18 is a view for explaining an operation, performed by a host terminal, of recommending an exercise, according to an exemplary embodiment.

Referring to an example screen 1810 of FIG. 18, the host terminal 200 may receive from a user an input of requesting an exercise recommendation. For example, the host terminal 200 may receive an input of selecting an exercise recommendation item 1800 displayed on a touch screen. For example, the input of selecting the exercise recommendation item 1800 may be a touch input such as, for example, a single tap, a double tap, a drag, etc.

Referring to a diagram 1820 of FIG. 18, the host terminal 200 may provide information about an exercise method capable of reducing a waist size, in response to the input of selecting the exercise recommendation item 1800. For example, the host terminal 200 may output a text, a voice, an image, or a moving picture that describes a wine opener exercise.

FIG. 19 is a view for explaining an operation, performed by a host terminal, of recommending food, according to an exemplary embodiment.

Referring to 1910 of FIG. 19, the host terminal 200 may receive from a user an input of requesting a food recommendation. For example, the host terminal 200 may receive a touch input of selecting a food recommendation item 1900 displayed on a touch screen.

Referring to an example screen 1910 of FIG. 19, the host terminal 200 may recommend a food that may contribute in reducing a waist size, in response to the input of selecting the food recommendation item 1900. For example, the host terminal 200 may output information 1920 in a form of, for example, a text, an image, a voice, or a moving picture that recommends a mate tea that is effective to reduce a waist size.

Figure 20:
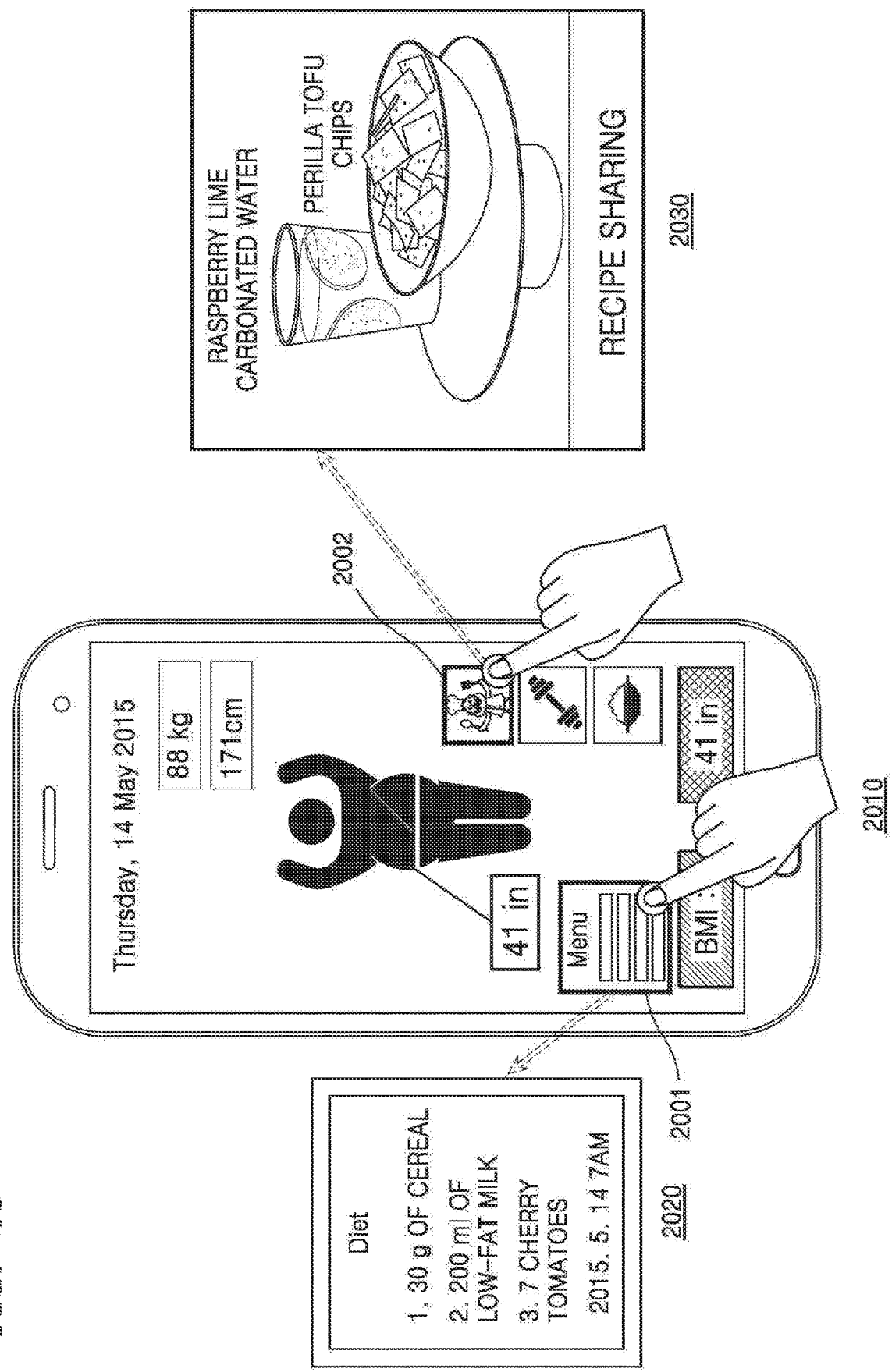
FIG. 20 is a view for explaining an operation, performed by a host terminal, of providing diet information or recipe information, according to an exemplary embodiment.

FIG. 20 is a view for explaining an operation, performed by a host terminal, of providing diet information or recipe information, according to an exemplary embodiment.

Referring to 2010 of FIG. 20, the host terminal 200 may receive from a user an input of requesting a diet recommendation. For example, the host terminal 200 may receive an input of selecting a diet recommendation item 2001 displayed on a touch screen.

Referring to 2020 of FIG. 20, the host terminal 200 may provide diet information, in response to the input of selecting the diet recommendation item 2001. The host terminal 200 may provide a diet corresponding to a time when the user selects the diet recommendation item 2001. For example, when the user selects the diet recommendation item 2001 at 7 A.M., the host terminal 200 may provide information about a breakfast menu, for example, 30 g of cereal, 200 ml of low-fat milk, and 7 cherry tomatoes.

Referring to 2030 of FIG. 20, the host terminal 200 may provide recipe information of a food that may contribute in reducing a waist size, in response to an input of selecting a recipe item 2002. For example, the host terminal 200 may provide information, for example, 'raspberry lime carbonated water and *perilla* tofu chips' in a text, still image, moving picture, or uniform resource locator (URL) form.

Exemplary embodiments in which the smart belt 100 corrects a waist size have been described above. An exemplary embodiment in which the host terminal 200 corrects a waist size based on tension information will now be described with reference to FIG. 21.

Figure 21:
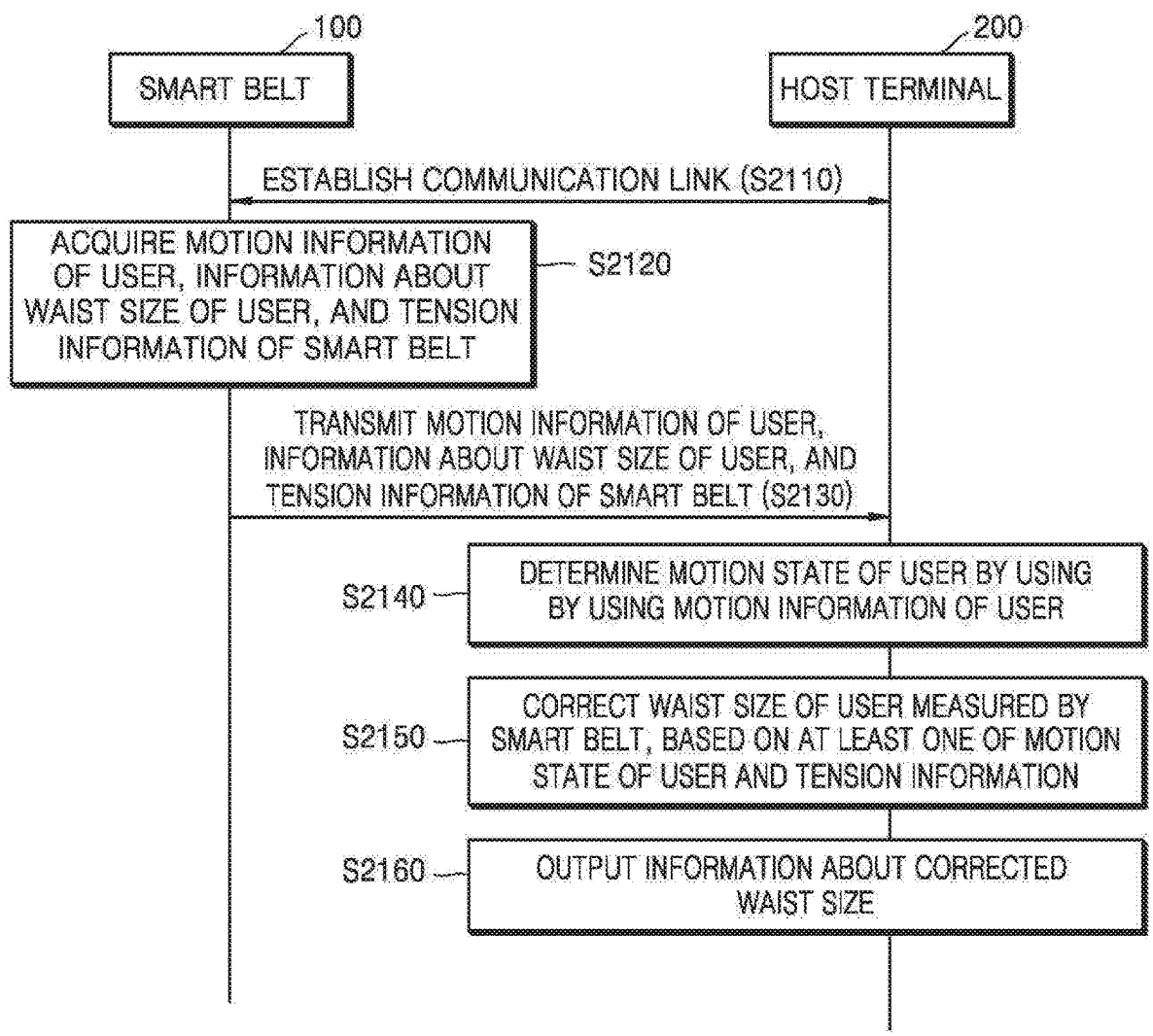
FIG. 21 is a flowchart of a method in which a host terminal corrects a waist size of a user, according to an exemplary embodiment.

FIG. 21 is a flowchart of a method in which a host terminal corrects a waist size of a user, according to an exemplary embodiment.

In operation S2110, the smart belt 100 and the host terminal 200 may establish a communication link therebetween.

For example, the smart belt 100 may establish a local area communication link and/or may establish a mobile communication link (for example, 3G, 4G, or 5G) with the host terminal 200. Examples of the local area communication may include, but is not limited to, Bluetooth, Bluetooth Low Energy (BLE), Wi-Fi Direct, ultra wideband (UWB), Zigbee, Near Field Communication (NFC), and Ant+.

In operation S2120, the smart belt 100 may acquire motion information of a user, information about a waist size of the user, and tension information of the smart belt 100.

According to an exemplary embodiment, the smart belt 100 may sense a motion of the user by using the inertia sensor 111. For example, the smart belt 100 may acquire a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor.

According to an exemplary embodiment, the smart belt 100 may measure the waist size of a user who wears the smart belt 100, by using the waist size sensor 112. For example, the smart belt 100 may measure the waist size by using an optical sensor, according to at least one of an incremental linear encoder method, an absolute linear encoder method, an incremental rotary encoder method, and an absolute rotary encoder method. The smart belt 100 may measure the waist size of the user by using the image sensor or the magnetic field sensor. A method in which the waist size sensor 112 of the smart belt 100 measures the waist size of the user has been described above with reference to FIGS. 3A and 3B, and thus a detailed description thereof will be omitted.

According to an exemplary embodiment, the smart belt 100 may acquire the tension information of the smart belt 100 by using the tension sensor 113. For example, the smart belt 100 may measure a tension of the smart belt 100 by using the FSR sensor 102 or the strain gauge 106, but the inventive concept is not limited thereto. A method in which the smart belt 100 measures a tension has been described above with reference to FIG. 2, and thus a repeated description thereof will be omitted.

According to an exemplary embodiment, the smart belt 100 may periodically acquire the tension information of the smart belt 100 by using the tension sensor 113. For example, the smart belt 100 may acquire the tension information at intervals of 10 minutes.

The smart belt 100 may acquire the tension information at a predefined time. For example, the smart belt 100 may acquire the tension information of the smart belt 100 between 7:00 A.M. and 8:00 A.M during which the user goes to work, between 12:00 P.M. and 1:00 P.M. during which the user has lunch, or between 7:00 P.M. and 8:00 P.M. during which the user has dinner. The predefined time may be changed according to a user input or user profile information of the user.

According to an exemplary embodiment, the smart belt 100 may acquire the tension information when a specific event occurs. For example, when an event in which the waist size sensor 112 measures the waist size of the user occurs, the smart belt 100 may activate the tension sensor 113 to measure a tension value of the smart belt 100.

In operation S2130, the smart belt 100 may transmit the motion information of the user, the information about the waist size of the user, and the tension information of the smart belt 100 to the host terminal 200.

According to an exemplary embodiment, the smart belt 100 may periodically transmit the motion information of the user, the information about the waist size of the user, and the tension information of the smart belt 100 to the host terminal 200. For example, the smart belt 100 may transmit the motion information of the user, the information about the waist size of the user, and the tension information of the smart belt 100 to the host terminal 200 once an hour.

According to an exemplary embodiment, when the smart belt 100 receives a request from the host terminal 200, the smart belt 100 may transmit at least one of the motion information of the user, the information about the waist size of the user, and the tension information of the smart belt 100 to the host terminal 200. For example, when the host terminal 200 receives from the user an input of executing a health care application, the host terminal 200 may request the smart belt 100 for at least one of the motion information of the user, the information about the waist size of the user, and the tension information of the smart belt 100. In this case, the smart belt 100 may transmit at least one of the motion information of the user, the information about the waist size of the user, and the tension information of the smart belt 100 to the host terminal 200.

According to an exemplary embodiment, the smart belt 100 may transmit the motion information of the user, the information about the waist size of the user, and the tension information of the smart belt 100 to the host terminal 200 when a preset event occurs. For example, when an event where the waist size of the user increases 1 cm occurs, the smart belt 100 may transmit at least one of the motion information of the user, the information about the waist size of the user, and the tension information of the smart belt 100 to the host terminal 200. Alternatively, when an event where the user arrives at home occurs, the smart belt 100 may transmit the motion information of the user, the information about the waist size of the user, and the tension information of the smart belt 100 to the host terminal 200.

According to an exemplary embodiment, the smart belt 100 may transmit at least one of the motion information of the user, the information about the waist size of the user, and the tension information of the smart belt 100 to the host terminal 200. For example, the smart belt 100 may transmit two or more of the above information altogether or separately.

In operation S2140, the host terminal 200 may determine a motion state of the user by using the motion information of the user. For example, the host terminal 200 may determine a motion state of the user during a waist size measurement, by using the motion information of the user.

According to an exemplary embodiment, the smart belt 200 may determine whether the user is in a stopped state, a walking state, or a running state, by using at least one of an acceleration value, an inclination value, a position value, and a pressure value included in the motion information of the user. For example, by using acceleration information measured by an acceleration sensor, the host terminal 200 may determine that a user is in a stopped state when the user has moved at an average speed of 0.001 km/h for a certain period of time, may determine that the user is walking when the user moves at an average speed of 4 km/h for a certain period of time, and may determine that the user is running when the user moves at an average speed of 15 km/h for a certain period of time. When the host terminal 200 determines that the user is standing, the host terminal 200 may also determine whether the user is standing at an angle or upright, by using a gyroscope sensor.

According to an exemplary embodiment, the host terminal 200 may also determine whether the user is sitting, standing, or lying, by using the tension information acquired by the tension sensor 113.

In operation S2150, the host terminal 200 may correct a waist size of the user measured by the smart belt 100, based on at least one of the motion state of the user and the tension information.

According to an exemplary embodiment, the host terminal 200 may correct the measured waist size of the user, based on the motion state of the user. For example, when the motion state of the user at a time of measuring the waist size is not a predefined reference state, the host terminal 200 may correct the measured waist size. The predefined reference state may be, but is not limited to, a standing-upright state or a standing-upright quiver state.

The host terminal 200 may convert a first waist size value measured in a first motion state into a second waist size value corresponding to the predefined reference state. For example, when a waist size is measured in a sitting state, the host terminal 200 may convert the waist size measured in the sitting state into a waist size corresponding to the reference state, by using the human body modeling information. The human body modeling information may include information representing a result of analyzing waist size values respectively corresponding to motion states of the user. If the waist size value measured in a sitting state is 82 cm, the host terminal 200 may convert the measured waist size value of 82 cm into a waist size value 77 cm corresponding to the reference state by using the human body modeling information.

According to an exemplary embodiment, the host terminal 200 may correct the waist size measured by the smart belt 100, based on the tension information. According to an exemplary embodiment, the host terminal 200 may correct the waist size measured by the smart belt 100, by using a tension-based standard table. In the tension-based standard table, a tension is matched with a waist size correction value. According to an exemplary embodiment, the waist size correction value included in the tension-based standard table may be calculated by taking into account body information (for example, a gender, an age, a height, and a weight) of a user.

For example, according to the tension-based standard table, when a tension is 100 g, a waist size correction value is '0', and, as the tension increases from 100 g, the waist size correction value may increase. For example, when the tension is 400 g, the waist size correction value may be '+2 cm', and, when the tension is 700 g, the waist size correction value may be '+4 cm'.

An increase in a tension denotes an increase in a waist tightening force of the smart belt 100, and thus a measured waist size becomes smaller than the actual waist size.

For example, when the length of the smart belt 100 is not adjusted although the belly of the user further protrudes due to overeating than before eating, the waist size of the user measured by the smart belt 100 may remain the same. However, in reality, the waist size after eating may be greater than the waist size before eating. Accordingly, the host terminal 200 may accurately predict a current waist size of the user by adding a waist size correction value corresponding to the increased tension value to the measured waist size value, by using the tension-based standard table.

According to an exemplary embodiment, the host terminal 200 may correct the waist size measured by the smart belt 100 by taking into account the motion state of the user and the tension information of the smart belt 100.

For example, the host terminal 200 may primarily correct the first waist size value measured by the smart belt 100 into the second waist size value corresponding to the reference state, and then may secondarily correct the second waist size value into a third waist size value by taking into account the tension information of the smart belt 100.

In operation S2160, the host terminal 200 may output the information about the corrected waist size.

According to an exemplary embodiment, the host terminal 200 may output the information about the corrected waist size in the form of a voice, a text, a still image, or a moving picture, but the inventive concept is not limited thereto.

According to an exemplary embodiment, the host terminal 200 may display information about a current corrected waist size and further display a waist size variation during a predetermined period of time, a target waist size, and the like. The host terminal 200 may output the information about abdominal obesity and/or a metabolic syndrome.

The host terminal 200 may provide information about an overeating behavior of the user, based on the waist size information received from the smart belt 100. An operation, performed by the host terminal 200, of managing the overeating behavior of the user will now be described in more detail with reference to FIG. 22.

Figure 22:
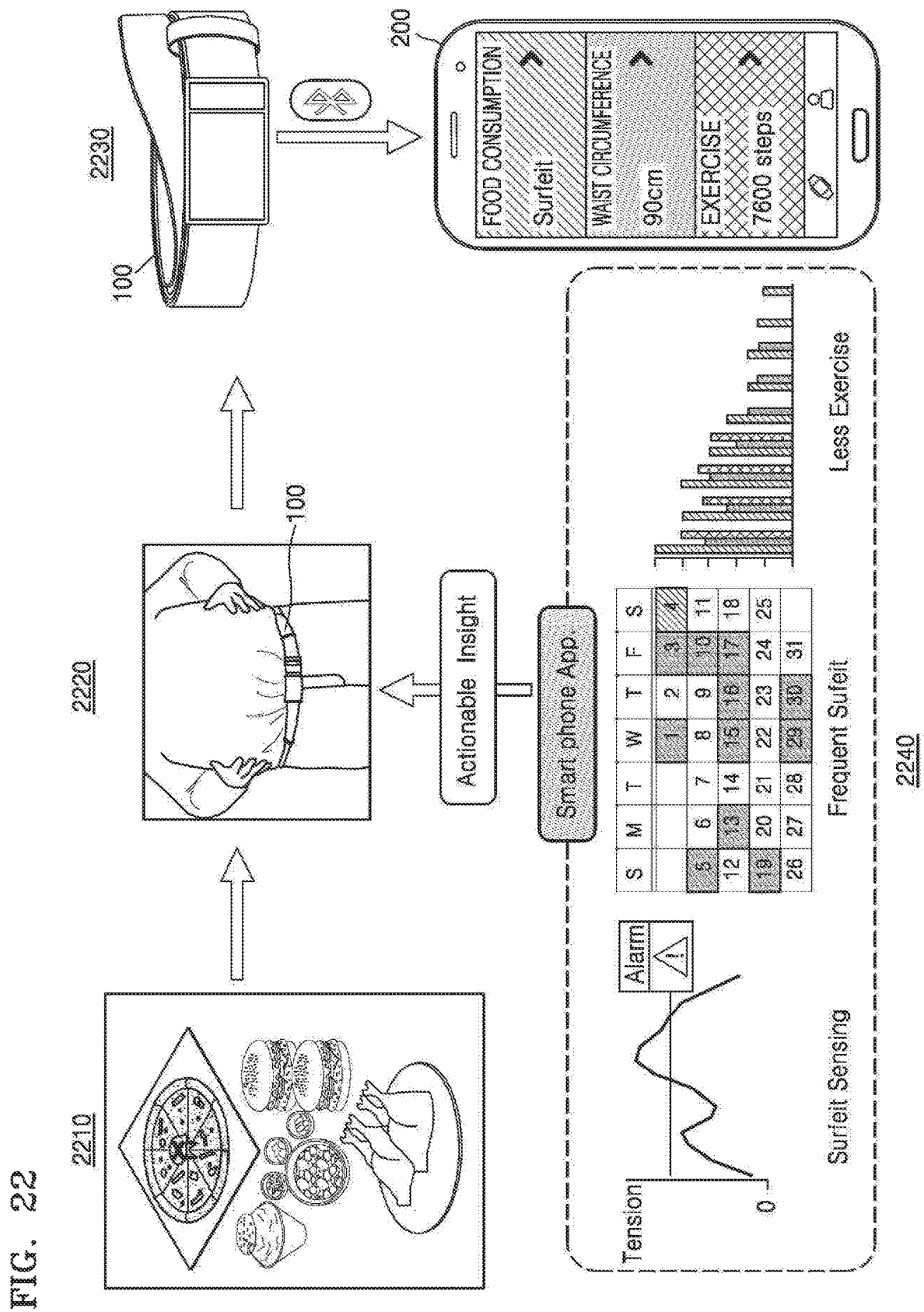
FIG. 22 is a view for explaining a system for detecting overeating of a user, according to an exemplary embodiment.

FIG. 22 is a view for explaining a system for detecting overeating of a user, according to an exemplary embodiment.

Referring to FIG. 22, when the user overeats food as shown in 2210, a waist size of the user measured by the smart belt 100 may increase as shown in 2220. For example, when the user overeats, the user may increase the length of a portion of the smart belt 100 that surrounds the waist of the user, and thus the waist size of the user measured by the waist size sensor 112 may increase. Even when the user does not adjust the length of the portion of the smart belt 100 that surrounds the waist of the user, when the belly of the user protrudes due to overeating and thus a tension of the smart belt 100 increases, the smart belt 100 may sense an increase in an actual waist size of the user by correcting the waist size measured by the waist size sensor 112 according to the tension applied to the smart belt 100.

The smart belt 100 may periodically transmit information related to a measured waist size to the host terminal 200 as shown in 2230. For example, the smart belt 100 may transmit information about a waist size to the host terminal 200, by using a local area communication (e.g., Bluetooth).

When the waist size of the user sharply increases within a predetermined period of time, the host terminal 200 may determine that the user has overeaten, as shown in 2240. For example, when the waist size of the user was 38 inches at 1:00 P.M. on May 18 and became 40 inches at 8:00 P.M. on May 18, the host terminal 200 may determine that the user has overeaten in the evening.

The host terminal 200 may check an overeating cycle of the user. For example, the host terminal 200 may check the number of times the user overeats per month. The host terminal 200 may mark the day on which the user has overeaten, on the calendar. The host terminal 200 may check and display the workout quantity (e.g., workout duration or workout intensity) of the user.

The user may execute a health care application of the host terminal 200 and check overeating or non-overeating, an overeating cycle, an overeating frequency, and a workout quantity, and the like.

Figure 23:
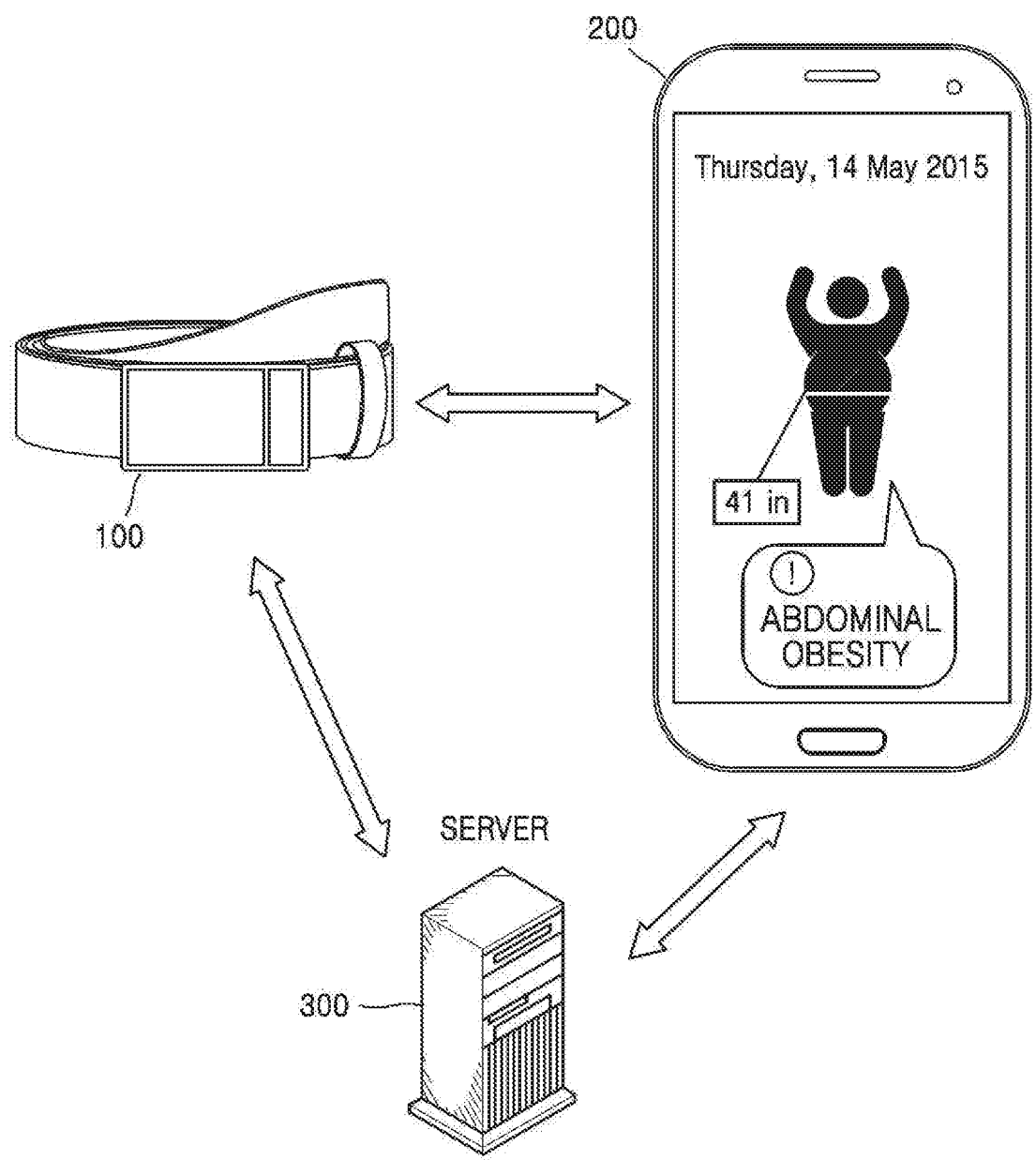
FIG. 23 is a view for explaining a waist size management system according to an exemplary embodiment.

FIG. 23 is a view for explaining a waist size management system according to an exemplary embodiment.

Referring to FIG. 23, the waist size management system may include a smart belt 100, a host terminal 200, and a server 300. However, all of the illustrated components may not be essential. Since the smart belt 100 and the host terminal 200 have been described above with reference to FIG. 1, the server 300 will now be described.

The server 300 is included to transmit or receive data to or from the smart belt 100 and the host terminal 200. For example, the server 300 may be a cloud server, a personal server, a medical institution server, or a health information storage server. Examples of the health information storage server may include, but are not limited to, an electronic medical record (EMR) server, an electronic health record (HER) server, and a personal health record (PHR) server.

According to an exemplary embodiment, the server 300 may include an intelligence engine, and the server 300 may analyze waist size information, motion information of a user, and tension information obtained by the smart belt 100 via the intelligence engine. For example, the server 300 may correct a waist size based on the tension information of the smart belt 100, or may determine an abdominal obesity risk and/or a metabolic syndrome of the user based on corrected waist size information.

A method in which the server 300 analyzes waist size information collected from the smart belt 100 will now be described with reference to FIG. 24.

Figure 24:
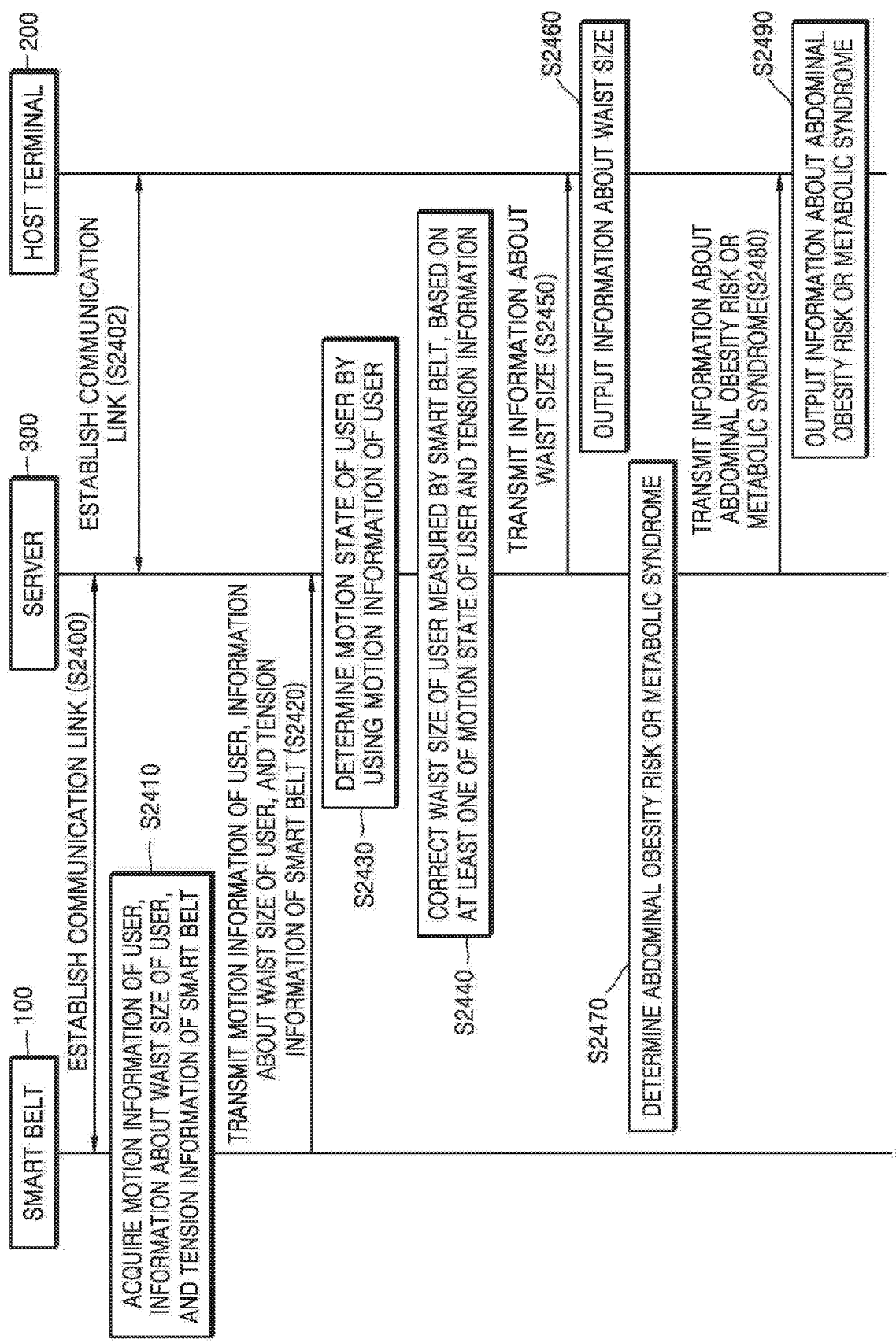
FIG. 24 is a flowchart of a waist size correcting method performed by a server, according to an exemplary embodiment.

FIG. 24 is a flowchart of a waist size correcting method performed by a server, according to an exemplary embodiment.

In operation S2400, the smart belt 100 and the server 300 may establish a communication link therebetween. In operation S2402, the host terminal 200 may also establish a communication link with the server 300.

In operation S2410, the smart belt 100 may acquire at least one of motion information of a user, information about a waist size of the user, and tension information of the smart belt 100.

According to an exemplary embodiment, the smart belt 100 may sense a motion of the user by using the inertia sensor 111. For example, the smart belt 100 may acquire at least one of a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor.

According to an exemplary embodiment, the smart belt 100 may measure the waist size of a user who wears the smart belt 100, by using the waist size sensor 112. For example, the smart belt 100 may measure the waist size by using an optical sensor, according to at least one of an incremental linear encoder method, an absolute linear encoder method, an incremental rotary encoder method, and an absolute rotary encoder method. The smart belt 100 may measure the waist size of the user by using the image sensor or the magnetic field sensor.

According to an exemplary embodiment, the smart belt 100 may acquire the tension information of the smart belt 100 by using the tension sensor 113. For example, the smart belt 100 may measure a tension of the smart belt 100 by using the FSR sensor 102 or the strain gauge 106, but the inventive concept is not limited thereto.

According to an exemplary embodiment, the smart belt 100 may periodically acquire the tension information of the smart belt 100 by using the tension sensor 113. Alternatively, the smart belt 100 may acquire the tension information of the smart belt 100 at a predefined time. According to an exemplary embodiment, the smart belt 100 may acquire the tension information when a specific event occurs. For example, when an event in which the waist size sensor 112 measures the waist size of the user occurs, the smart belt 100 may activate the tension sensor 113 to measure a tension value of the smart belt 100.

In operation S2420, the smart belt 100 may transmit the motion information of the user, the information about the waist size of the user, and the tension information of the smart belt 100 to the server 300.

According to an exemplary embodiment, the smart belt 100 may periodically transmit the motion information of the user, the information about the waist size of the user, and the tension information of the smart belt 100 to the server 300. For example, the smart belt 100 may transmit the motion information of the user, the information about the waist size of the user, and the tension information of the smart belt 100 to the server 300 once an hour.

According to an exemplary embodiment, when the smart belt 100 receives a request from the server 300, the smart belt 100 may transmit the motion information of the user, the information about the waist size of the user, and the tension information of the smart belt 100 to the server 300.

According to an exemplary embodiment, the smart belt 100 may transmit at least one of the motion information of the user, the information about the waist size of the user, and the tension information of the smart belt 100 to the server 300 when a preset event occurs. For example, when an event where the waist size of the user increases by 1 cm occurs, the smart belt 100 may transmit at least one of the motion information of the user, the information about the waist size of the user, and the tension information of the smart belt 100 to the server 300. Alternatively, when an event where the user arrives at home occurs, the smart belt 100 may transmit at least one of the motion information of the user, the information about the waist size of the user, and the tension information of the smart belt 100 to the server 300.

According to an exemplary embodiment, the smart belt 100 may transmit the motion information of the user, the information about the waist size of the user, and the tension information of the smart belt 100 to the server 300. For example, the smart belt 100 may transmit two or more of the above information altogether or separately.

In operation S2430, the server 300 may determine a motion state of the user by using the motion information of the user. For example, the server 300 may determine a motion state of the user during a waist size measurement, by using the motion information of the user.

According to an exemplary embodiment, the server 300 may determine whether the user is in a stopped state, a walking state, or a running state, by using at least one of an acceleration value, an inclination value, a position value, and a pressure value included in the motion information of the user. For example, by using acceleration information measured by the acceleration sensor, the server 300 may determine that the user is in a stopped state when the user has moved at an average speed of 0.001 km/h for a certain period of time, may determine that the user is walking when the user moves at an average speed of 4 km/h for a certain period of time, and may determine that the user is running when the user moves at an average speed of 15 km/h for a certain period of time. When the server 300 determines that the user is standing, the smart belt 100 may also determine whether the user is standing at an angle or upright, by using the gyroscope sensor.

According to an exemplary embodiment, the server 300 may also determine whether the user is sitting, standing, or lying, by using the tension information acquired by the tension sensor 113.

In operation S2440, the server 300 may correct a waist size of the user measured by the smart belt 100, based on at least one of the motion state of the user and the tension information.

According to an exemplary embodiment, the server 300 may correct the measured waist size of the user, based on the motion state of the user. For example, when the motion state of the user when the waist size is measured is not a predefined reference state, the server 300 may correct the measured waist size. The predefined reference state may be, but is not limited to, a standing-upright state or a standing-upright quiver state.

The server 300 may convert a first waist size value measured in a first motion state into a second waist size value corresponding to the predefined reference state. For example, when a waist size in a sitting state is measured, the server 300 may convert the waist size measured in the sitting state into a waist size in the reference state, by using the human body modeling information. The human body modeling information may include information representing a result of analyzing waist size values respectively corresponding to motion states of the user. If the waist size value measured in a sitting state is 82 cm, the server 300 may convert the measured waist size value of 82 cm into a waist size value 77 cm corresponding to the reference state by using the human body modeling information.

According to an exemplary embodiment, the server 300 may correct the waist size measured by the smart belt 100, based on the tension information. According to an exemplary embodiment, the server 300 may correct the waist size measured by the smart belt 100, by using a tension-based standard table. In the tension-based standard table, a tension is matched with a waist size correction value. According to an exemplary embodiment, the waist size correction value included in the tension-based standard table may be calculated by taking into account body information (for example, a gender, an age, a height, and a weight) of a user.

For example, according to the tension-based standard table, when a tension is 100 g, a waist size correction value is '0', and, as the tension increases from 100 g, the waist size correction value may increase. For example, when the tension is 400 g, the waist size correction value may be '+2 cm', and, when the tension is 700 g, the waist size correction value may be '+4 cm'.

An increase in a tension denotes an increase in a waist tightening force of the smart belt 100, and thus a measured waist size becomes smaller than the actual waist size.

For example, when the length of the smart belt 100 is not adjusted although the belly of the user further protrudes due to overeating than before eating, the waist size of the user measured by the smart belt 100 may remain the same. However, in reality, the waist size after eating may be greater than the waist size before eating. Accordingly, the server 300 may accurately predict a current waist size of the user by adding a waist size correction value corresponding to the increased tension value to the measured waist size value, by using the tension-based standard table.

According to an exemplary embodiment, the server 300 may correct the waist size measured by the smart belt 100 by taking into account both the motion state of the user and the tension information of the smart belt 100.

For example, the server 300 may primarily correct the first waist size value measured by the smart belt 100 into the second waist size value corresponding to the reference state, and then may secondarily correct the second waist size value into a third waist size value by taking into account the tension information of the smart belt 100.

In operation S2450, the server 300 may transmit information about a waist size to the host terminal 200.

For example, the server 300 may transmit information about a corrected waist size to the host terminal 200 via the communication link.

According to an exemplary embodiment, the server 300 may periodically transmit the information about the corrected waist size to the host terminal 200, or may transmit the information about the corrected waist size in response to a request from the host terminal 200.

For example, when the host terminal 200 receives from the user an input of executing a health care application, the host terminal 200 may request the server 300 to transmit the information about the waist size of the user. In this case, the server 300 may transmit the information about the corrected waist size to the host terminal 200.

In operation S2460, the host terminal 200 may output the information about the waist size.

According to an exemplary embodiment, the host terminal 200 may output the information about the corrected waist size in the form of a voice, a text, a still image, or a moving picture, but the inventive concept is not limited thereto.

According to an exemplary embodiment, the host terminal 200 may display information about a current corrected waist size and further display a waist size variation during a predetermined period of time, a target waist size, and the like.

In operation S2470, the server 300 may determine an abdominal obesity risk or a metabolic syndrome.

According to an exemplary embodiment, the server 300 may determine whether a user who wears the smart belt 100 has abdominal obesity, based on the information about the corrected waist size. The abdominal obesity is a body state in which excessive fat is accumulated in the abdomen, and a case where a Korean men' waist size is 90 cm (35.4 inches) or greater and a Korean women' waist size is 85 cm (33.5 inches) or greater may correspond to the abdominal obesity.

The server 300 may also receive blood pressure information, blood sugar information, cholesterol information, and neutral fat information from at least one external apparatus (for example, a blood pressure machine and a blood sugar machine). According to an exemplary embodiment, the server 300 may receive, from the host terminal 200, blood sugar information, cholesterol information, blood pressure information, and neutral fat information of the user input by the user.

The server 300 may diagnose a metabolic syndrome, based on the information about the corrected waist size and at least two of the blood sugar information, the cholesterol information, the blood pressure information, and the neutral fat information of the user. For example, when the waist size of a user is 41 inches, the neutral fat thereof is 160 mg/dL, and the blood sugar thereof is 200 mg/dL, the server 300 may determine that a user who wears the smart belt 100 has a metabolic syndrome.

In operation S2480, the server 300 may transmit information about an abdominal obesity risk or a metabolic syndrome to the host terminal 200. For example, the server 300 may transmit the information about the abdominal obesity risk or the metabolic syndrome to the host terminal 200 via the communication link.

In operation S2490, the host terminal 200 may output the information about the abdominal obesity risk or the metabolic syndrome. According to an exemplary embodiment, the host terminal 200 may output the information about the abdominal obesity risk or the metabolic syndrome in the form of a voice, a text, a still image, or a moving picture, but the inventive concept is not limited thereto.

According to an exemplary embodiment, the smart belt 100 may analyze an activity of the user by using at least one sensor. A method in which the smart belt 100 provides activity information of a user will now be described in detail with reference to FIG. 25.

Figure 25:
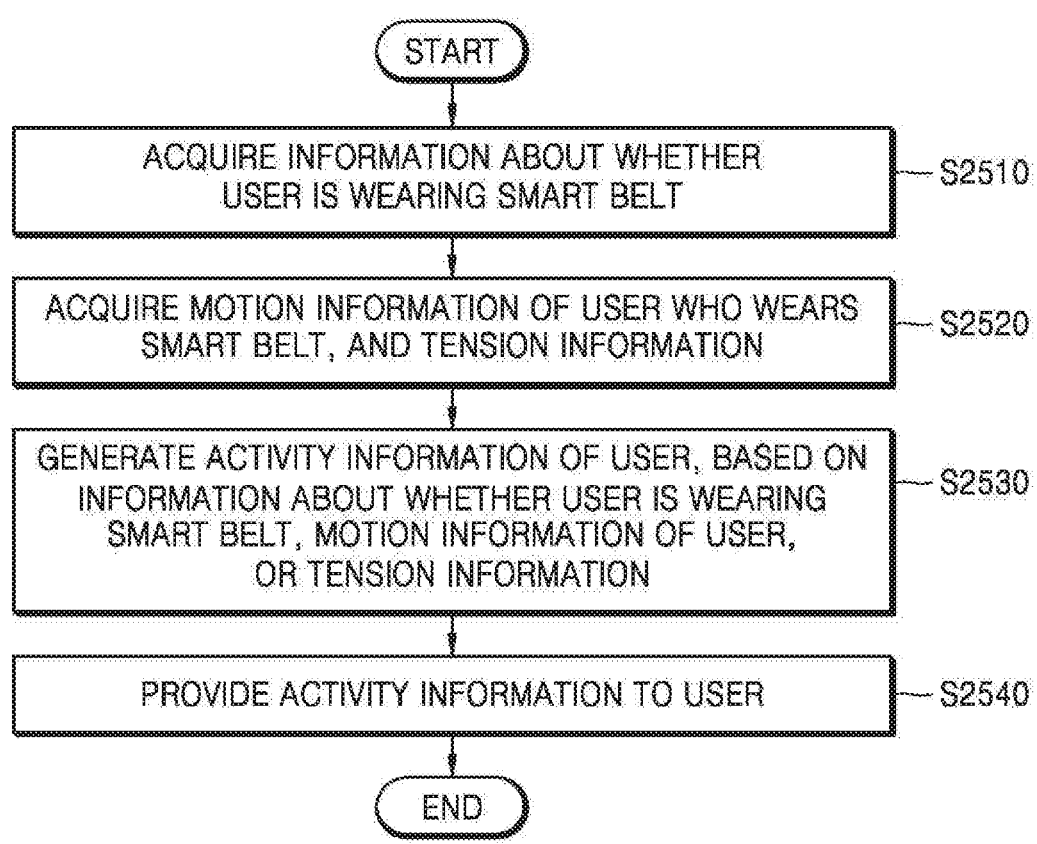
FIG. 25 is a flowchart of a method of providing activity information of a user, according to an exemplary embodiment.

FIG. 25 is a flowchart of a method of providing activity information of a user, according to an exemplary embodiment.

In operation S2510, the smart belt 100 may acquire information about whether the user is wearing the smart belt 100. The information about whether the user is wearing the smart belt 100 may include, but is not limited to, wearing start time information (for example, 8 A.M.) representing a time when the user starts wearing the smart belt 100, wearing end time information (for example, 10 P.M.) representing a time when the user takes off the smart belt 100, wearing/taking-off frequency information (for example, 5 times) representing how often the user puts on and takes off the smart belt 100 in one day, and information about whether the user is currently wearing the smart belt 100.

According to an exemplary embodiment, the smart belt 100 may determine whether the user is wearing the smart belt 100, based on a signal received from at least one of the inertia sensor 111, the waist size sensor 112, the tension sensor 113, and the magnetic sensor.

In operation S2520, the smart belt 100 may acquire motion information of the user who wears the smart belt 100, and tension information. For example, when it is determined that the user is wearing the smart belt 100, the smart belt 100 may acquire the motion information of the user or tension information of the smart belt 100.

According to an exemplary embodiment, the smart belt 100 may sense a motion of the user by using the inertia sensor 111. For example, the smart belt 100 may acquire at least one of a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor.

According to an exemplary embodiment, the smart belt 100 may acquire the tension information of the smart belt 100 by using the tension sensor 113. For example, the smart belt 100 may measure a tension of the smart belt 100 by using the FSR sensor 102 or the strain gauge 106, but the inventive concept is not limited thereto. A method in which the smart belt 100 acquires the motion information of the user and the tension information of the smart belt 100 has been described above in detail, and thus a repeated description thereof will be omitted.

In operation S2530, the smart belt 100 may generate the activity information of the user, based on the information about whether the user is wearing the smart belt 100, the motion information of the user, or the tension information. The activity information of the user may denote information about activities that are conducted by the user between a wake-up time and a bed time. For example, the activity information of the user may include, but is not limited to, commuting time information, overtime work information, defecation information, laugh information, drinking information, smoking information, seizure information, or falling information of the user. For example, the activity information of the user may also include driving time information, information about a period of time spent by the user while sitting in a day, information about the time when the user goes to school and comes home from school, exercise time information, and overeating information.

According to an exemplary embodiment, the smart belt 100 may acquire pattern information representing a result of patterning a motion (for example, an acceleration value, an angular speed value, and a tension value of the smart belt 100) corresponding to an activity of the user, and store the pattern information in a memory. The smart belt 100 may generate the activity information of the user by comparing the pattern information stored in the memory with a currently-measured motion of the user.

An operation, performed by the smart belt 100, of collecting information about various activities of a user will be described in detail later with reference to FIGS. 26-44.

In operation S2540, the smart belt 100 may provide the activity information to the user. For example, the smart belt 100 may transmit the activity information to the host terminal 200 or the server 300. At this time, the host terminal 200 may display the activity information of the user. For example, the user may check, via the host terminal 200, the commuting time information, the overtime work information, the defecation information, the laugh information, the drinking information, the smoking information, the seizure information, or the falling information. When the smart belt 100 includes a display, the smart belt 100 may display the activity information of the user via the display.

An exemplary embodiment in which the smart belt 100 generates the activity information of the user and the host terminal 200 displays the activity information of the user will now be described in detail with reference to FIGS. 26-44.

Figure 26:
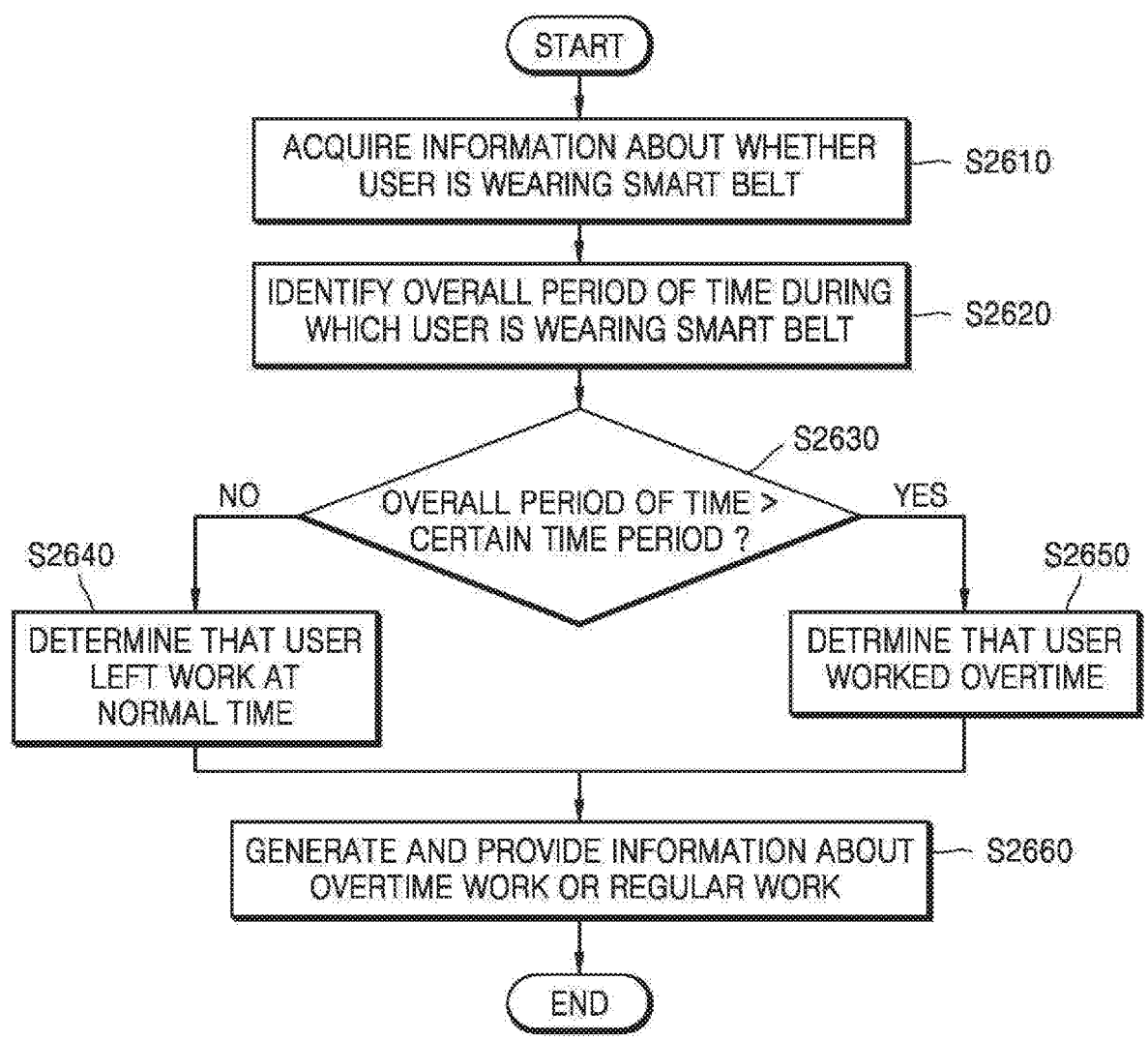
FIG. 26 is a flowchart of a method of providing information about regular work or overtime work, according to an exemplary embodiment.

FIG. 26 is a flowchart of a method of providing information about regular work or overtime work, according to an exemplary embodiment.

In operation S2610, the smart belt 100 may acquire information about whether a user is wearing the smart belt 100.

For example, the smart belt 100 may sense whether the user starts or ends wearing the smart belt 100, by using at least one of the magnetic sensor, the proximity sensor, the waist size sensor 112, the inertia sensor 111 (e.g., an acceleration sensor), and the tension sensor 113.

For example, when a value sensed by the magnetic sensor changes from '000' to '001', the smart belt 100 may determine that the user has started wearing the smart belt 100, and, when the value sensed by the magnetic sensor is '000' for a predetermined period of time or more (for example, 30 minutes or more), the smart belt 100 may determine that the user has ended wearing the smart belt 100 (see FIG. 7B).

When an acceleration value measured by the inertia sensor 111 is within a first certain range, a tension value measured by the tension sensor 113 is within a second certain range, or a respiration signal value measured by the respiration sensor is within a third certain range, the smart belt 100 may determine that the user is wearing the smart belt 100, but the inventive concept is not limited thereto. The smart belt 100 may determine whether the user is wearing the smart belt 100, by using various methods.

In operation S2620, the smart belt 100 may identify an overall period of time during which the user is wearing the smart belt 100, based on the information about whether the user is wearing the smart belt 100.

For example, the smart belt 100 may acquire overall time information (for example, 14 hours) representing an overall period of time during which the user is wearing the smart belt 100, by using information about a time point (for example, 8 A.M.) when the user has started wearing the smart belt 100 and information about a time point (for example, 10 P.M.) when the user has ended wearing the smart belt 100.

In operation S2630, the smart belt 100 may compare the overall time information (for example, 14 hours), representing the overall period of time during which the user is wearing the smart belt 100, with a certain time period. The certain time period may serve as a basis for distinguishing a regular work hour from an overtime work hour. In this case, the certain time period may be determined in consideration of a commute time. For example, when a regular working hour are from 9 A.M. to 6 P.M. and an average round trip commute time is one hour, the certain time period may be 10 hours. In this case, the certain time period may be a certain time range (for example, 10 hours to 10.5 hours) in consideration of a possible error.

The certain time period may be set by the user and may be adjusted by the user. For example, when an overall working hour of the user is adjusted from 9 hours to 5 hours, the user may adjust the certain time period from 10.5 hours to 6.5 hours.

In operation S2640, when the overall period of time during which the user is wearing the smart belt 100 is less than or equal to the certain time period, the smart belt 100 may determine that the user leaves work at a normal time. For example, when the user wears the smart belt 100 at 8:30 A.M., arrives to work by 9 A.M., leaves work at 6 P.M., and then arrives at home at 6:30 P.M., the smart belt 100 may sense that the overall period of time during which the user is wearing the smart belt 100 is 10 hours. In this case, since the overall period of time (e.g., 10 hours) during which the user is wearing the smart belt 100 is less than the certain time period (e.g. 10.5 hours), the smart belt 100 may determine that the user leaves work at a normal time.

In operation S2650, when the overall period of time during which the user is wearing the smart belt 100 is greater than the certain time period, the smart belt 100 may determine that the user works overtime. For example, when the user wears the smart belt 100 at 8:30 A.M., arrives to work by 9 A.M., leaves work at 9 P.M., and then arrives at home at 9:30 P.M., the smart belt 100 may sense that the overall period of time during which the user is wearing the smart belt 100 is 13 hours. In this case, since the overall period of time (e.g., 13 hours) during which the user is wearing the smart belt 100 is greater than the certain time period (e.g. 10.5 hours), the smart belt 100 may determine that the user works overtime.

In operation S2660, the smart belt 100 may generate information about overtime work hour or regular work hour of the user (hereinafter, referred to as overtime work information) and provide the overtime work information to the user. For example, the smart belt 100 may generate overtime work information of the user that includes an overtime work date, an overtime work hour, an overtime work frequency for a week, an average overtime work frequency for a month, and the like. According to an exemplary embodiment, the smart belt 100 may provide the overtime work information to the host terminal 200 (e.g., a mobile terminal of the user). At this time, the user may check the overtime work information via the host terminal 200. For example, the user may execute a specific application installed on the mobile terminal and check the overtime work information generated by the smart belt 100 via an execution screen image of the specific application. An exemplary screen image that provides overtime work information will now be described with reference to FIGS. 27 and 28.

Figure 27:
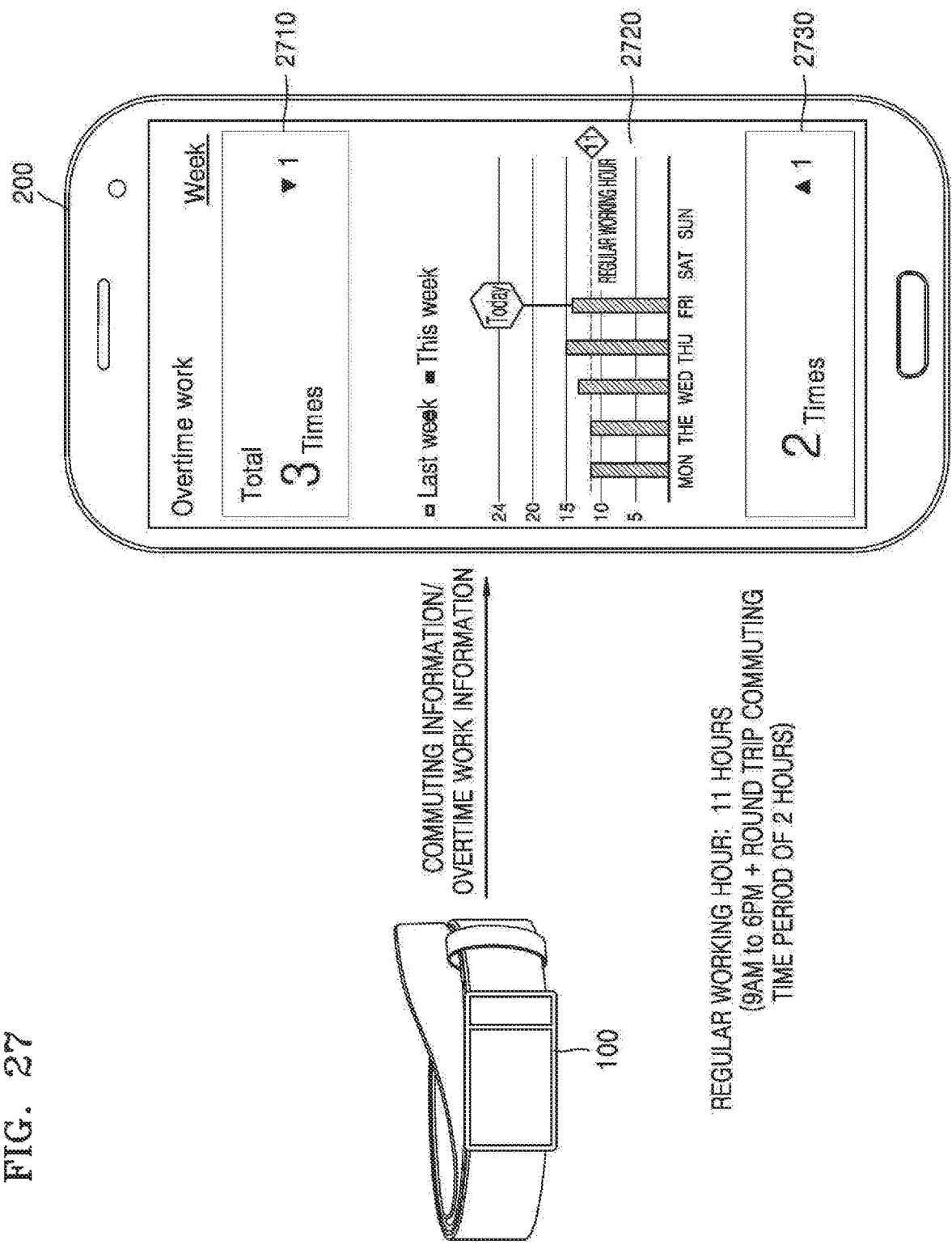
FIG. 27 illustrates a screen image that provides overtime work information in units of weeks, according to an exemplary embodiment.

FIG. 27 illustrates a screen image that provides overtime work information in units of weeks, according to an exemplary embodiment.

Referring to FIG. 27, the smart belt 100 may generate overtime work information of a user by comparing overall time information, representing an overall period of time during which the user is wearing the smart belt 100, with a regular working hour. FIG. 27 illustrates a case where the regular working hours are a total of 11 hours including a round trip commuting time period (for example, 2 hours).

The host terminal 200 may display the overtime work information received from the smart belt 100 on the screen in response to a user input. For example, the host terminal 200 may display information 2710 representing an overtime work frequency this week, a graph 2720 showing an overall working hour (or an overall time period during which the user is wearing the smart belt 100) for each day of the week, and information 2730 representing an overtime work frequency last week, but the inventive concept is not limited thereto.

Figure 28:
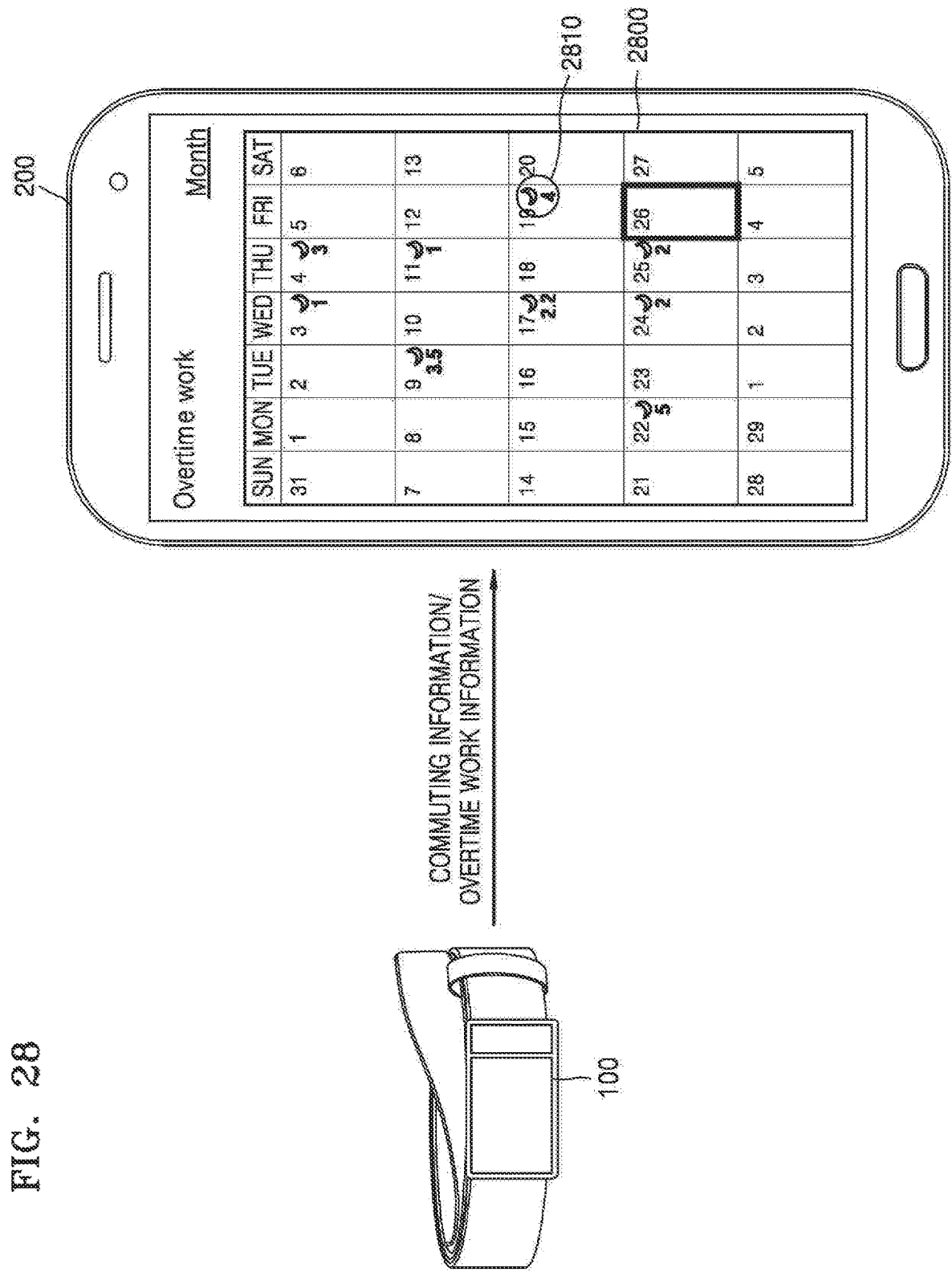
FIG. 28 illustrates a screen image that provides overtime work information in units of months, according to an exemplary embodiment.

FIG. 28 illustrates a screen image that provides overtime work information in units of months, according to an exemplary embodiment.

Referring to FIG. 28, the host terminal 200 may display an indicator 2810 indicating the day on which a user worked overtime, on a calendar 2800. For example, the host terminal 200 may display a crescent-shaped icon as the indicator 2810 on the day when the user worked overtime, but the inventive concept is not limited thereto.

According to an exemplary embodiment, the host terminal 200 may display overtime working hours (for example, 4 hours) together with the indicator 2810, on the calendar 2800. In this case, the user may understand an overtime working trend of the user for the current month at a glance via the calendar 2800.

Although the smart belt 100 determines overtime working or regular working based on the overall time period during which the user is wearing the smart belt 100 in FIGS. 26-28, the inventive concept is not limited thereto. According to an exemplary embodiment, the smart belt 100 may determine overtime working or regular working of the user, based on a period of time obtained by subtracting a commuting time period from the overall time period during which the user is wearing the smart belt 100. For example, by using location information of the user (for example, information representing a time period during which the user stays in the workplace), the smart belt 100 may determine that the user normally left work at a normal time, when the user had stayed in the workplace for 9 hours while wearing the smart belt 100, and may determine that the user worked overtime, when the user had stayed in the workplace for 11 hours while wearing the smart belt 100.

Figure 29:
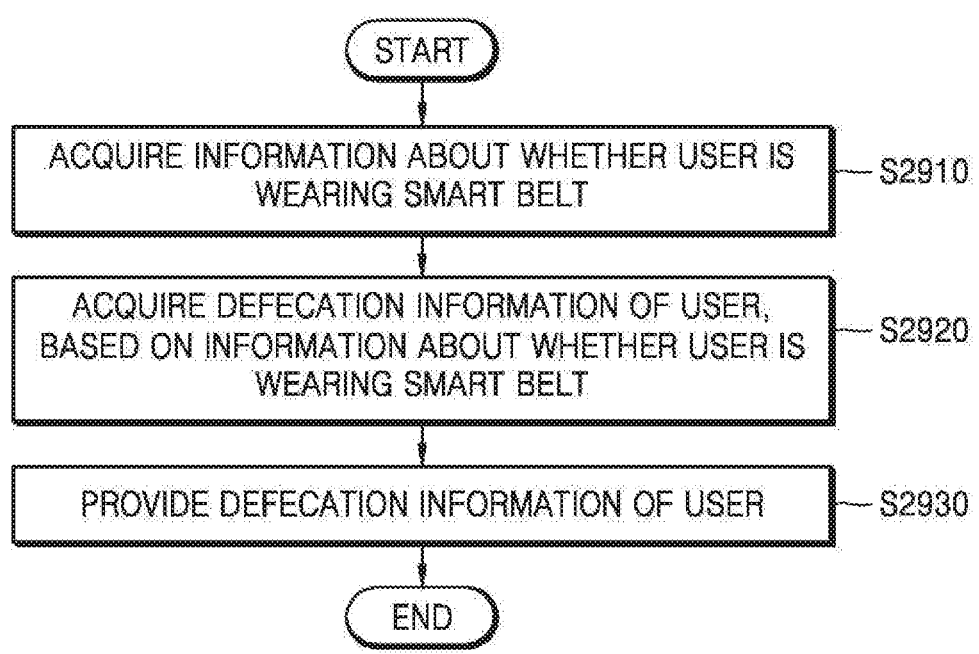
FIG. 29 is a flowchart of a method of providing bowel movement information of a user, according to an exemplary embodiment.

FIG. 29 is a flowchart of a method of providing defecation information of a user, according to an exemplary embodiment.

In operation S2910, the smart belt 100 may acquire information about whether the user is wearing the smart belt 100.

The information about whether the user is wearing the smart belt 100 may include wearing start time information (for example, 8 A.M.) representing a time when the user starts wearing the smart belt 100, wearing end time information (for example, 10 P.M.) representing a time when the user takes off the smart belt 100, wearing/taking-off frequency information (for example, 5 times) representing how often the user puts on and takes off (or ties and unties) the smart belt 100 in one day. The information about whether the user is wearing the smart belt 100 may further include information about a time period (for example, 7 minutes) between a time when the user takes off (or unties) the smart belt 100 and a time when the user wears (or ties) the smart belt 100 again. Operation S2910 may correspond to operation S2610 of FIG. 26, a repeated description of which will be omitted.

In operation S2920, the smart belt 100 may acquire defecation information of the user, based on the information about whether the user is wearing the smart belt 100 (or whether the smart belt 100 is tied or untied). The defecation information of the user may include, but is not limited to, a defecation frequency for a day (for example, 1 time/1 day), a defecation time period (for example, 5 minutes), an average defecation time period (for example, 10 minutes), and information about a defecation state (for example, normal, diarrhea, constipation).

According to an exemplary embodiment, the smart belt 100 may determine whether the time period taken to take off the smart belt 100 and then wear the smart belt 100 again (or the time period taken to untie the smart belt 100 and then tie the smart belt 100 again) is within a certain time period. For example, when the time period for the user to take off (or untie) the smart belt 100 and then wear (or tie) the smart belt 100 again is within 30 minutes, the smart belt 100 may determine that the user has defecated. On the other hand, when the time period for the user to take off (or untie) the smart belt 100 and then wear (or tie) the smart belt 100 again exceeds 30 minutes, the smart belt 100 may determine that the user has not defecated. For example, when the user takes off (or unties) the smart belt 100 and then re-wears (or re-ties) the smart belt 100 one hour after doing exercise, this may not affect a defecating frequency counted by the smart belt 100.

According to an exemplary embodiment, when the user defecates four or more times a day, the smart belt 100 may determine that the user had diarrhea, and, when the user defecates less than three times a week, the smart belt 100 may determine that the user was constipated.

In operation S2930, the smart belt 100 may provide the defecation information of the user. For example, when the smart belt 100 includes a display, the smart belt 100 may display the defecation information of the user on the display.

The smart belt 100 may provide the defecation information via the host terminal 200 (e.g., a mobile terminal of the user). At this time, the user may check the defecation information via the host terminal 200. For example, the user may execute a specific application installed on the host terminal 200 and check the defecation information generated by the smart belt 100 via an execution screen image of the specific application. The defecation information provided by the host terminal 200 will now be described in more detail with reference to FIGS. 30 and 31.

Figure 30:
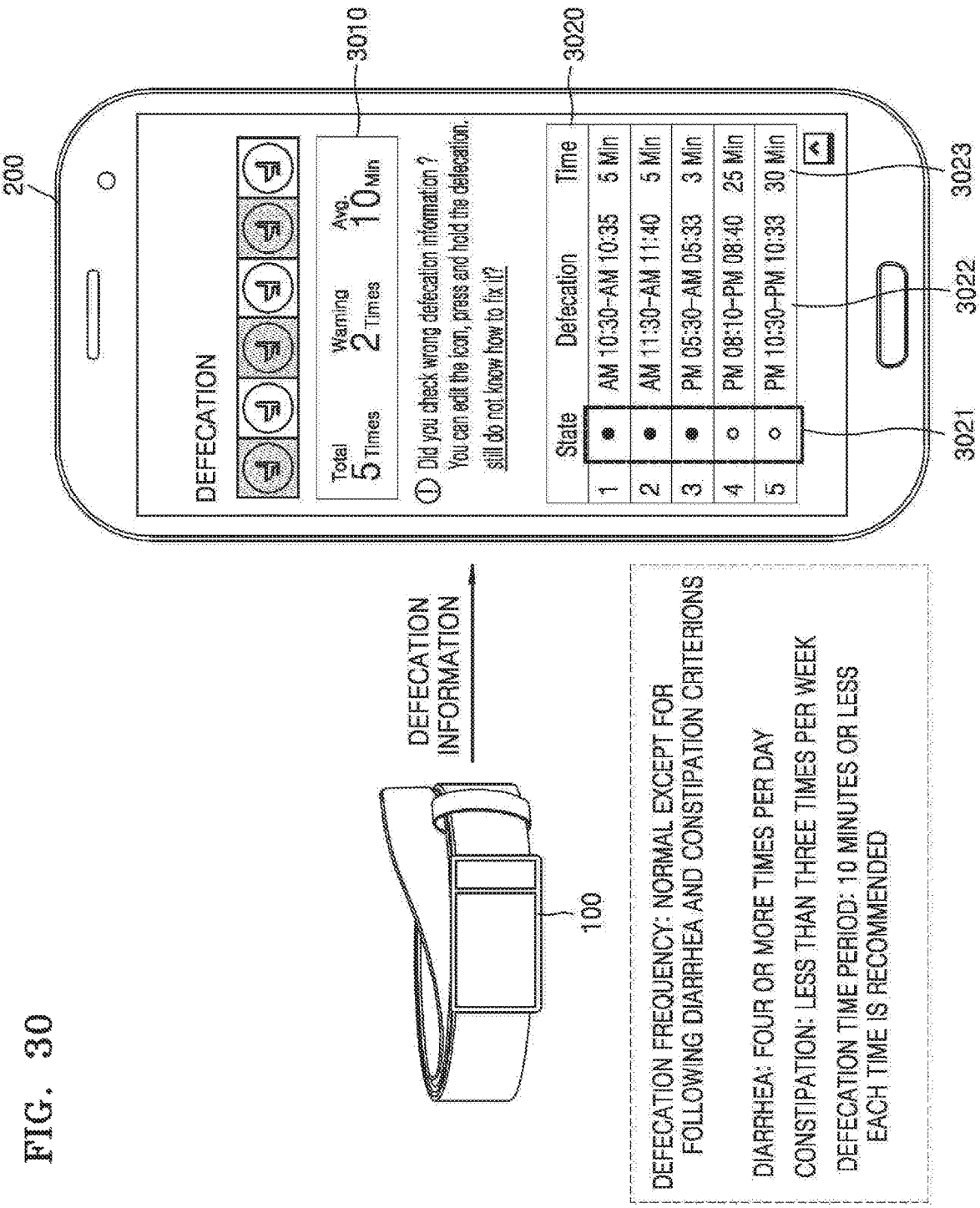
FIG. 30 illustrates a screen image that provides bowel movement information in units of days, according to an exemplary embodiment.

FIG. 30 illustrates a screen image that provides defecation information in units of days, according to an exemplary embodiment.

Referring to FIG. 30, the smart belt 100 may transmit to the host terminal 200 defecation information of a user generated based on information about whether the user is wearing the smart belt 100. FIG. 30 illustrates a case where a recommended defecation time is within 10 minutes for one time.

According to an exemplary embodiment, the host terminal 200 may display the defecation information received from the smart belt 100 on the screen in response to a user input. For example, the host terminal 200 may briefly display today's defecation information 3010 (for example, a defecation frequency for today of 5, an average defecation time period of 10 mins, and a frequency of 2 at which a defecation time period exceeds a recommended defecation time period).

The host terminal 200 may also provide detailed information 3020 about defecation of the user. For example, the host terminal 200 may display, as the detailed information 3020, an indicator 3021 indicating whether each defecation time exceeds the recommended defecation duration, information 3022 about a time point when each defecation occurred, and a defecation duration 3023.

The user may check the defecation information via the host terminal 200 and delete wrongly collected defecation information. For example, when defecation did not occur between 5:30 P.M. and 5:33 P.M., the user may delete defecation information corresponding to 5:30 P.M. to 5:33 P.M. from the screen image.

Figure 31:
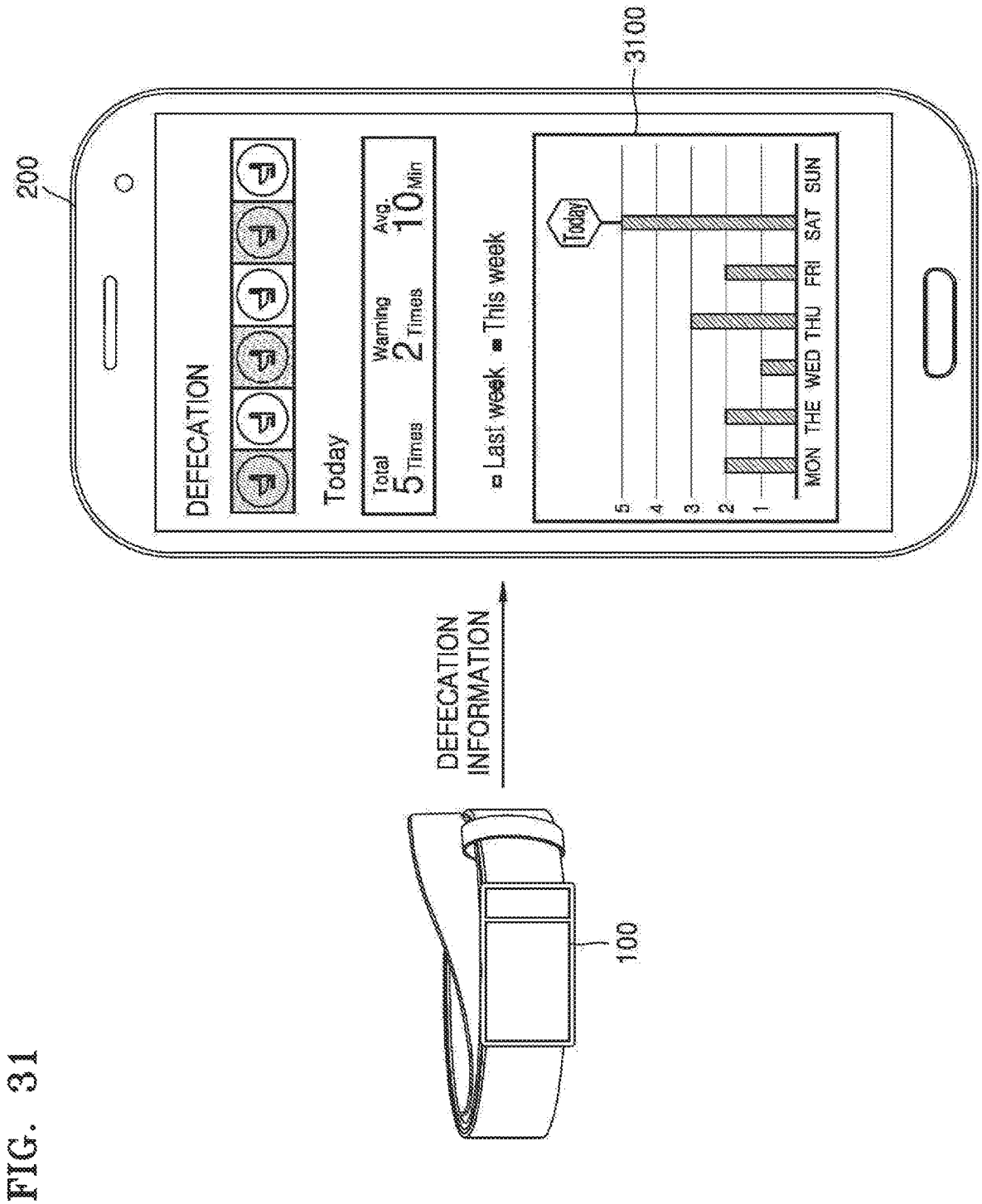
FIG. 31 illustrates a screen image that provides defecation information in units of weeks, according to an exemplary embodiment.

FIG. 31 illustrates a screen image that provides defecation information in units of weeks, according to an exemplary embodiment.

Referring to FIG. 31, the host terminal 200 may provide the defecation information in units of weeks. For example, the host terminal 200 may provide information 3100 about a defecation frequency for each day of the week in a bar graph form, but the inventive concept is not limited thereto.

According to an exemplary embodiment, when the user swipes horizontally while touching an area of the screen image on which bar graphs are displayed, the host terminal 200 may provide defecation information for last week.

Although not shown in FIG. 31, the host terminal 200 may provide the defecation information in units of months. For example, the host terminal 200 may display defecation frequency information on a calendar.

Figure 32:
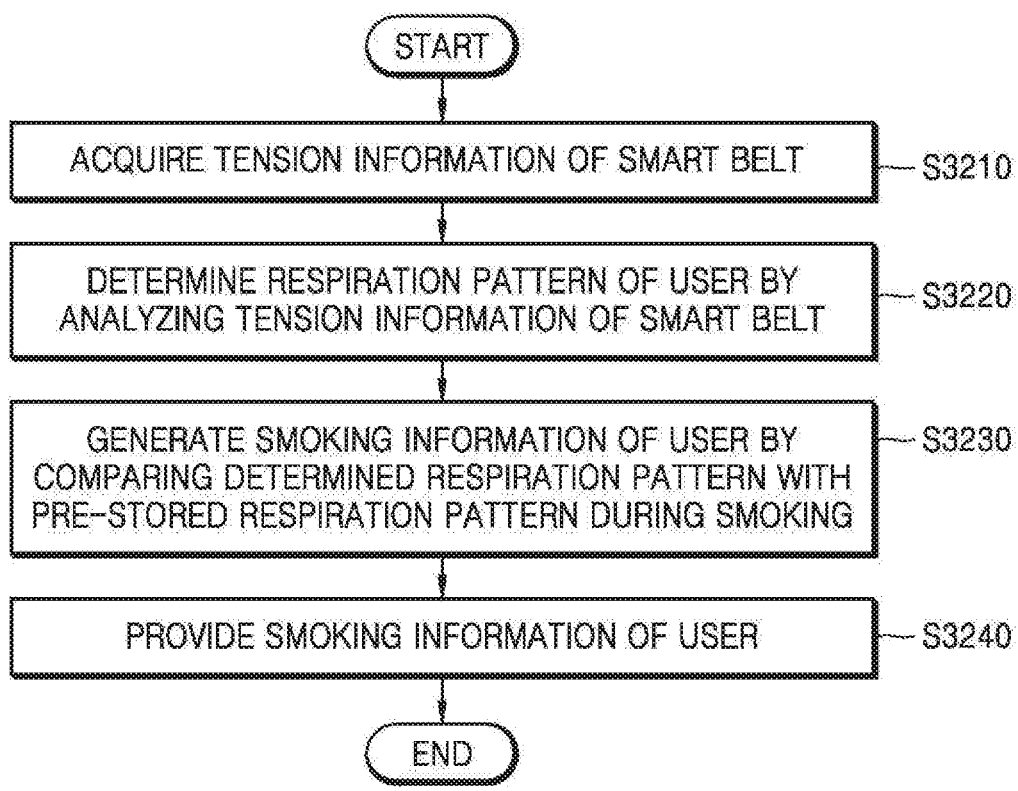
FIG. 32 is a flowchart of a method of providing smoking information of a user, according to an exemplary embodiment.

FIG. 32 is a flowchart of a method of providing smoking information of a user, according to an exemplary embodiment.

In operation S3210, the smart belt 100 may acquire tension information of the smart belt 100. For example, the smart belt 100 may measure a tension at a third point between the first and second points on the smart belt 100. A method in which the tension sensor 113 measures a tension has been described above, and thus a repeated description thereof will be omitted.

In operation S3220, the smart belt 100 may determine a respiration pattern of the user by analyzing the tension information of the smart belt 100.

For example, when the user breaths in a general state, a tension value may not greatly change. On the other hand, when the user breathes (e.g., inhales) deeply, the tension value may abruptly increase. Thus, when the tension value abruptly increases, the smart belt 100 may determine that the user is breathing deeply.

The smart belt 100 may determine the respiration pattern of the user by further taking into account acceleration information measured by the acceleration sensor. For example, when the user breaths in deeply and then breaths out, an acceleration value of the smart belt 100 may abruptly increase. Thus, when the acceleration value and the tension value greatly change, the smart belt 100 may determine that the user breathes in deeply and then breathes out.

In operation S3230, the smart belt 100 may generate smoking information of the user by comparing the determined respiration pattern with a pre-stored respiration pattern during smoking (hereinafter, referred to as a smoking pattern).

Figure 33:
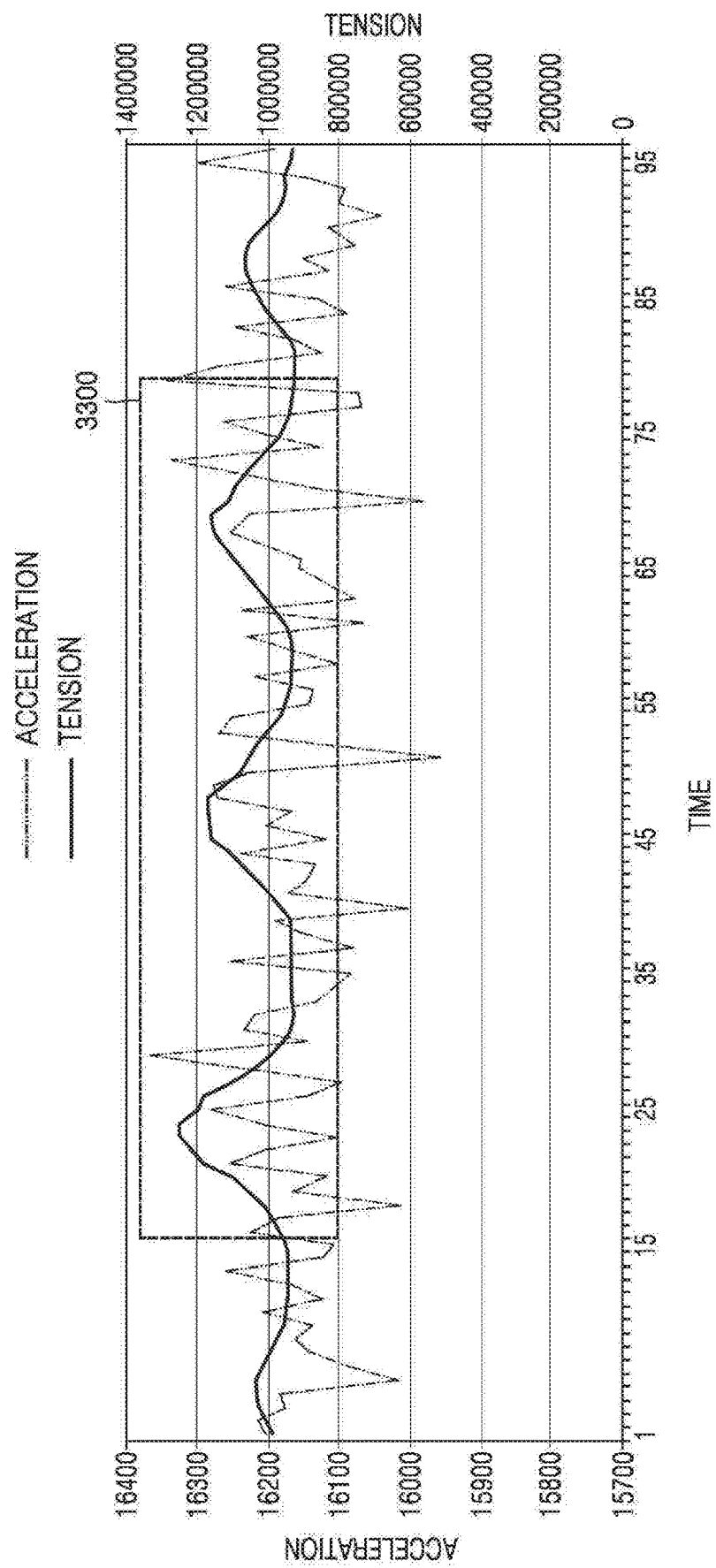
FIG. 33 illustrates a smoking pattern according to an exemplary embodiment.

The smoking pattern will now be described with reference to FIG. 33. When a user smokes, the user repeats breathing deeply in and then breathing out, and thus the abdomen expands more than usual. With the expansion of the abdomen, the tension value (or a tension variation) sensed by the smart belt 100 may increase. When a user smokes, the acceleration value (or an acceleration variation) measured by the acceleration sensor may also increase. Thus, referring to FIG. 33, the smart belt 100 may store, as a smoking pattern 3300, a change in a tension value and/or acceleration value when the user smokes.

According to an exemplary embodiment, when the respiration pattern of the user becomes similar to the smoking pattern 3300 while the smart belt 100 monitors the respiration pattern of the user, the smart belt 100 may determine that the user is smoking.

According to an exemplary embodiment, by comparing the respiration pattern of the user with the smoking pattern 3300, the smart belt 100 may generate smoking information including, but is not limited to, a smoking frequency for one day, smoking time points, an average smoking frequency for one week, and an average smoking time period. For example, the smoking information may further include information representing whether the smoking frequency for one day exceeds a reference smoking frequency (for example, 10 times a day). The reference smoking frequency may be determined by the user.

In operation S3240, the smart belt 100 may provide the smoking information of the user. For example, when the smart belt 100 includes a display, the smart belt 100 may display the smoking information of the user on the display.

The smart belt 100 may provide the smoking information via the host terminal 200 (e.g., a mobile terminal of the user). At this time, the user may check the smoking information via the host terminal 200. For example, the user may execute a specific application installed on the host terminal 200 and check the smoking information generated by the smart belt 100 via an execution screen image of the specific application. The smoking information provided by the host terminal 200 will now be described in more detail with reference to FIG. 34.

Figure 34:
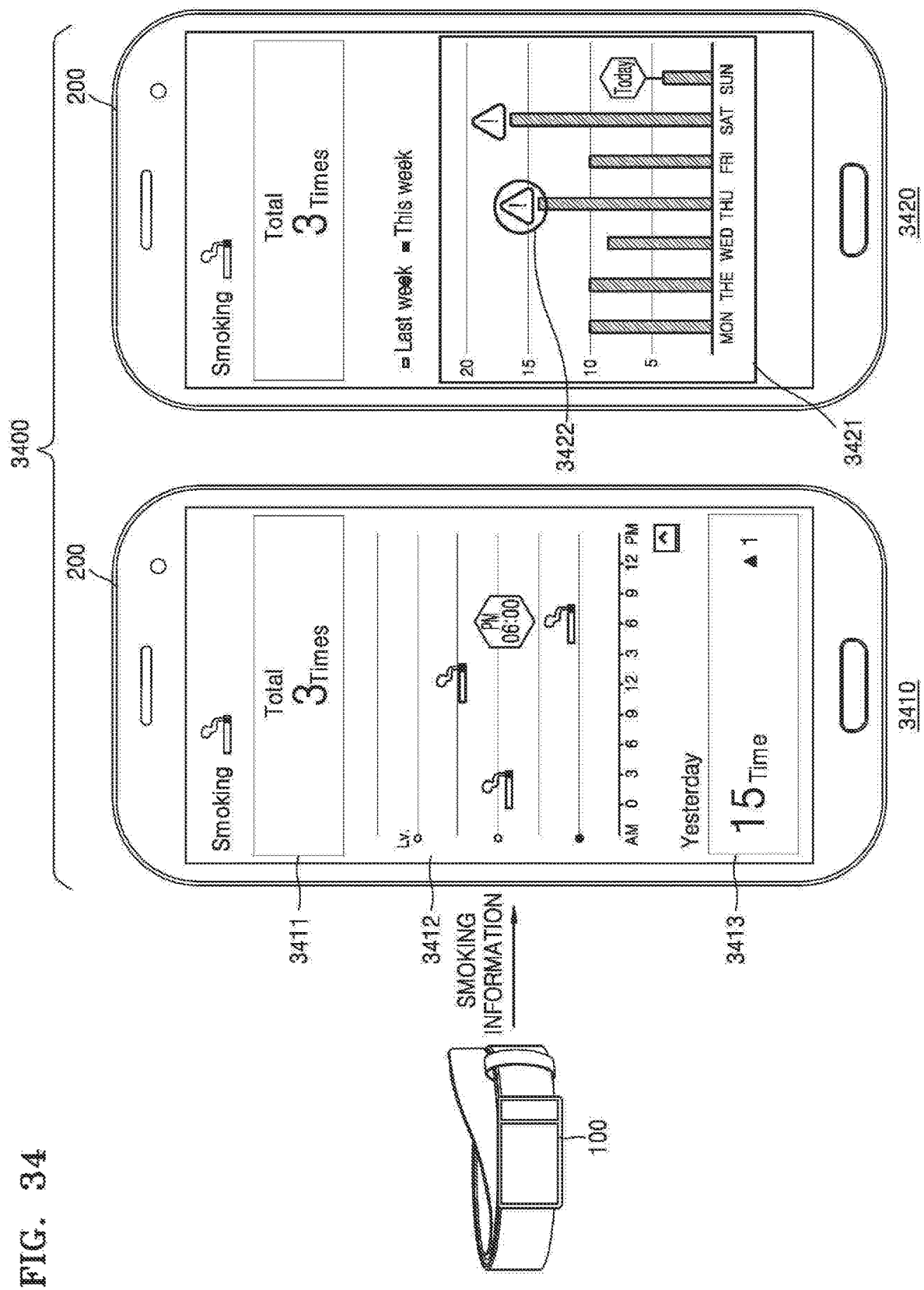
FIG. 34 illustrates screen images that provide smoking information of a user, according to an exemplary embodiment.

FIG. 34 illustrates screen images that provide smoking information of a user, according to an exemplary embodiment. Referring to FIG. 34, the smart belt 100 may generate the smoking information of the user, based on a result of comparing a respiration pattern of the user with a pre-stored smoking pattern. According to an exemplary embodiment, the comparison between the respiration pattern and the smoking pattern may include comparing a measured tension value with a tension value included in the smoking pattern.

According to an exemplary embodiment, the smart belt 100 may transmit the generated smoking information to the host terminal 200. In this case, the host terminal 200 may display the smoking information on the screen thereof, as shown in example screens 3400.

Referring to a screen image 3410, the host terminal 200 may provide smoking information in units of days. For example, the host terminal 200 may display information 3411 about a smoking frequency for today (for example, 3). The host terminal 200 may also provide a graph 3412 showing smoking time points and smoking levels, by using a cigarette icon. A smoking level may correspond to a smoking hour. For example, when a smoking hour is long, the smart belt 100 may determine that the user smoked several cigarettes. Thus, the smoking level may increase with an increase in the smoking hour. The host terminal 200 may also provide information 3413 about a smoking frequency for yesterday.

Referring to a screen image 3420, the host terminal 200 may provide the smoking information in units of weeks. For example, the host terminal 200 may provide information 3421 about a smoking frequency for each day of the week in a bar graph form, but the inventive concept is not limited thereto. The host terminal 200 may display a warning icon 3422 on the day when the user smoked more times than the reference smoking frequency (for example, 10 times).

According to an exemplary embodiment, when the user swipes horizontally while touching an area of the screen image on which bar graphs are displayed, the host terminal 200 may provide smoking information for last week.

Although not shown in FIG. 34, the host terminal 200 may provide smoking information in units of months or any other various temporal units. For example, the host terminal 200 may display smoking frequency information on a calendar.

Figure 35:
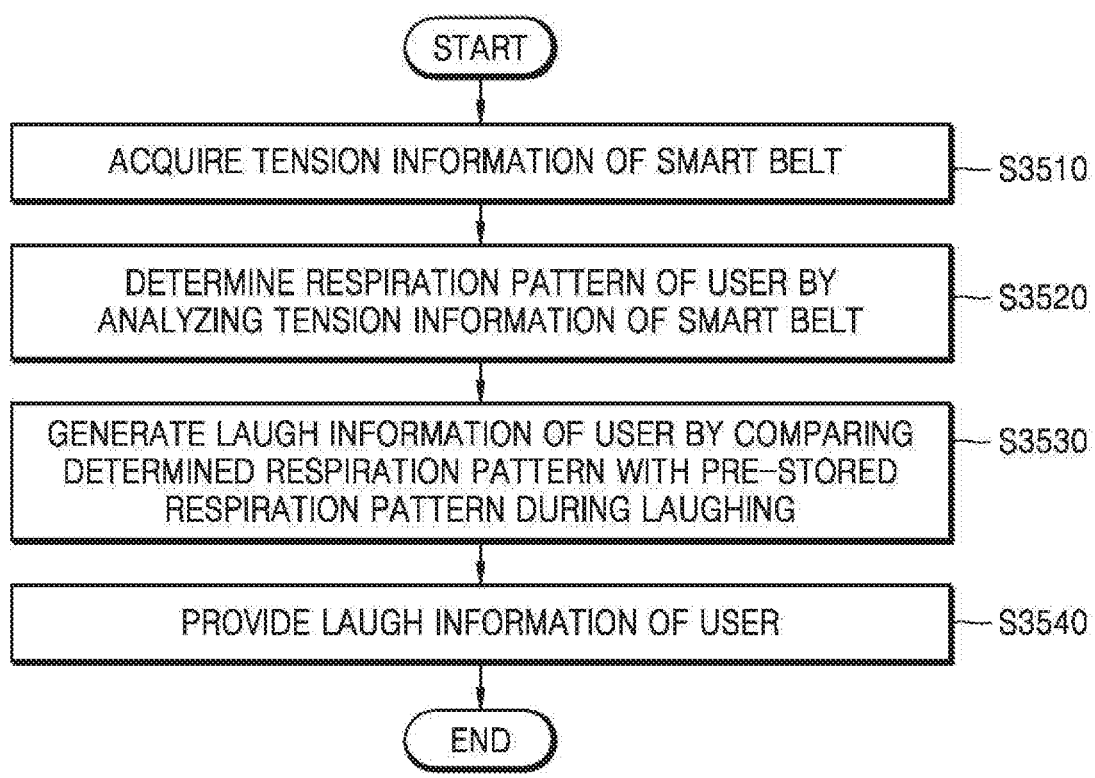
FIG. 35 is a flowchart of a method of providing laugh information of a user, according to an exemplary embodiment.

FIG. 35 is a flowchart of a method of providing laugh information of a user, according to an exemplary embodiment.

In operation S3510, the smart belt 100 may acquire tension information of the smart belt 100. For example, the smart belt 100 may measure a tension at a third point between the first and second points on the smart belt 100.

In operation S3520, the smart belt 100 may acquire the respiration pattern of the user, based on the tension information.

Since operations S3510 and S3520 correspond to operations S3210 and S3220 of FIG. 31, a repeated description thereof will be omitted.

In operation S3530, the smart belt 100 may generate laugh information of the user by comparing the determined respiration pattern with a pre-stored respiration pattern during laughing (hereinafter, referred to as a laughing pattern).

Figure 36:
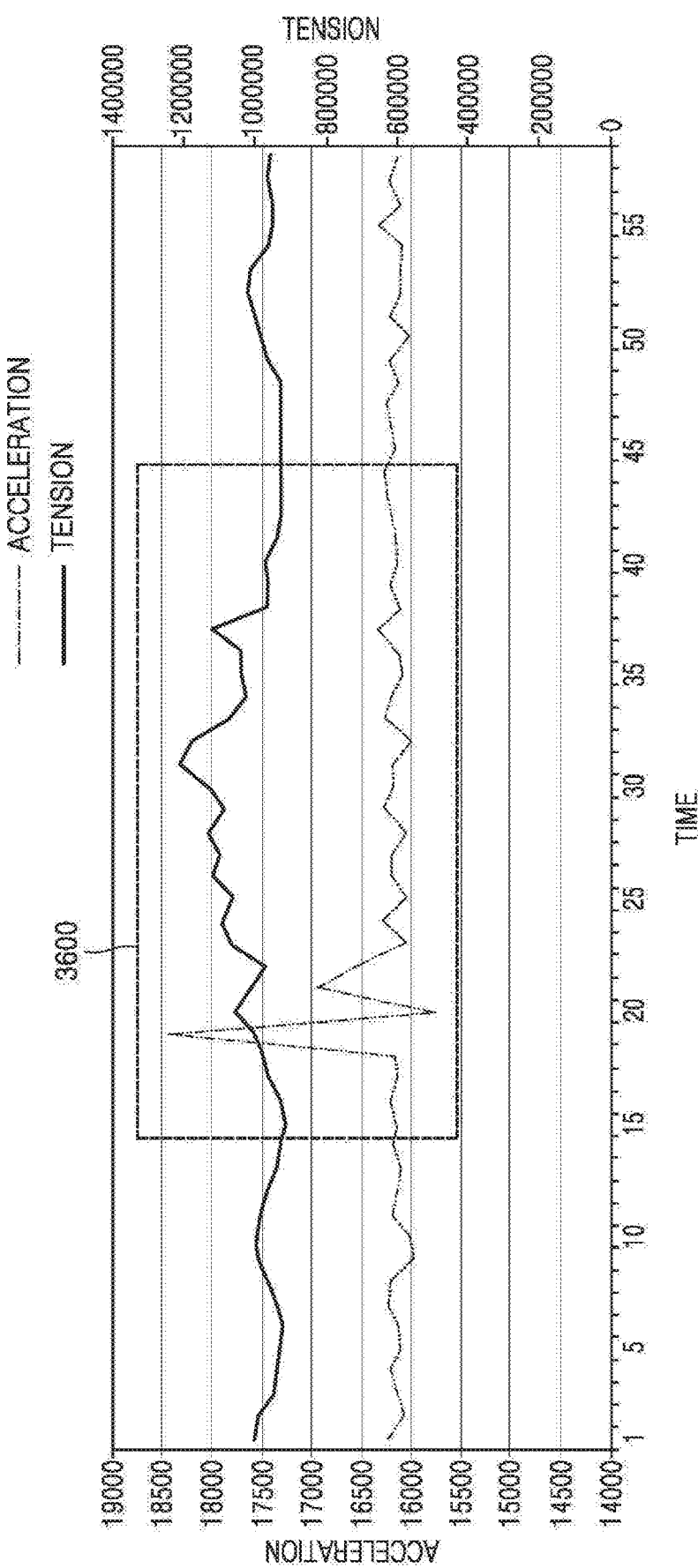
FIG. 36 illustrates a laughing pattern according to an exemplary embodiment.

The laughing pattern will now be described in detail with reference to FIG. 36. When a user laughs, the abdomen of the user is tensed, and thus a tension value (or a tension variation value) measured by the smart belt 100 may abruptly increase. When a user laughs, an acceleration value (or an acceleration variation) measured by the smart belt 100 may also increase. Thus, referring to FIG. 36, the smart belt 100 may store, as a laughing pattern 3600, a change in a tension value and/or acceleration value when the user laughs.

According to an exemplary embodiment, when the respiration pattern of the user becomes similar to the laughing pattern 3600 while the smart belt 100 monitors the respiration pattern of the user, the smart belt 100 may determine that the user is laughing. Thus, by comparing the respiration pattern of the user with the laughing pattern 3600, the smart belt 100 may generate laugh information including, but is not limited to, a laughing frequency for one day, laughing time points, and an average laughing frequency for one week. For example, the laugh information may include a laughing intensity (level). The smart belt 100 may determine the laughing intensity (or level), based on a laughing duration or a variation of the tension value.

In operation S3540, the smart belt 100 may provide the laugh information of the user.

For example, when the smart belt 100 includes a display, the smart belt 100 may display the laugh information of the user on the display.

The smart belt 100 may provide the laugh information via the host terminal 200 (e.g., a mobile terminal of the user). At this time, the user may check the laugh information via the host terminal 200. For example, the user may execute a specific application installed on the host terminal 200 and check the laugh information generated by the smart belt 100 via an execution screen image of the specific application. The laugh information provided by the host terminal 200 will now be described in more detail with reference to FIG. 37.

Figure 37:
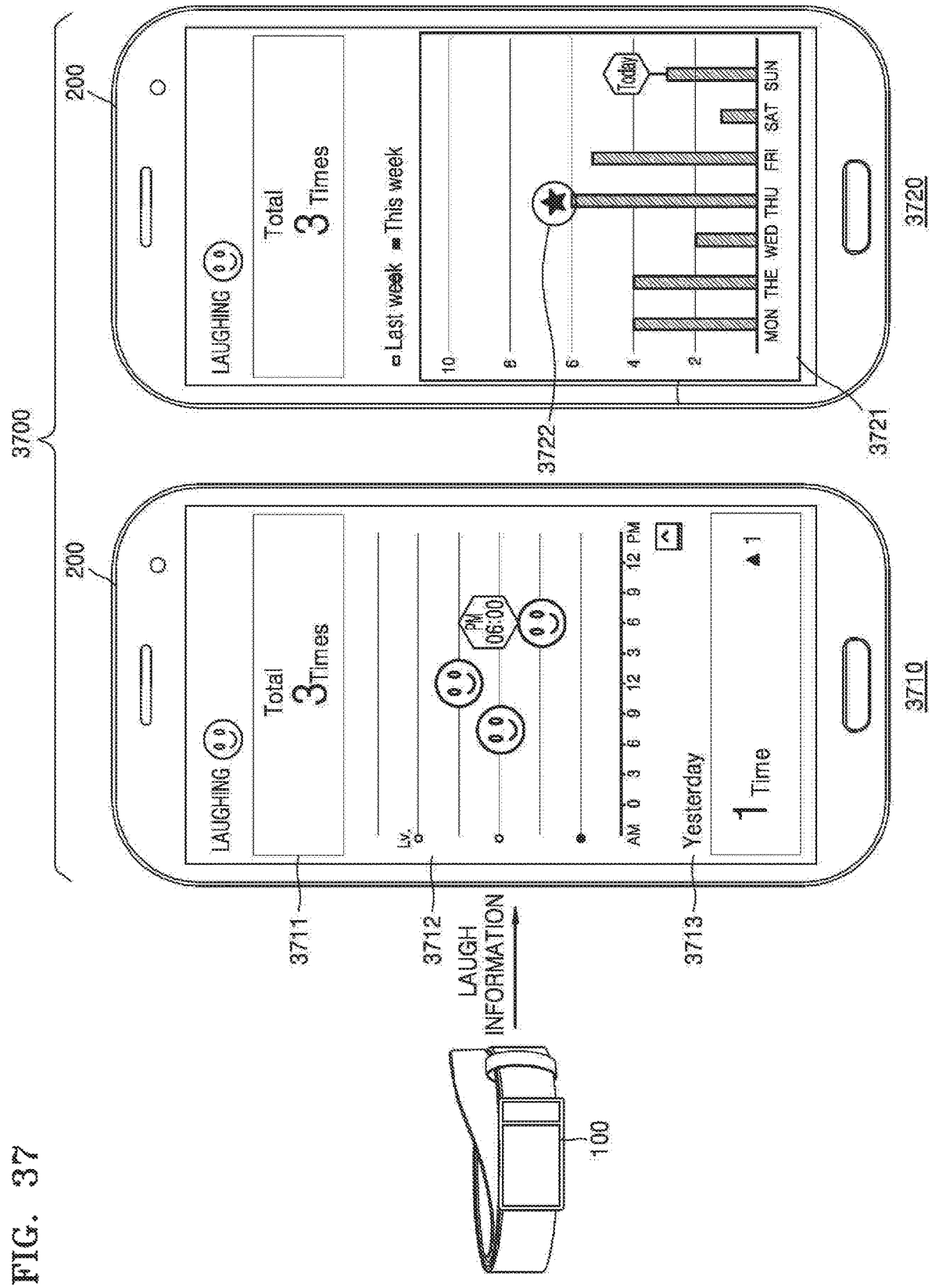
FIG. 37 illustrates screen images that provide laugh information of a user, according to an exemplary embodiment.

FIG. 37 illustrates screen images that provide laugh information of a user, according to an exemplary embodiment.

Referring to FIG. 37, the smart belt 100 may generate the laugh information of the user, based on a result of comparing a respiration pattern of the user with a pre-stored laughing pattern. According to an exemplary embodiment, the comparison between the respiration pattern and the laughing pattern may include comparing a measured tension value with a tension value included in the laughing pattern.

According to an exemplary embodiment, the smart belt 100 may transmit the generated laugh information to the host terminal 200. In this case, the host terminal 200 may display the laugh information on the screen thereof, as shown in example screens 3700.

Referring to a screen image 3710, the host terminal 200 may provide laugh information in units of days. For example, the host terminal 200 may display information 3711 about a laughing frequency for today (for example, 3). The host terminal 200 may also provide a graph 3712 showing laughing time points and laughing levels, by using a smile icon. A laughing level may correspond to the laughing duration, the variation of the tension value, and the like. The host terminal 200 may also provide information 3713 about a laughing frequency for yesterday.

Referring to a screen image 3720, the host terminal 200 may provide the laugh information in units of weeks. For example, the host terminal 200 may provide information 3721 about a laughing frequency for each day of the week in a bar graph form, but the inventive concept is not limited thereto. The host terminal 200 may display a complementing icon 3722 on the day when the user laughed more times than the reference laughing frequency (for example, 5 times).

According to an exemplary embodiment, when the user swipes horizontally while touching an area of the screen image on which bar graphs are displayed, the host terminal 200 may provide laugh information for last week. Although not shown in FIG. 37, the host terminal 200 may provide laugh information in units of months. For example, the host terminal 200 may display laughing frequency information on a calendar.

Figure 38:
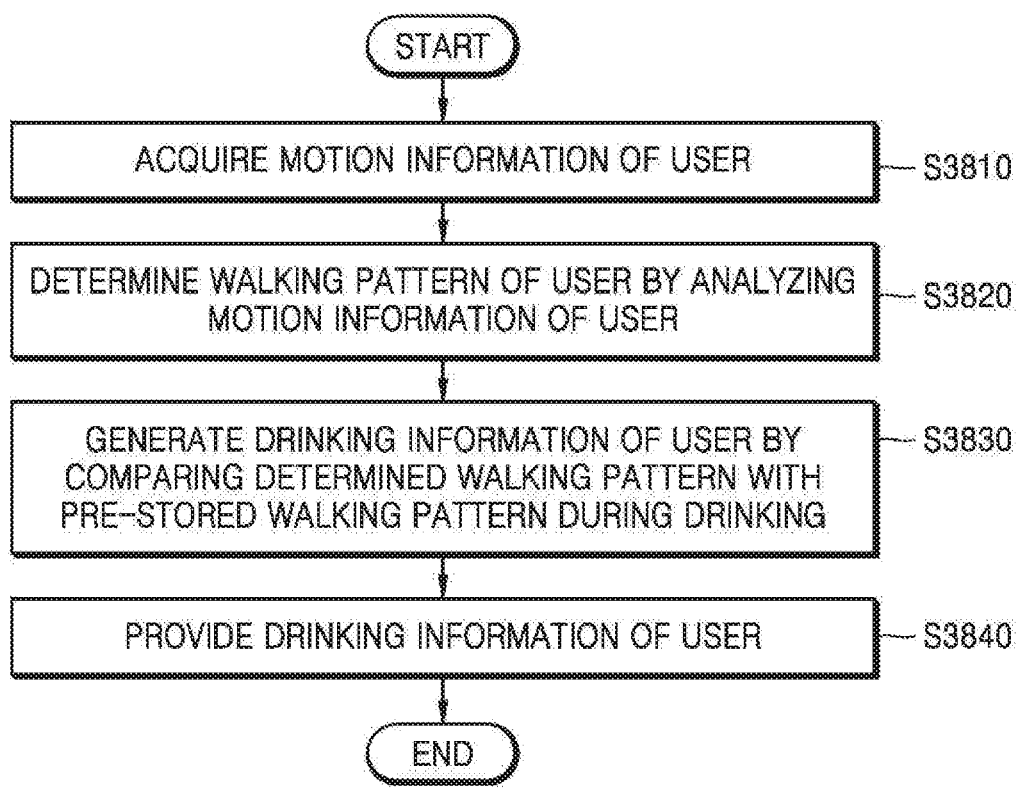
FIG. 38 is a flowchart of a method of providing drinking information of a user, according to an exemplary embodiment.

FIG. 38 is a flowchart of a method of providing drinking information of a user, according to an exemplary embodiment.

In operation S3810, the smart belt 100 may acquire motion information of a user who wears the smart belt 100.

According to an exemplary embodiment, the smart belt 100 may sense a motion of the user by using the inertia sensor 111 and the tension sensor 113. For example, the smart belt 100 may acquire at least one of a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor. The smart belt 100 may acquire the tension information of the smart belt 100 by using the tension sensor 113.

In operation S3820, the smart belt 100 may acquire a walking pattern of the user by analyzing the motion information of the user.

According to an exemplary embodiment, the smart belt 100 may determine whether the user is in a stopped state, a walking state, or a running state, by using at least one of an acceleration value, an inclination value, a position value, and a pressure value. When the smart belt 100 determines that the user is walking, the smart belt 100 may also determine whether the user walks in a staggering manner or straight, by using the acceleration sensor or the gyroscope sensor. Thus, the smart belt 100 may determine a current walking pattern of the user, based on a sensor value received from at least one sensor.

In operation S3830, the smart belt 100 may generate drinking information of the user by comparing the determined walking pattern with a walking pattern after drinking (hereinafter, referred to as a drinking pattern). The drinking information may include, but is not limited to, a drinking cycle, a drinking frequency, and information about days of the week on which the user drank alcohol.

Figure 39:
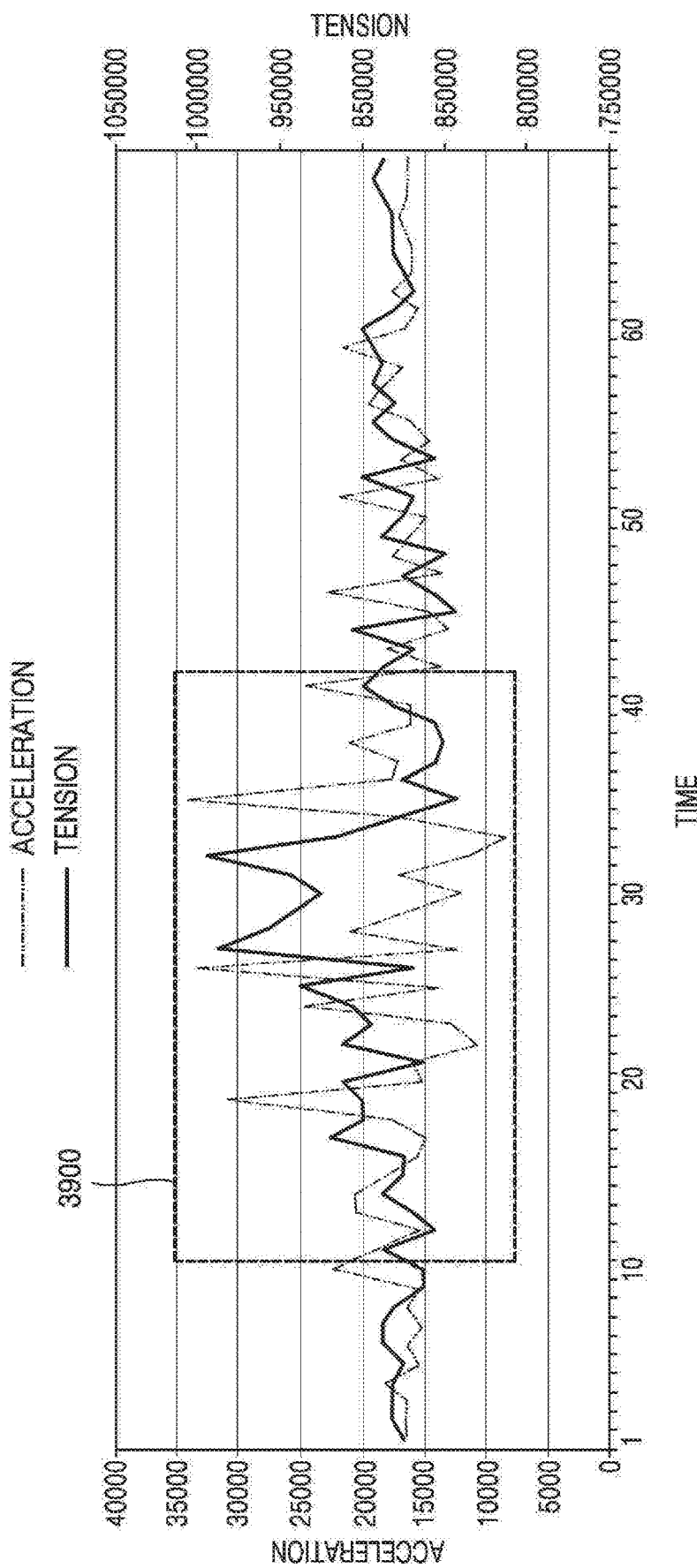
FIG. 39 illustrates a drinking pattern according to an exemplary embodiment.

The drinking pattern will now be described in detail with reference to FIG. 39. When a user is drunk, the user may not walk in a normal manner. Thus, when the user is in a drunken state, an acceleration value and a tension value measured by the smart belt 100 may more greatly fluctuate than when the user is in a normal state. Thus, referring to FIG. 39, the smart belt 100 may store, as a drinking pattern 3900, a change in a tension value and/or acceleration value when the user is drunk.

According to an exemplary embodiment, when the walking pattern of the user becomes similar to the drinking pattern 3900 while the smart belt 100 monitors the walking pattern of the user, the smart belt 100 may determine that the user drank alcohol. Thus, by comparing the walking pattern of the user with the drinking pattern 3900, the smart belt 100 may generate drinking information including, but is not limited to, a drinking frequency for one week and days of the week on which the user drank alcohol. For example, the drinking information may include a drinking intensity (or level). The drinking intensity (or level) may correspond to a degree to which the user is drunk. Since fluctuation of the acceleration value may increase as the user becomes more severely drunk, the smart belt 100 may determine the drinking intensity (or level), based on an amount of change of the acceleration value or tension value.

In operation S3840, the smart belt 100 may provide the drinking information of the user. For example, when the smart belt 100 includes a display, the smart belt 100 may display the drinking information of the user on the display.

The smart belt 100 may provide the drinking information via the host terminal 200 (e.g., a mobile terminal of the user). At this time, the user may check the drinking information via the host terminal 200. For example, the user may execute a specific application installed on the host terminal 200 and check the drinking information generated by the smart belt 100 via an execution screen image of the specific application. The drinking information provided by the host terminal 200 will now be described in more detail with reference to FIG. 40.

Figure 40:
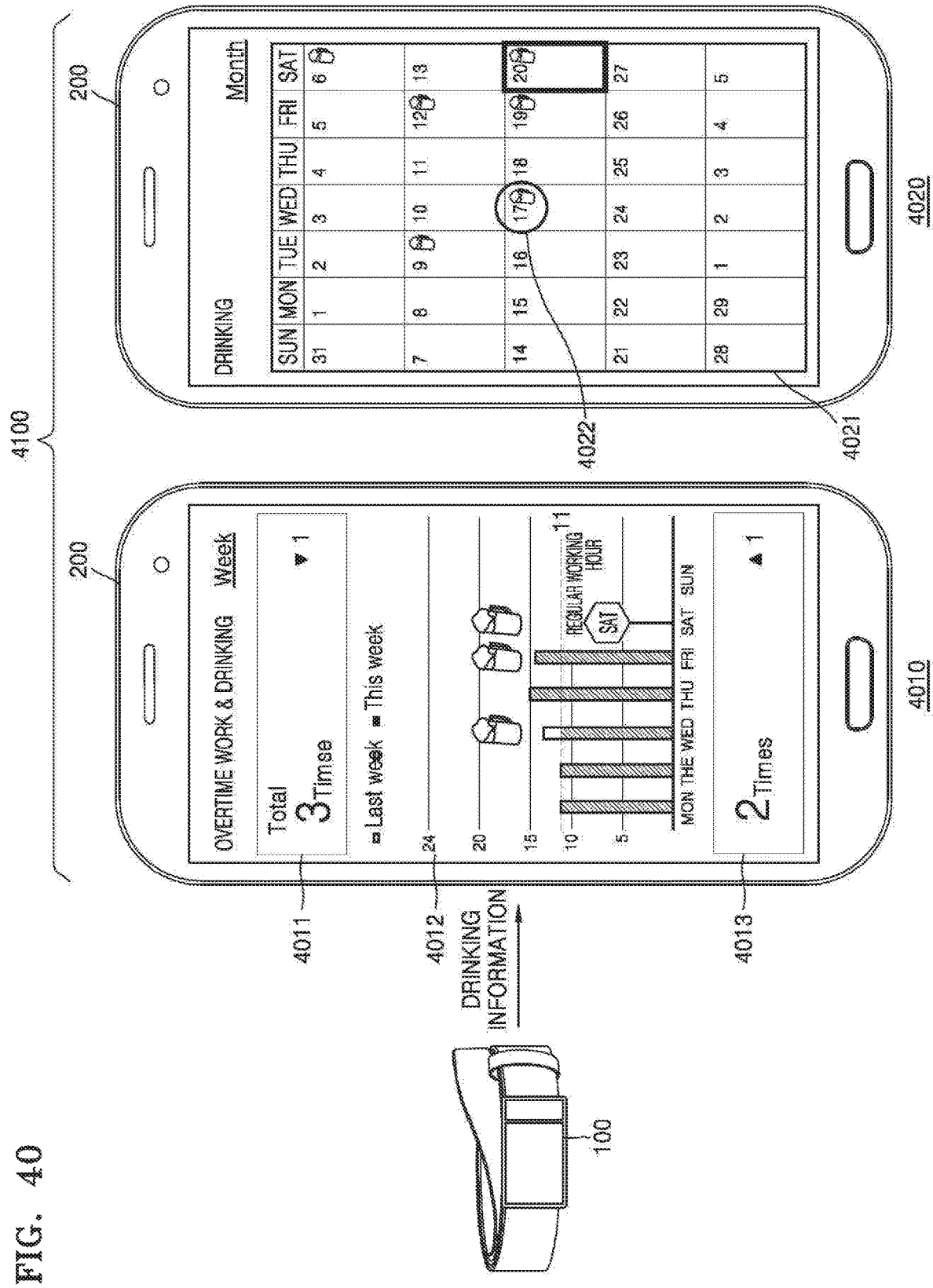
FIG. 40 illustrates screen images that provide drinking information of a user, according to an exemplary embodiment.

FIG. 40 illustrates screen images that provide drinking information of a user, according to an exemplary embodiment.

Referring to FIG. 40, the smart belt 100 may generate the drinking information of the user, based on a result of comparing a walking pattern of the user with a pre-stored drinking pattern. According to an exemplary embodiment, the comparison between the walking pattern and the drinking pattern may include comparing a measured acceleration value with an acceleration value included in the drinking pattern.

According to an exemplary embodiment, the smart belt 100 may transmit the generated drinking information to the host terminal 200. In this case, the host terminal 200 may display the drinking information on the screen thereof, as shown in example screens 4100.

Referring to a screen image 4010, the host terminal 200 may provide drinking information in units of weeks. For example, the host terminal 200 may display information 4011 about a drinking frequency for this week (for example, 3). The host terminal 200 may also provide a graph 4012 showing days of the week on which the user drank alcohol, by using an icon representing to an image of drinking (e.g., an image of a bear glass). The host terminal 200 may display information 4013 about a drinking frequency for last week (for example, 2).

Referring to a screen image 4020, the host terminal 200 may provide the drinking information in units of months. For example, the host terminal 200 may display an indicator 4022 indicating the day on which the user drank alcohol, on a calendar 4021. For example, the host terminal 200 may display a beer glass image icon on the day when the user drank alcohol, but the inventive concept is not limited thereto.

Figure 41:
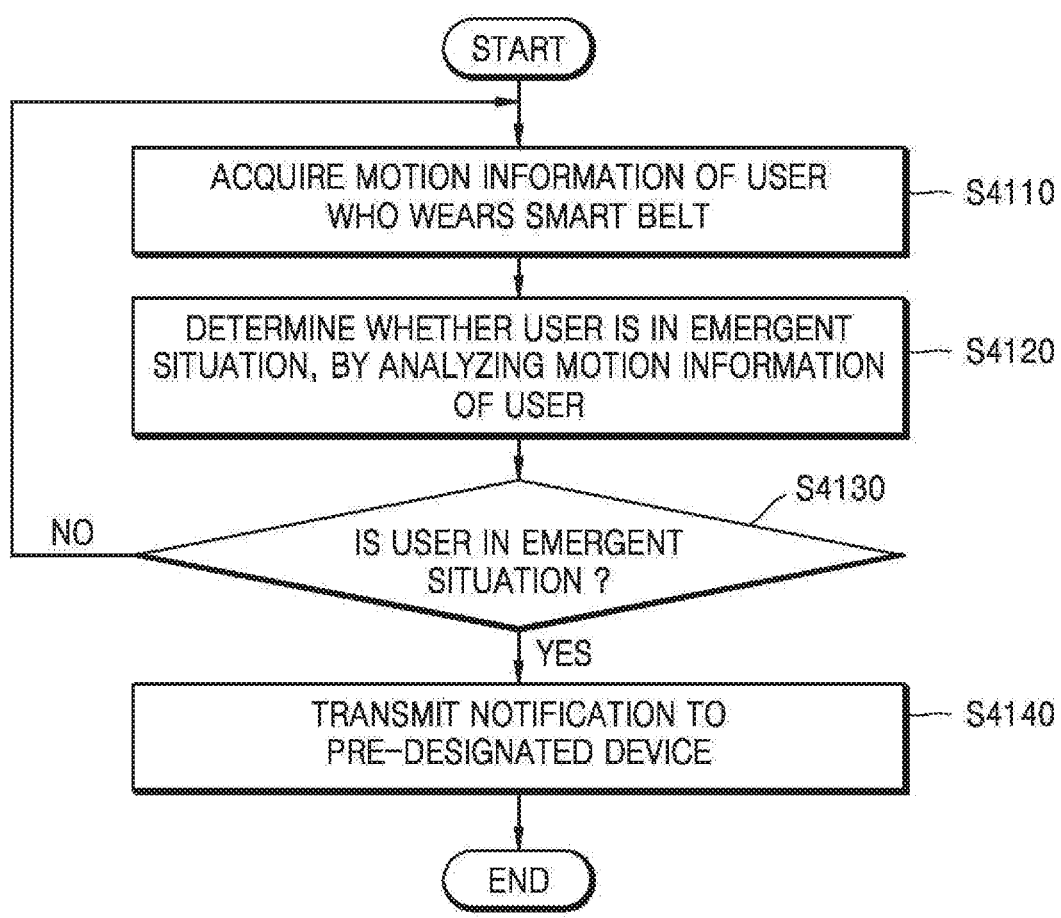
FIG. 41 is a flowchart of a method of transmitting a notification message to a pre-designated device when a user is in an emergent situation, according to an exemplary embodiment.

FIG. 41 is a flowchart of a method of transmitting a notification message to a pre-designated device when a user is in an emergent situation, according to an exemplary embodiment.

In operation S4110, the smart belt 100 may acquire motion information of a user who wears the smart belt 100.

According to an exemplary embodiment, the smart belt 100 may sense a motion of the user by using the inertia sensor 111 and the tension sensor 113. For example, the smart belt 100 may acquire a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor. The smart belt 100 may acquire the tension information of the smart belt 100 by using the tension sensor 113.

In operation S4120, the smart belt 100 may determine whether the user is in an emergent situation, by analyzing the motion information of the user.

According to an exemplary embodiment, the smart belt 100 may determine whether the user is in an emergent situation, by comparing the motion information of the user with emergent situation pattern information. The emergent situation pattern information may be data indicating a motion pattern corresponding to at least one emergent situation. For example, the emergent situation pattern information may include, but is not limited to, a motion pattern appearing during a seizure (hereinafter, referred to as a seizure pattern) and a motion pattern appearing during falling (hereinafter, referred to as a falling pattern).

Figure 42:
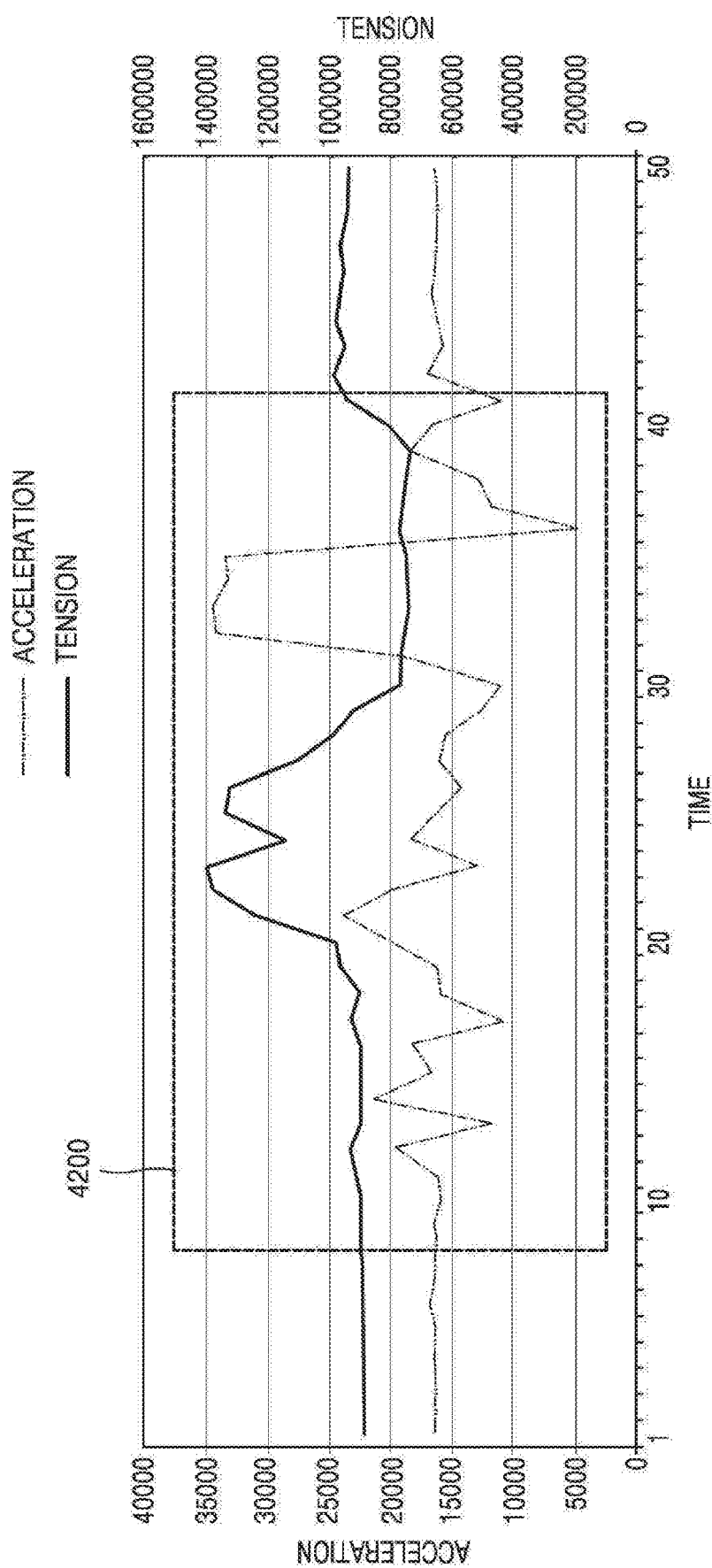
FIG. 42 illustrates a seizure pattern according to an exemplary embodiment.

The seizure pattern will now be described in detail with reference to FIG. 42. When a user has a seizure due to epilepsy or the like, the user may generally lie down and writhe uncontrollably. In this case, a value of one axis among 3-axis acceleration values (for example, a z axis) may not greatly change, and values of the other two axes (for example, x and y axes) may abruptly change. Moreover, since a force is applied to the smart belt 100 worn by the user due to a seizure of the user, the tension value of the smart belt 100 may abruptly change.

According to an exemplary embodiment, the smart belt 100 may store, as a seizure pattern 4200, a change in a tension value and/or acceleration value when the user has a seizure. When the motion of the user becomes similar to the seizure pattern 4200 while the smart belt 100 monitors the motion of the user, the smart belt 100 may determine that the user is having a seizure.

Figure 43:
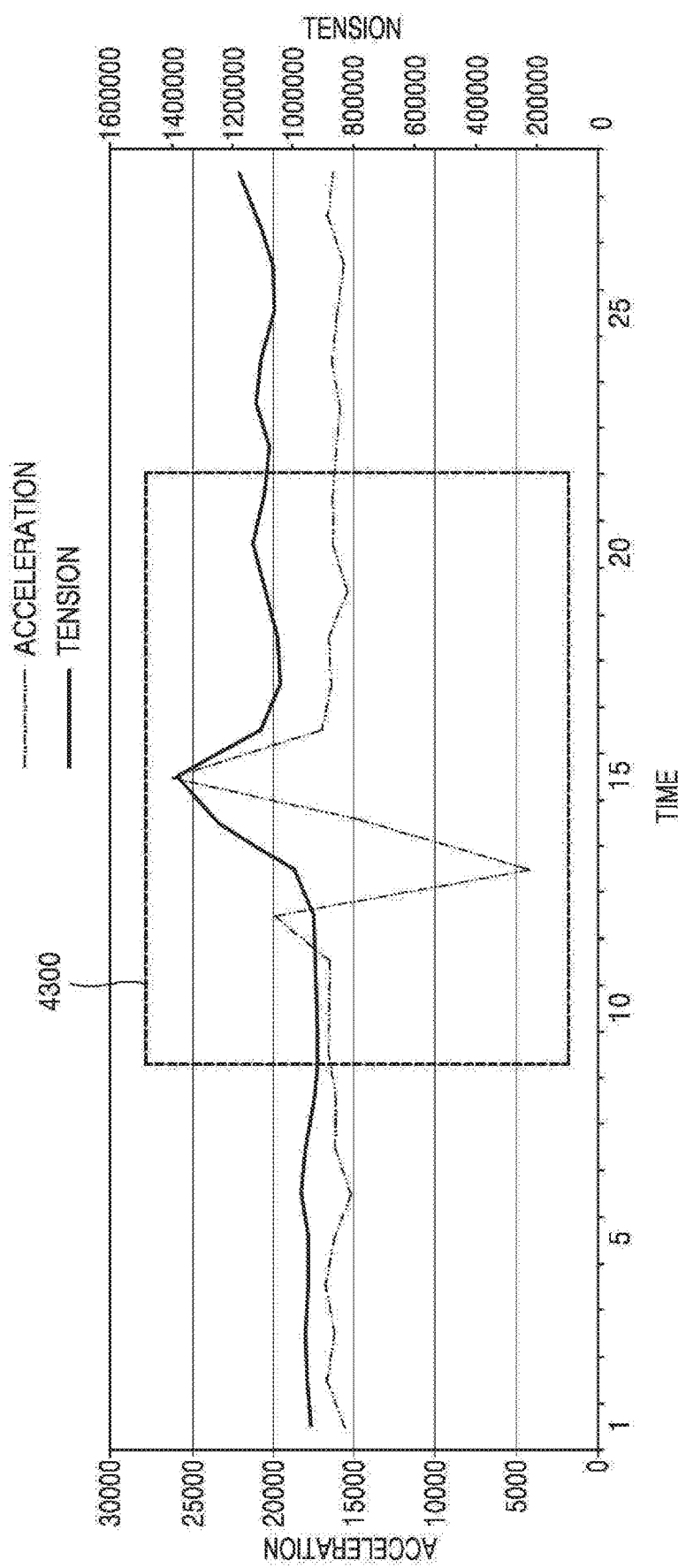
FIG. 43 illustrates a fall pattern according to an exemplary embodiment.

The falling pattern will now be described in detail with reference to FIG. 43. When a user falls, an acceleration value measured by the smart belt 100 may abruptly change. When an acceleration sensor included in the smart belt 100 is a 3-axis acceleration sensor, the acceleration sensor may sense that an acceleration value of an axis from three axes greatly changes. Moreover, since a force is applied to the smart belt 100 worn by the user due to a fall of the user, the tension value of the smart belt 100 may also abruptly change.

According to an exemplary embodiment, the smart belt 100 may store, as a fall pattern 4300, a change in a tension value and/or acceleration value when the user falls. When the motion of the user becomes similar to the fall pattern 4300 while the smart belt 100 monitors the motion of the user, the smart belt 100 may determine that the user has fallen.

According to an exemplary embodiment, when the user had a seizure or fell, the smart belt 100 may determine that the user is in an emergent situation.

In operation S4130, when the smart belt 100 determines that the user is not in an emergent situation, as a result of the comparison between the motion information of the user and the emergent situation pattern information, the smart belt 100 may continue to monitor the motion of the user. In operation S4140, when the smart belt 100 determines that the user is in an emergent situation, the smart belt 100 may transmit a notification to a pre-designated device. For example, the smart belt 100 may transmit, to a device of an emergency contact person or guardian of the user, a notification indicating that the user is in an emergent situation. The smart belt 100 may also transmit the notification to a medical institution server or an emergency server. An operation, performed by the smart belt 100, of transmitting a notification will now be described in more detail with reference to FIG. 44.

Figure 44:
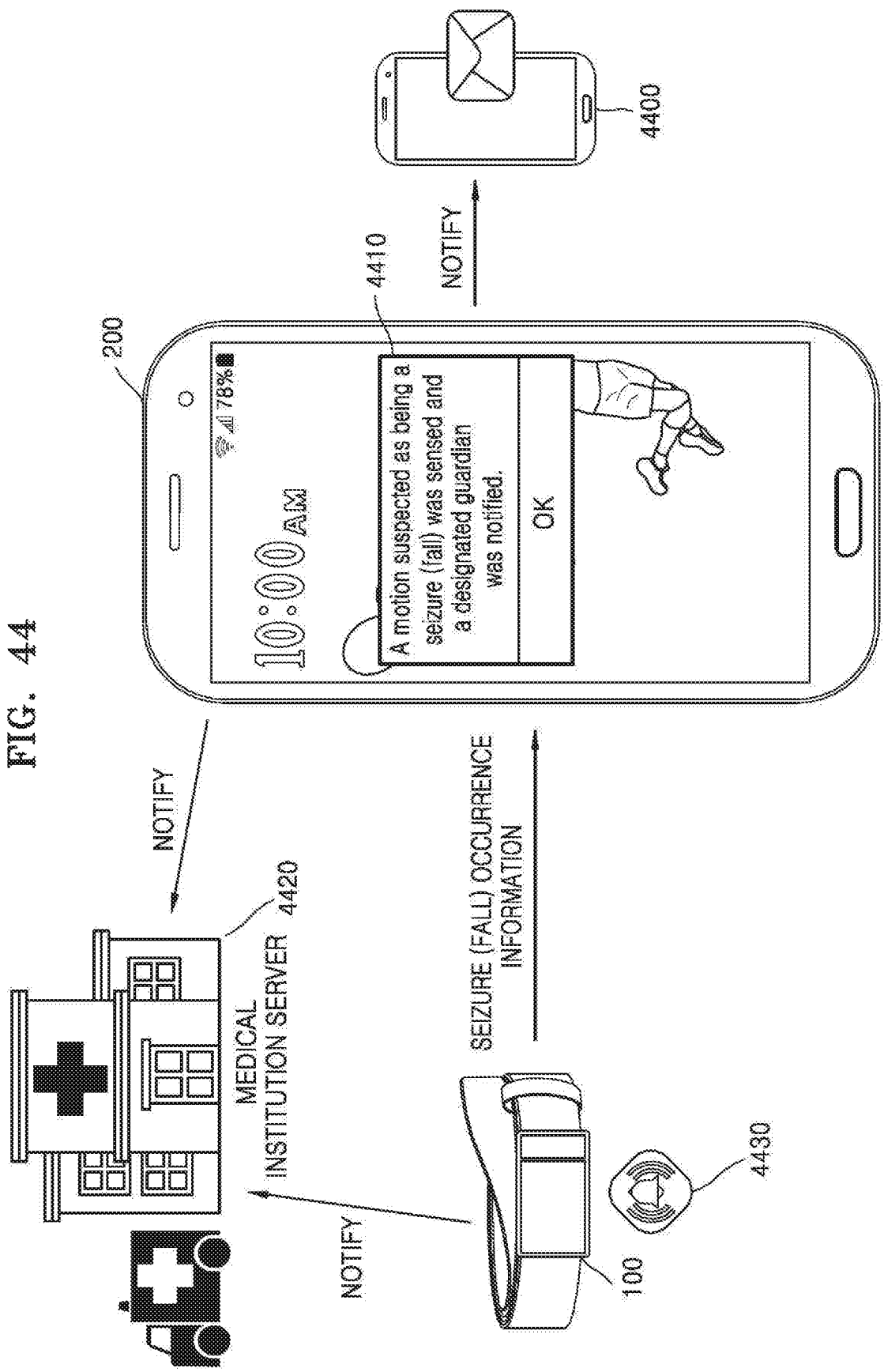
FIG. 44 is a view for explaining an operation of a smart belt when a smart belt has sensed an emergent situation of a user, according to an exemplary embodiment.

FIG. 44 is a view for explaining an operation of the smart belt 100 when the smart belt 100 has sensed an emergent situation of a user, according to an exemplary embodiment.

Referring to FIG. 44, the smart belt 100 may sense that the user had a seizure or fell, while monitoring a motion of the user who wears the smart belt 100. At this time, the smart belt 100 may provide seizure (or fall) occurrence information to the host terminal 200 (e.g., a mobile terminal of the user).

In response to the seizure (or fall) occurrence information from the smart belt 100, the host terminal 200 may transmit a notification message to a device 4400 (for example, a device of a pre-stored emergency contact person or guardian). The host terminal 200 may output a message (for example, 'A motion suspected as being a seizure (fall) was sensed and thus a designated guardian was notified.') via a popup window 4410.

The host terminal 200 may also transmit the notification to a medical institution server 4420. For example, the host terminal 200 may transmit, to the medical institution server 4420, a message requesting for an ambulance in addition to state information (for example, occurrence of a seizure or fall) and current location information.

According to an exemplary embodiment, the smart belt 100 may transmit the notification message directly to the device 4400 (for example, a device of a pre-stored emergency contact person or guardian) or transmit a notification to the medical institution server 4420. When the user is in an emergent situation, the smart belt 100 may output an alarm signal 4430 (for example, an audio signal or a vibration signal).

FIGS. 25-44 illustrate a case where the smart belt 100 generates activity information of a user, but the inventive concept is not limited thereto. For example, the host terminal 200 may generate the activity information of the user.

A case where the host terminal 200 generates activity information of a user will now be described in detail with reference to FIG. 45.

Figure 45:
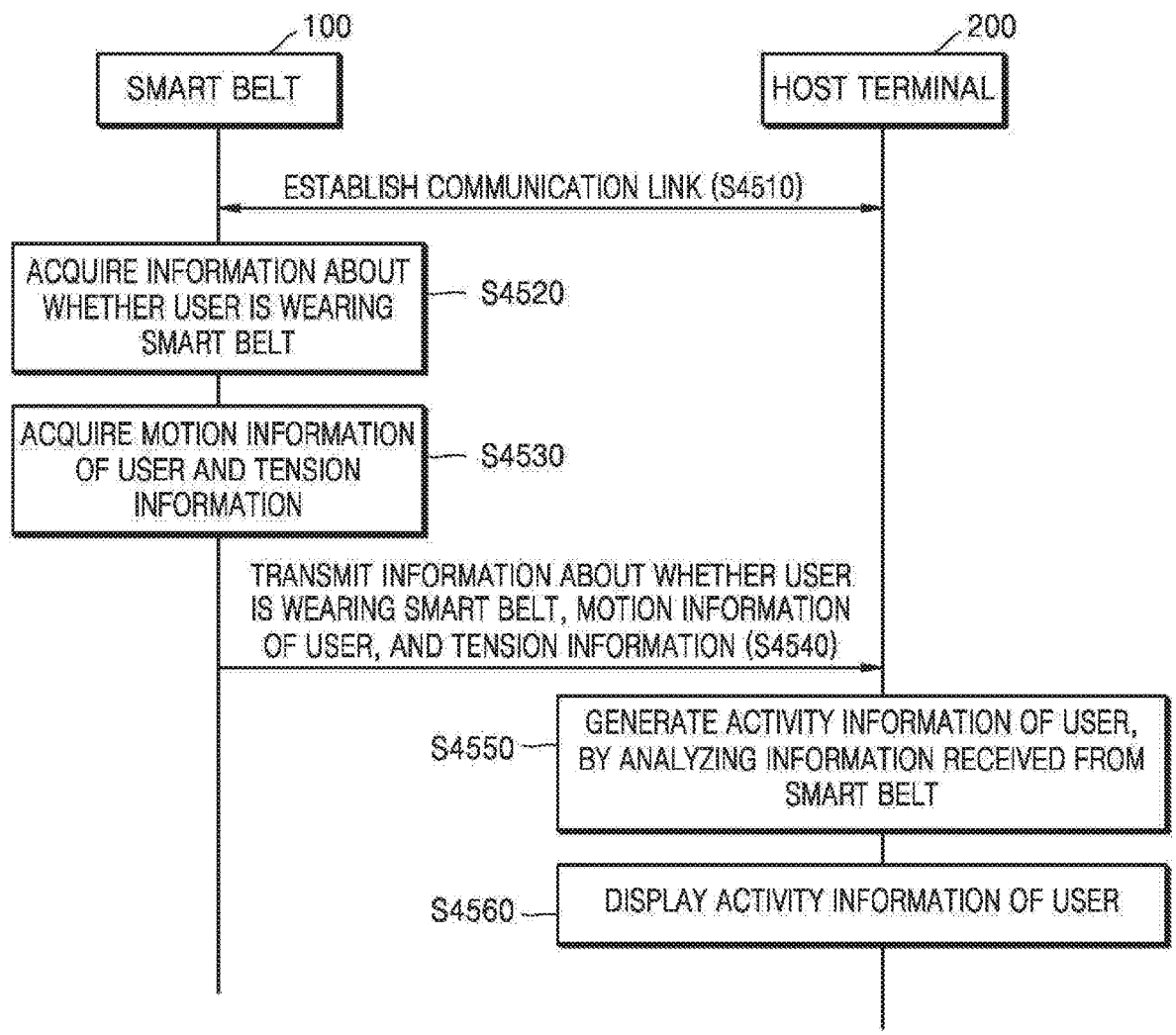
FIG. 45 is a flowchart of a method in which a host terminal generates activity information of a user, according to an exemplary embodiment.

FIG. 45 is a flowchart of a method in which a host terminal generates activity information of a user, according to an exemplary embodiment.

In operation S4510, the smart belt 100 and the host terminal 200 may establish a communication link therebetween.

For example, the smart belt 100 may establish a local area communication link with the host terminal 200 and/or may establish a mobile communication link (for example, 3G, 4G, or 5G) with the host terminal 200. Examples of the local area communication may include, but is not limited to, Bluetooth, Bluetooth Low Energy (BLE), Wi-Fi Direct, ultra wideband (UWB), Zigbee, Near Field Communication (NFC), and Ant+.

In operation S4520, the smart belt 100 may acquire information about whether the user is wearing the smart belt 100. The information about whether the user is wearing the smart belt 100 may include, but is not limited to, wearing start time information (for example, 8 A.M.) representing a time when the user starts wearing the smart belt 100, wearing end time information (for example, 10 P.M.) representing a time when the user takes off the smart belt 100, wearing/taking-off frequency information (for example, 5 times) representing how often the user puts on and takes off the smart belt 100 in one day, and information about whether the user is currently wearing the smart belt 100.

According to an exemplary embodiment, the smart belt 100 may determine whether the user is wearing the smart belt 100, based on a signal received from at least one of the inertia sensor 111, the waist size sensor 112, the tension sensor 113, and the magnetic sensor.

In operation S4530, the smart belt 100 may acquire motion information of the user who wears the smart belt 100, and tension information. For example, when it is determined that the user is wearing the smart belt 100, the smart belt 100 may acquire the motion information of the user or tension information of the smart belt 100.

According to an exemplary embodiment, the smart belt 100 may sense a motion of the user by using the inertia sensor 111. For example, the smart belt 100 may acquire at least one of a motion of the user, movement speed information of the user, movement direction information of the user, inclination information of the user, and height information of the user.

The smart belt 100 may also acquire location information (for example, GPS coordinate value information, region information, building information, or information about a location variation during a predetermined period) of the user by using a position sensor, and may acquire biometric information (for example, body temperature information, respiration information, and perspiration information) of the user by using a biometric sensor.

According to an exemplary embodiment, the smart belt 100 may acquire the tension information of the smart belt 100 by using the tension sensor 113. For example, the smart belt 100 may measure a tension of the smart belt 100 by using the FSR sensor 102 or the strain gauge 106, but the inventive concept is not limited thereto. A method in which the smart belt 100 acquires the motion information of the user and the tension information of the smart belt 100 has been described above in detail, and thus a repeated description thereof will be omitted.

In operation S4540, the smart belt 100 may transmit the information about whether the user is wearing the smart belt 100, the motion information of the user, and/or the tension information of the smart belt 100 to the host terminal 200.

According to an exemplary embodiment, the smart belt 100 may periodically transmit the information about whether the user is wearing the smart belt 100, the motion information of the user, and/or the tension information of the smart belt 100 to the host terminal 200. For example, the smart belt 100 may transmit the information about whether the user is wearing the smart belt 100, the motion information of the user, and/or the tension information of the smart belt 100 to the host terminal 200 once an hour.

According to an exemplary embodiment, when the smart belt 100 receives a request from the host terminal 200, the smart belt 100 may transmit the information about whether the user is wearing the smart belt 100, the motion information of the user, and/or the tension information of the smart belt 100 to the host terminal 200. For example, when the host terminal 200 receives from the user an input of executing a diary application, the host terminal 200 may request the smart belt 100 for the information about whether the user is wearing the smart belt 100, the motion information of the user, and/or the tension information of the smart belt 100. In this case, the smart belt 100 may transmit the information about whether the user is wearing the smart belt 100, the motion information of the user, and/or the tension information of the smart belt 100 to the host terminal 200.

In operation S4550, the host terminal 200 may generate the activity information of the user by analyzing the information received from the smart belt 100.

For example, the host terminal 200 may generate the activity information of the user, based on the information about whether the user is wearing the smart belt 100, the motion information of the user, or the tension information. The activity information of the user may denote information about activities that are conducted by the user between a wake-up time and a bed time. For example, the activity information of the user may include, but is not limited to, commuting time information, overtime work information, bowel movement information, laugh information, drinking information, smoking information, seizure information, or falling information of the user.

According to an exemplary embodiment, the host terminal 200 may acquire pattern information representing a result of patterning a motion (for example, an acceleration value, an angular speed value, and a tension value of the smart belt 100) corresponding to an activity of the user, and store the pattern information in a memory. The host terminal 200 may generate the activity information of the user by comparing the pattern information stored in the memory with a currently-measured motion of the user.

In operation S4560, the smart belt 200 may display the activity information of the user. For example, the host terminal 200 may execute a specific application according to a user input and may provide the commuting time information, the overtime work information, the defecation information, the laugh information, the drinking information, the smoking information, the seizure information, or the falling information of the user via an application-executed screen image.

According to an exemplary embodiment, the smart belt 100 may transmit the information about whether the user is wearing the smart belt 100, the motion information of the user, and/or the tension information of the smart belt 100 to the server 300, and the server 300 may generate the activity information of the user, based on the information about whether the user is wearing the smart belt 100, the motion information of the user, and/or the tension information of the smart belt 100.

Figure 46:
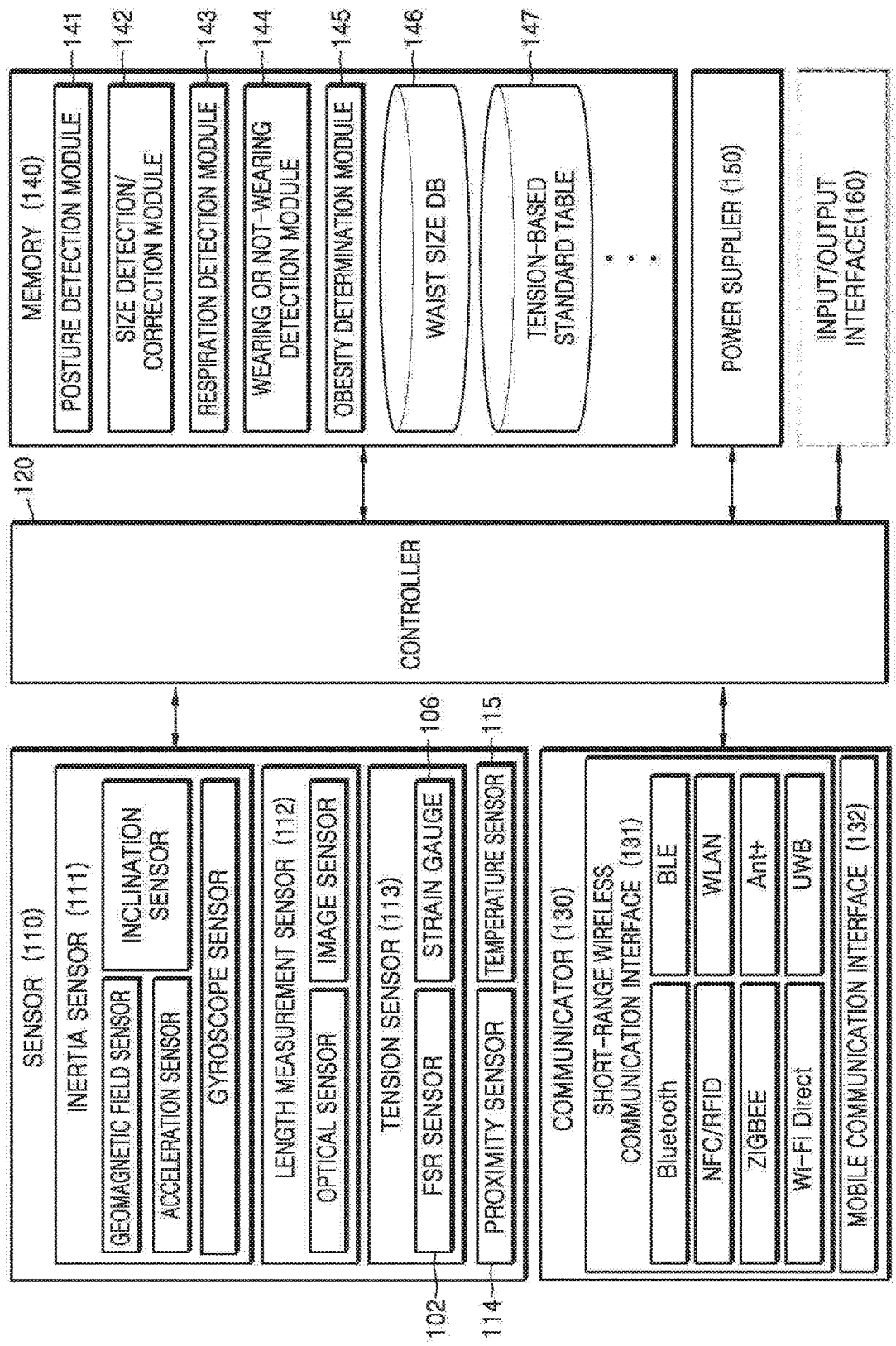
FIG. 46 is a block diagram of a structure of a smart belt according to an exemplary embodiment.

FIG. 46 is a block diagram of a structure of the smart belt 100 according to an exemplary embodiment.

Referring to FIG. 46, the smart belt 100 may include a sensor 110, a controller 120, a communicator 130, a memory 140, and a power supplier 150. However, all of the illustrated components may not be essential. The smart belt 100 may be implemented by more or less components than those illustrated in FIG. 46. For example, the smart belt 100 may further include an input/output interface 160.

The sensor 110 may include at least one sensor for sensing the state of the smart belt 100 or the state of a user who wears the smart belt 100. For example, the sensor 110 may include an inertia sensor 111, a waist size sensor 112, and a tension sensor 113.

The inertia sensor 111 is included to sense a motion of the user who wears the smart belt 100, and may include, but is not limited to, a geomagnetic field sensor, an acceleration sensor, a gyroscope sensor (gyro sensor), and an inclination sensor.

The inertia sensor 111 may acquire, for example, movement or non-movement of the user, movement speed information of the user, movement direction information of the user, inclination information of the user, and height information of the user.

The waist size sensor 112 (or length measurement sensor) is included to sense a waist size of the user who wears the smart belt 100, and may include, but is not limited to, an optical sensor, an image sensor, and a magnetic sensor. For example, the waist size sensor 112 may measure the waist size by using an optical sensor, according to at least one of an incremental linear encoder method, an absolute linear encoder method, an incremental rotary encoder method, and an absolute rotary encoder method. The smart belt 100 may measure the waist size of the user by using the image sensor or the magnetic field sensor.

According to an exemplary embodiment, the waist size sensor 112 may calculate the waist size of the user by measuring the length between first and second points on the smart belt 100.

The tension sensor 113 may measure, for example, a tension applied to the smart belt 100 or a variation of the applied tension. The tension sensor 113 may include, but is not limited to, the FSR sensor 102 or the strain gauge 106. According to an exemplary embodiment, the tension sensor 113 may be positioned between the clip portion 20 and the belt portion 30.

According to an exemplary embodiment, the tension sensor 113 may measure the tension at the third point between the first and second points on the smart belt 100.

The sensor 110 may further include a proximity sensor 114 and a temperature sensor 115. Functions of the above described sensors may be understood by one of ordinary skill in the art and thus detailed descriptions thereof will be omitted herein.

The controller 120 controls overall operations of the smart belt 100. For example, the controller 120 may control the sensor 110, the communicator 130, and the input/output interface 160 by executing programs stored in the memory 140.

The controller 120 may drive an operating system (OS) or an application program to control a plurality of hardware or software components connected to the controller 120, and may perform various data processing and/or calculations. The controller 120 may be implemented using, for example, a system on chip (SoC). For example, the controller 120 may include at least one of a central processing unit (CPU), an application processor (AP), or a communication processor (CP).

According to an exemplary embodiment, the controller 120 may determine whether the user is wearing the smart belt 100, based on a signal received from at least one of the inertia sensor 111, the waist size sensor 112, and the tension sensor 113. For example, when an acceleration value measured by the inertia sensor 111 exceeds a certain value, the waist size sensor 112 identifies a barcode value marked on the belt portion 30 by using the optical sensor, or a tension value measured by the tension sensor 113 exceeds a certain tension value, the controller 120 may determine that the user is wearing the smart belt 100.

The controller 120 may determine a motion state of the user by using the motion information of the user and may control the waist size sensor 112 to measure the waist size of the user according to the motion state of the user. According to an exemplary embodiment, the controller 120 may determine a time to measure the waist size of the user, based on the motion state of the user, and may control the waist size sensor 112 to measure the waist size of the user at the determined time. For example, when the motion state of the user is determined to be an upright-standing state, the controller 120 may activate the waist size sensor 112 to measure the waist size of the user.

The controller 120 may acquire respiration information of the user, based on the tension information, and may determine the time to measure the waist size of the user, based on the respiration information of the user.

The controller 120 may correct the waist size of the user measured by the waist size sensor 112, based on the tension information. For example, the controller 120 may determine a size correction value corresponding to the tension information and apply the size correction value to the measured waist size, thereby correcting the waist size of the user measured by the waist size sensor 112.

According to an exemplary embodiment, the controller 120 may correct the waist size of the user measured by the waist size sensor 112, by taking into account at least one of body information, gender information, and age information of the user.

According to an exemplary embodiment, the controller 120 may determine an abdominal obesity risk of the user, based on information about the corrected waist size.

According to an exemplary embodiment, the controller 120 may correct the length measured by the length measurement sensor 112, by using a tension measured by the tension sensor 113 and stored reference tension information. For example, the controller 120 may extract a length correction value corresponding to the measured tension from the reference tension information, and apply the length correction value to the measured length. The controller 120 may convert the corrected length into a waist size of the user who wears the smart belt 100.

According to an exemplary embodiment, when a measurement value of at least one of the acceleration sensor, the tension sensor 113, a respiration sensor, and the gyroscope sensor corresponds to a certain range, the controller 120 may control the length measurement sensor 112 to measure the length between the first and second points on the smart belt 100.

The controller 120 may further acquire information about a length variation from a certain time point to a current time point, based on the corrected length. The certain time point may be a time point determined by the user or may be a time point when the user starts using the smart belt 100, but the inventive concept is not limited thereto.

The controller 120 may correct the measured tension, based on posture information of the user who wears the smart belt 120 (see FIG. 9). The controller 120 may generate activity information of the user by using at least one of the information about whether the user is wearing the smart belt 100, the motion information of the user, and the tension information of the smart belt 100. For example, the activity information of the user may include, but is not limited to, commuting time information, overtime work information, bowel movement information, laugh information, drinking information, smoking information, seizure information, or falling information of the user.

The communicator 130 may include at least one component that enables the smart belt 100 to perform data communication with the host terminal 200 or the server 300. For example, the communicator 130 may include a short-range wireless communication interface 131 and a mobile communication interface 132.

The short-range wireless communication interface 131 may include, but is not limited to, a Bluetooth communicator, a Bluetooth Low Energy (BLE) communicator, a near field communication (NFC) interface, a wireless local area network (WLAN) (e.g., Wi-Fi) communicator, a ZigBee communicator, an infrared Data Association (IrDA) communicator, a Wi-Fi direct (WFD) communicator, an ultra wideband (UWB) communicator, an Ant+ communicator, and the like.

The mobile communication interface 132 may exchange a wireless signal with at least one from among a base station, an external terminal, and the server 300 on a mobile communication network. The wireless signal may include various types of data.

The communicator 130 may transmit at least one of the information about the waist size measured by the smart belt 100, the information about the corrected waist size obtained by the smart belt 100, the motion information of the user, and the tension information of the smart belt 100 to an external apparatus. The external apparatus may include the host terminal 200, an external wearable device (for example, an HMD, a smart watch, or a band), and the server 300.

According to an exemplary embodiment, the communicator 130 may further transmit information about the abdominal obesity risk to the external apparatus.

The memory 140 may store a program for processing a control operation of the controller 120, and may also store input/output data (for example, the waist size information, the motion information of the user, the reference tension information, the activity information of the user, smoking pattern information, laughing pattern information, drinking pattern information, seizure pattern information, and fall pattern information).

The memory 140 may include, for example, an embedded memory or external memory. The embedded memory include at least one of, for example, a volatile memory (e.g., dynamic random-access memory (DRAM), static random-access memory (SRAM), or synchronous dynamic random-access memory (SDRAM)), a non-volatile memory (e.g., a one time programmable read only memory (OTPROM), programmable read only memory (PROM), erasable and programmable read only memory (EPROM), electrically erasable and programmable read only memory (EEPROM), mask read only memory (ROM), flash ROM), a flash memory (e.g., NAND flash or NOR flash), a hard drive, and a solid state drive (SSD).

The external memory may include a compact flash (CF), a secure digital (SD), a micro-SD, a mini-SD, an extreme digital (XD), a multi-media card (MMC), or a memory stick. The external memory may be functionally and/or physically connected to the smart belt 100 via various interfaces. The smart belt 100 may operate a web storage on the internet which performs a storage function of the memory 140.

The programs stored in the memory 140 may be classified into a plurality of modules according to their functions, for example, a posture detection module 141, a size detection/correction module 142, a respiration detection module 143, a wearing or non-wearing detection module 144, and an obesity determination module 145.

The posture detection module 141 may determine the posture of the user by using, for example, an acceleration variation measured by the acceleration sensor and a tension sensor value measured by the tension sensor 113. For example, when the acceleration variation is greater than a minimum threshold value and the tension sensor value is less than a tension threshold value, the posture detection module 141 may determine that the user is at a standing posture. Since the posture detection module 141 corresponds to the posture detection module 520 of FIG. 5, a repeated description thereof will be omitted.

The size detection/correction module 142 is to calculate or correct the waist size of the user who wears the smart belt 100. Thus, when the posture of the user is a reference posture (for example, an upright-standing state), the size detection/correction module 142 may control the waist size sensor 112 to measure the waist size of the user or may correct the measured waist size based on the tension information of the smart belt 100.

The respiration detection module 143 may detect a breathing cycle, based on a variation of the tension value. The respiration detection module 143 may determine whether the detected breathing cycle is a stable breathing cycle. For example, when the breathing cycle is 3 to 5 seconds and the breathing rate per minute is 12 to 20 times, the respiration detection module 143 may determine that breathing of the user is stable. On the other hand, when the breathing cycle is less than 3 seconds and the breathing rate per minute exceeds 20 times, the respiration detection module 143 may determine that breathing of the user is unstable. The respiration detection module 143 may correspond to the respiration detection module 1100 of FIG. 11.

The wearing or non-wearing detection module 144 may determine whether the user is wearing the smart belt 100, based on a signal received from at least one of the inertia sensor 111, the waist size sensor 112, the magnetic sensor, and the tension sensor 113.

The obesity determination module 145 may determine whether the user who wears the smart belt 100 has abdominal obesity, based on the information about the waist size measured by the waist size sensor 112 or the information about the corrected waist size obtained based on the tension information.

According to an exemplary embodiment, the memory 140 may store information about the waist size. At this time, the memory 140 may compress the information about the waist size and store compressed information, or may not compress the information about the waist size and store uncompressed information. The memory 140 may continuously store waist size information of the user in a waist size database (DB) 146.

According to an exemplary embodiment, the memory 140 may store a tension-based standard table 147 to correct the waist size based on the tension of the smart belt 100.

The power supplier 150 may supply power to at least one sensor disposed within the smart belt 100, in response to a control by the controller 120. The power supplier 150 may be positioned on the buckle portion 10 or the clip portion 20, but the inventive concept is not limited thereto.

As described above, the smart belt 100 may further include the input/output interface 160. The input/output interface 160 may include, but is not limited to, one or more buttons, a touch screen, a microphone, a speaker, a vibration motor, a connector, and an input pen. According to an exemplary embodiment, the input/output interface 160 may be positioned on the buckle portion 10 or the clip portion 20, but the inventive concept is not limited thereto.

For example, the input/output interface 160 may output the information about the waist size of the user (for example, a current waist size and a waist size variation during a certain period of time), the abdominal obesity risk, and the like. The input/output interface 160 may receive a user input.

Figure 47:
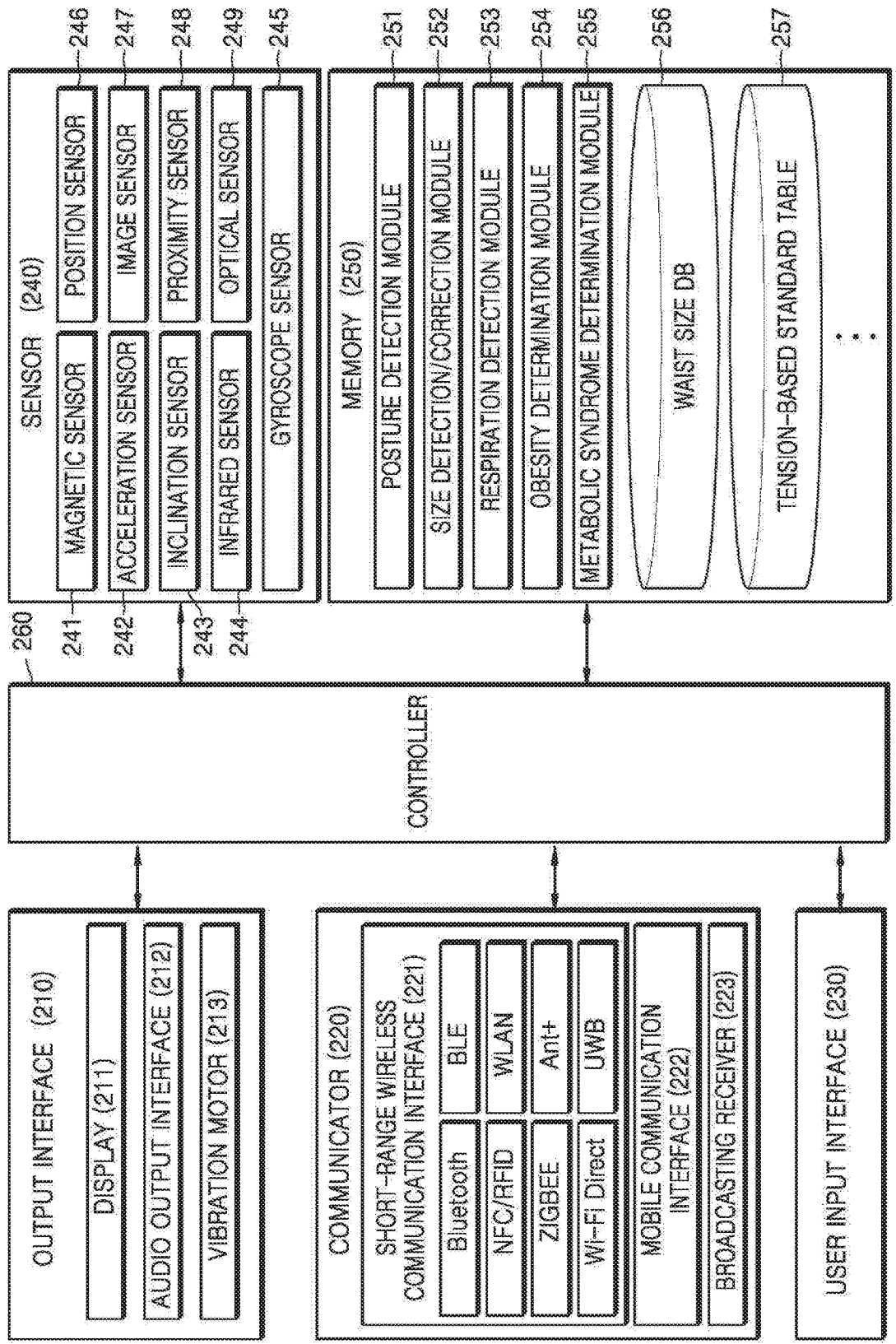
FIG. 47 is a block diagram of a structure of a host terminal according to an exemplary embodiment.

FIG. 47 is a block diagram of a structure of the host terminal 200 according to an exemplary embodiment.

Referring to FIG. 47, the host terminal 200 may include an output interface 210, a communicator 220, a user input interface 230, a sensor 240, a memory 250, and a controller 260. However, all of the illustrated components may not be essential. The host terminal 200 may be implemented by more or less components than those illustrated in FIG. 47. For example, the host terminal 200 may further include an audio/video (A/V) input interface (not shown).

The output interface 210 outputs an audio signal, a video signal, or a vibration signal, and may include a display 211, an audio output interface 212, and a vibration motor 213.

The display 211 may display information that is processed by the host terminal 200. For example, the display 211 may display information about the waist size of the user who wears the smart belt 100.

When the display 211 forms a layer structure together with a touch pad to provide a touch screen, the display 211 may be used as an input device as well as an output device. The display 211 may include at least one of a liquid crystal display (LCD), a thin film transistor-liquid crystal display (TFT-LCD), an organic light-emitting diode (OLED), a flexible display, a three dimensional (3D) display, and an electrophoretic display. According to embodiments of the host terminal 200, the host terminal 200 may include at least two displays 211. The at least two displays 211 may be disposed to face each other by using a hinge.

The audio output interface 212 outputs audio data that is received from the communicator 220 or stored in the memory 250. The audio output interface 212 may also output an audio signal (for example, a call signal receiving sound, a message receiving sound, a notification sound) related to a function of the host terminal 200. The audio output interface 212 may include, for example, a speaker and a buzzer.

The vibration motor 213 may output a vibration signal. For example, the vibration motor 213 may output a vibration signal corresponding to an output of audio data or video data (for example, a call signal receiving sound or a message receiving sound). The vibration motor 213 may also output a vibration signal when waist size information is received from the smart belt 100.

According to an exemplary embodiment, the output interface 210 may output information about a corrected waist size. For example, the output interface 210 may output the information about the corrected waist size in the form of a voice, a text, a still image, or a moving picture, but the inventive concept is not limited thereto.

The output interface 210 may output the information about the corrected waist size every time the information about the corrected waist size is received from the smart belt 100. Alternatively, when the output interface 210 receives from the user an input of requesting a health care application to be executed, the output interface 210 may output the information about the corrected waist size via an execution window of the health care application.

The output interface 210 may display information about a current waist size and further display a waist size variation during a predetermined period of time, a target waist size, and the like. The output interface 210 may also output information about an abdominal obesity and may output a warning message representing a metabolic syndrome.

The output interface 210 may output, for example, a warning message warning a health risk, an encouraging message encouraging a heath care, and a message informing that the target waist size has been achieved, based on the information about the waist size received from the smart belt 100. The output interface 210 may display a change in the waist size as a graph or as an icon image.

According to an exemplary embodiment, the output interface 210 may provide information related to a health care to the user. For example, the output interface 210 may output information about an exercise that may contribute in reducing the waist size, information about a food that may contribute in reducing the waist size, diet information, and information about a recipe that may contribute in reducing the waist size.

The communicator 220 may include at least one component that enables the host terminal 200 to perform data communication with the smart belt 100 or the server 300. For example, the communicator 220 may include a short-range wireless communication interface 221, a mobile communication interface 222, and a broadcasting receiver 223.

The short-range wireless communication interface 221 may include, but is not limited to, a Bluetooth communicator, a Bluetooth Low Energy (BLE) communicator, a near field communication (NFC) interface, a wireless local area network (WLAN) (e.g., Wi-Fi) communicator, a ZigBee communicator, an infrared Data Association (IrDA) communicator, a Wi-Fi direct (WFD) communicator, an ultra wideband (UWB) communicator, an Ant+ communicator, and the like.

The mobile communication interface 222 may exchange a wireless signal with at least one from among a base station, an external terminal, and the server 300 on a mobile communication network. Examples of the wireless signal may include a voice call signal, a video call signal, and various types of data generated during a short message service (SMS)/multimedia messaging service (MMS).

The broadcasting receiver 223 receives a broadcasting signal and/or broadcasting-related information from an external source via a broadcasting channel. The broadcasting channel may be a satellite channel, a ground wave channel, or the like. According to embodiments, the host terminal 200 may not include the broadcasting receiver 223.

The communicator 220 may receive the information about the waist size of the user measured by the smart belt 100, the motion information of the user, and the tension information of the smart belt 100 from the smart belt 100.

According to an exemplary embodiment, the communicator 220 may further receive the information about the abdominal obesity risk from the smart belt 100. The communicator 220 may receive the information about the abdominal obesity risk and the information about the metabolic syndrome from the server 300.

The communicator 220 may receive at least two of blood sugar information, cholesterol information, blood pressure information, and neutral fat information from external apparatuses (for example, a blood pressure machine and a blood sugar machine).

The user input interface 230 denotes a unit via which a user inputs data for controlling the host terminal 200. For example, the user input interface 230 may be, but is not limited to, a key pad, a dome switch, a touch pad (e.g., a capacitive overlay type, a resistive overlay type, an infrared beam type, an integral strain gauge type, a surface acoustic wave type, a piezo electric type, or the like), a jog wheel, or a jog switch.

The sensor 240 may sense a state of the host terminal 200 or a state of the surrounding of the host terminal 200 and may transmit information corresponding to the sensed state to the controller 260.

The sensor 240 may include, but is not limited to, at least one from among a magnetic sensor 241, an acceleration sensor 242, an inclination sensor 243, an infrared sensor 244, a gyroscope sensor 245, a position sensor 246, an image sensor 247, a proximity sensor 248, and an optical sensor 249. Functions of the above sensors would be understood by one of ordinary skill in the art and thus detailed descriptions thereof will be omitted herein.

The memory 250 may store a program for processing a control operation of the controller 260, and may also store input/output data (for example, the waist size information, the motion information of the user, and the tension information).

The memory 250 may include, for example, an embedded memory or external memory. The embedded memory include at least one of, for example, a volatile memory (e.g., DRAM, SRAM, or SDRAM), a non-volatile memory (e.g., OTPROM, PROM, EPROM, EEPROM, mask ROM, flash ROM), a flash memory (e.g., NAND flash or NOR flash), a hard drive, and an SSD.

The external memory may include a CF, an SD, a micro-SD, a mini-SD, an XD, an MMC, or a memory stick. The external memory may be functionally and/or physically connected to the host terminal 200 via various interfaces. The host terminal 200 may operate a web storage on the internet which performs a storage function of the memory 250.

The programs stored in the memory 250 may be classified into a plurality of modules according to their functions, for example, a posture detection module 251, a size correction module 252, a respiration detection module 253, an obesity determination module 254, a metabolic syndrome determination module 255, and an activity information generation module (not shown), but the inventive concept is not limited thereto.

The posture detection module 251 may determine the posture of the user by using, for example, the motion information of the user received from the smart belt 100 (e.g., an acceleration variation measured by an acceleration sensor) and the tension sensor value measured by the tension sensor 113. For example, when the acceleration variation is greater than a minimum threshold value and the tension sensor value is less than a tension threshold value, the posture detection module 251 may determine that the user is at a standing posture.

The size correction module 252 may correct the waist size measured by the waist size sensor 112 of the smart belt 100. For example, the size correction module 252 may correct the measured waist size, based on the tension information of the smart belt 100.

The respiration detection module 253 may detect a breathing cycle, based on a variation of the tension value. The respiration detection module 253 may determine whether the detected breathing cycle is a stable breathing cycle. For example, when the breathing cycle is 3 to 5 seconds and the breathing rate per minute is 12 to 20 times, the respiration detection module 253 may determine that breathing of the user is stable. On the other hand, when the breathing cycle is less than 3 seconds and the breathing rate per minute exceeds 20 times, the respiration detection module 253 may determine that breathing of the user is unstable.

The obesity determination module 254 may determine whether the user who wears the smart belt 100 has abdominal obesity, based on the information about the waist size of the user who wears the smart belt 100. The metabolic syndrome determination module 255 may diagnose a metabolic syndrome, based on the information about the waist size received from the smart belt 100 and at least two of the blood sugar information, the cholesterol information, the blood pressure information, and the neutral fat information of the user.

According to an exemplary embodiment, the memory 250 may store information about the waist size of the user. At this time, the memory 250 may compress information about the waist size and store the compressed information, or may not compress the information about the waist size and store the uncompressed information. According to an exemplary embodiment, the memory 250 may continuously store waist size information of the user in a waist size DB 256. According to an exemplary embodiment, the memory 250 may store a tension-based standard table 257 to correct the waist size based on the tension of the smart belt 100.

The controller 260 controls overall operations of the host terminal 200. For example, the controller 260 may control the output interface 210, the communicator 220, the user input interface 230, and the sensor 240 by executing the programs stored in the memory 250.

The controller 260 may determine a motion state of the user by using the motion information of the user, and may correct the waist size of the user measured by the smart belt 100, based on at least one of the motion state of the user and the tension information of the smart belt 100.

The controller 260 may determine an abdominal obesity risk of the user, based on information about the corrected waist size. The controller 260 may diagnose a metabolic syndrome, based on the information about the waist size and at least two of the blood sugar information, the cholesterol information, the blood pressure information, and the neutral fat information of the user.

Figure 48:
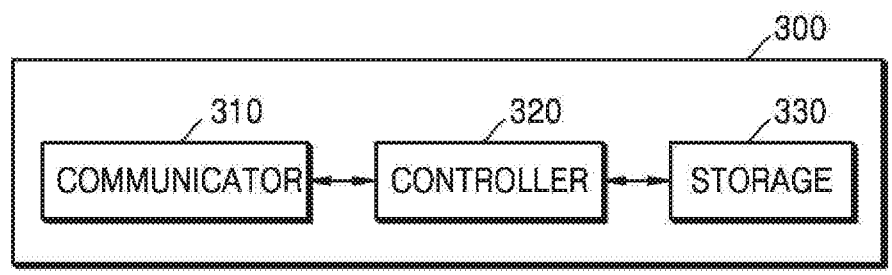
FIG. 48 is a block diagram of a structure of a server according to an exemplary embodiment.

FIG. 48 is a block diagram of a structure of the server 300 according to an exemplary embodiment.

Referring to FIG. 48, the server 300 may include a communicator 310, a controller 320, and a storage 330. However, all of the illustrated components may not be essential. The server 300 may be implemented by more or less components than those illustrated in FIG. 48.

The communicator 310 may include at least one component that enables communication between the server 300 and the smart belt 100 or between the server 300 and the host terminal 200.

For example, the communicator 310 may receive at least one of the motion information of the user, the information about the waist size of the user, the tension information of the smart belt 100, and the information about the corrected waist size obtained based on the tension information from the smart belt 100.

The communicator 310 may transmit the information about the corrected waist size to the host terminal 200. The communicator 310 may transmit information about an abdominal obesity risk and/or a metabolic syndrome to the host terminal 200.

The controller 320 controls operations of the server 300. For example, the controller 320 may determine a motion state of the user by using the motion information of the user, and may correct the waist size of the user measured by the smart belt 100, based on at least one of the motion state of the user and the tension information of the smart belt 100.

The controller 320 may determine an abdominal obesity risk of the user, based on information about the corrected waist size. The controller 320 may diagnose a metabolic syndrome, based on the information about the waist size and at least two of the blood sugar information, the cholesterol information, the blood pressure information, and the neutral fat information of the user.

The storage 330 may store a program that is used by the controller 320 to perform processing, or may store input/output data. For example, the storage 330 may store a posture detection module, a size correction module, a respiration detection module, an obesity determination module, and a metabolic syndrome determination module. The storage 330 may systematically establish a waist size DB to manage waist size information of the user. The storage 330 may also store a tension-based standard table, human body modeling information, and the like.

According to an exemplary embodiment, since the smart belt 100 determines whether to measure the waist size of the user, according to the motion state of the user, the smart belt 100 may measure the waist size at a posture adequate to measure the waist size. Since the smart belt 100 corrects the measured waist size according to the tension information of the smart belt 100, the smart belt 100 may provide accurate waist size information to the user.

A method according to an exemplary embodiment may be embodied as program commands executable by various computers and may be recorded on a non-transitory computer-readable recording medium. The non-transitory computer-readable recording medium may include program commands, data files, data structures, and the like separately or in combinations. The program commands to be recorded on the non-transitory computer-readable recording medium may be specially designed and configured for embodiments of the inventive concept or may be well-known to and be usable by one of ordinary skill in the art of computer software. Examples of the non-transitory computer-readable recording medium include a magnetic medium such as a hard disk, a floppy disk, or a magnetic tape, an optical medium such as a compact disk-read-only memory (CD-ROM) or a digital versatile disk (DVD), a magneto-optical medium such as an optical disk, and a hardware device specially configured to store and execute program commands such as a ROM, a random-access memory (RAM), or a flash memory. Examples of the program commands are advanced language codes that can be executed by a computer by using an interpreter or the like as well as machine language codes made by a compiler.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like Although a few embodiments have been shown and described, it would be appreciated by those skilled in the art that changes may be made in exemplary embodiments without departing from the principles and spirit of the disclosure, the scope of which is defined in the claims and their equivalents.

What is claimed is:

1. A smart belt apparatus for providing information that is used to provide a service regarding a body of a user, the smart belt apparatus comprising:
a communication interface configured to transmit or receive data to or from an external device;
at least one first sensor configured to sense that the smart belt apparatus is being worn by the user;
at least one second sensor configured to sense a movement of the user; and
a processor configured to, in response to the at least one first sensor sensing that the smart belt apparatus is being worn by the user, make a determination whether a current posture of the user is a reference posture that is pre-defined, measure a waist size of the user by using the at least one first sensor, correct the measured waist size based on the determination, sense a motion of the user by using the at least one second sensor, and provide information about the measured waist size of the user and information about the sensed motion to the external device via the communication interface,
wherein the processor is further configured to:
correct the measured waist size based on a first tension value corresponding to the reference posture based on a determination that the current posture of the user is the reference posture; and
correct the measured waist size based on a second tension value estimated from the first tension value by using a human body modeling information based on a determination that the current posture of the user is not the reference posture.

2. The smart belt apparatus of claim 1, comprising:
a belt configured to surround a waist of the user;
a buckle bonded with the belt; and
a clip positioned between the belt and the buckle and configured to connect the belt and the buckle together,
wherein the communication interface and the processor are provided in the clip.

3. The smart belt apparatus of claim 2, wherein
the processor is configured to determine whether the user overeats, as the measured waist size of the user increases, and
the communication interface is configured to transmit to the external device information about whether the user overeats.

4. The smart belt apparatus of claim 2, wherein the processor is configured to identify a hole currently being used from among a plurality of holes provided in the belt of the smart belt apparatus and measure the waist size based on the identified hole.

5. The smart belt apparatus of claim 4, wherein
the at least one first sensor comprises a magnetic sensor provided in the belt of the smart belt apparatus, and
the processor is configured to identify the hole currently being used, by using the magnetic sensor.

6. The smart belt apparatus of claim 1, further comprising a tension sensor configured to measure a tension that is applied to a belt of the smart belt apparatus due to expansion of a waist of the user,
wherein the processor is configured to transmit information about the measured tension to the external device via the communication interface.

7. The smart belt apparatus of claim 6, wherein
the processor is configured to estimate a number of respirations of the user per unit time, based on the measured tension, and
the communication interface is configured to transmit information of the number of respirations of the user per unit time to the external device.

8. The smart belt apparatus of claim 1, wherein
the processor is configured to generate activity information of the user, based on the information about the measured waist size and the information about the sensed motion, and
the communication interface is configured to transmit the generated activity information to the external device.

9. The smart belt apparatus of claim 1, wherein
the processor is configured to generate information about a time at which the waist size of the user was measured and a time at which the motion of the user was sensed, and
the communication interface is configured to transmit, to the external device, the information about the time at which the waist size of the user was measured and the information about the time at which the motion of the user was sensed, together with the information about the measured waist size and the information about the sensed motion.

10. The smart belt apparatus of claim 1, wherein the processor is configured to control the at least one first sensor to generate information about whether the smart belt apparatus is attached to or detached from the user, and provide the information about whether the smart belt apparatus is attached or detached to or from the user to the external device via the communication interface.

11. The smart belt apparatus of claim 1, wherein the processor is configured to collect information about the motion while it is being sensed that the smart belt apparatus is being worn by the user.

12. A non-transitory computer readable storage medium having recorded thereon at least one program including instructions for performing a method of providing a service regarding a body of a user, the method comprising:
controlling a communication interface to receive information about a waist size of the user from a smart belt apparatus;
controlling the communication interface to receive information about a motion of the user from the smart belt apparatus; and
controlling a display to provide information about a body state of the user, based on the received information about the waist size of the user and the received information about the motion of the user,
wherein the waist size of the user is measured by the smart belt apparatus based on whether a current posture of the user is a reference posture that is pre-defined,
wherein the method further comprises:
correcting the measured waist size based on a first tension value corresponding to the reference posture based on a determination that the current posture of the user is the reference posture; and correcting the measured waist size based on a second tension value estimated from the first tension value by using a human body modeling information based on a determination that the current posture of the user is not the reference posture.

13. The non-transitory computer readable storage medium of claim 12, wherein the information about the waist size is generated as the waist size of the user is measured by a first sensor within the smart belt apparatus, and the information about the motion is generated as the motion of the user is sensed by a second sensor within the smart belt apparatus.

14. The non-transitory computer readable storage medium of claim 13, wherein the information about the waist size and the information about the motion are generated within the smart belt apparatus as the first sensor senses that the smart belt apparatus is being worn by the user.

15. The non-transitory computer readable storage medium of claim 12, wherein the method further comprises generating information about a time period during which the user sits, based on the information about the motion,
   wherein the controlling of the display to provide the information about the body state of the user comprises controlling the display to display a graphical user interface (GUI) representing the information about the time period during which the user sits.

16. The non-transitory computer readable storage medium of claim 12, wherein the method further comprises generating information about whether the user overeats, based on the information about the waist size,
   wherein the controlling of the display to provide the information about the body state of the user comprises controlling the display to display a graphical user interface (GUI) representing the information about whether the user overeats.

17. The non-transitory computer readable storage medium of claim 12, wherein the method further comprises generating information about a change of the waist size of the user, based on the information about the waist size,
   wherein the controlling of the display to provide the information about the body state of the user comprises controlling the display to display a graphical user interface (GUI) representing the information about the change of the waist size of the user.

* * * * *